United States Patent
Collins et al.

(10) Patent No.: US 9,403,797 B2
(45) Date of Patent: *Aug. 2, 2016

(54) 5-(PYRIDIN-2-YL-AMINO)-PYRAZINE-2-CARBONITRILE COMPOUNDS AND THEIR THERAPEUTIC USE

(71) Applicant: Cancer Research Technology Limited, London, Greater London (GB)

(72) Inventors: Ian Collins, Sutton (GB); Michael Lainchbury, Harlow (GB); Thomas Peter Matthews, Sutton (GB); John Charles Reader, Cambridge (GB)

(73) Assignee: Cancer Research Technology Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/693,307

(22) Filed: Apr. 22, 2015

(65) Prior Publication Data

US 2015/0225372 A1 Aug. 13, 2015

Related U.S. Application Data

(63) Continuation of application No. 14/356,626, filed as application No. PCT/GB2012/052786 on Nov. 9, 2012, now Pat. No. 9,040,540.

(60) Provisional application No. 61/557,457, filed on Nov. 9, 2011.

(51) Int. Cl.
| A61K 31/497 | (2006.01) |
| C07D 401/12 | (2006.01) |
| C07D 401/14 | (2006.01) |
| A61K 45/06 | (2006.01) |
| A61N 5/10 | (2006.01) |

(52) U.S. Cl.
CPC ............ *C07D 401/14* (2013.01); *A61K 31/497* (2013.01); *A61K 45/06* (2013.01); *A61N 5/10* (2013.01); *C07D 401/12* (2013.01); *A61N 2005/1098* (2013.01)

(58) Field of Classification Search
CPC .......................... A61K 31/497; C07D 401/12
See application file for complete search history.

(56) References Cited

U.S. PATENT DOCUMENTS

| 3,773,778 | A | 11/1973 | Hoehn |
| 8,058,045 | B2 | 11/2011 | Collins |
| 8,367,658 | B2 | 2/2013 | Collins |
| 8,530,468 | B2 | 9/2013 | Collins |
| 8,618,121 | B2 | 12/2013 | Collins |
| 9,040,540 | B2 | 5/2015 | Collins |
| 2005/0215556 | A1 | 9/2005 | Lin |
| 2010/0210639 | A1 | 8/2010 | Collins |
| 2010/0311730 | A1 | 12/2010 | Collins |
| 2010/0331328 | A1 | 12/2010 | Collins |
| 2012/0040967 | A1 | 2/2012 | Collins |
| 2014/0315925 | A1 | 10/2014 | Collins |
| 2015/0126471 | A1 | 5/2015 | Collins |

FOREIGN PATENT DOCUMENTS

| WO | WO 95-19970 A1 | 7/1995 |
| WO | WO 97-02266 A1 | 1/1997 |
| WO | WO 03-032984 A1 | 4/2003 |
| WO | WO 03-035065 A1 | 5/2003 |
| WO | WO 03-037898 A1 | 5/2003 |
| WO | WO 03-093297 A2 | 11/2003 |
| WO | WO 03-101444 A1 | 12/2003 |

(Continued)

OTHER PUBLICATIONS

Lainchbury, M. et al. "Discovery of 3-Alkoxyamino-5-(pyridine-2-ylamino)pyrazine-2-carbonitriles as Selective, Orally Bioavailable CHK1 Inhibitors." J. Med. Chem. (2012), vol. 55, pp. 10229-10240.*
GB Search Report for GB 0719644.7 dated Apr. 25, 2008.
GB Search Report for GB 0803018.1 dated Jun. 17, 2008.
International Search Report for PCT-GB2008-002259 dated Sep. 19, 2008.
International Search Report for PCT-GB2008-003362 dated Jan. 29, 2009.
International Search Report for PCT-GB2009-000438 dated Jul. 20, 2009.
International Search Report for PCT-GB2012-052786 dated Feb. 6, 2013.
International Search Report for PCT-GB2013-051233 dated Jul. 26, 2013.

(Continued)

*Primary Examiner* — Noble Jarrell
*Assistant Examiner* — John S Kenyon
(74) *Attorney, Agent, or Firm* — Swanson & Bratschun, L.L.C.

(57) ABSTRACT

The present invention pertains generally to the field of therapeutic compounds. More specifically the present invention pertains to certain pyridyl-amino-pyrazine carbonitrile compounds that, inter alia, inhibit Checkpoint Kinase 1 (CHK1) kinase function. The present invention also pertains to pharmaceutical compositions comprising such compounds, and the use of such compounds and compositions, both in vitro and in vivo, to inhibit CHK1 kinase function, and in the treatment of diseases and conditions that are mediated by CHK1, that are ameliorated by the inhibition of CHK1 kinase function, etc., including proliferative conditions such as cancer, etc., optionally in combination with another agent, for example, (a) a DNA topoisomerase I or II inhibitor; (b) a DNA damaging agent; (c) an antimetabolite or thymidylate synthase (TS) inhibitor; (d) a microtubule targeted agent; and (e) ionising radiation.

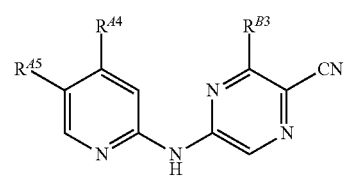

38 Claims, 1 Drawing Sheet

(56) References Cited

FOREIGN PATENT DOCUMENTS

| WO | WO 2005-011597 A2 | 2/2005 |
|---|---|---|
| WO | WO 2005-034869 A2 | 4/2005 |
| WO | WO 2005-037285 A1 | 4/2005 |
| WO | WO 2005-037825 A2 | 4/2005 |
| WO | WO 2005-047294 A1 | 5/2005 |
| WO | WO 2005-121126 A1 | 12/2005 |
| WO | WO 2006-039718 A2 | 4/2006 |
| WO | WO 2006-116733 A2 | 11/2006 |
| WO | WO 2007-000240 A1 | 1/2007 |
| WO | WO 2007-041712 A1 | 4/2007 |
| WO | WO 2007-044779 A1 | 4/2007 |
| WO | WO 2008-077554 A1 | 7/2008 |
| WO | WO 2008-115369 A2 | 9/2008 |
| WO | WO 2008-117050 A1 | 10/2008 |
| WO | WO 2009-004329 A1 | 1/2009 |
| WO | WO 2009-044162 A1 | 4/2009 |
| WO | WO 2009-103966 A1 | 8/2009 |
| WO | WO 2013-068755 A1 | 5/2013 |
| WO | WO 2013-171470 A1 | 11/2013 |

OTHER PUBLICATIONS

International Preliminary Report on Patentability for PCT-GB2008-002259 dated Jan. 5, 2010.
International Preliminary Report on Patentability for PCT-GB2008-003362 dated Apr. 7, 2010.
International Preliminary Report on Patentability for PCT-GB2009-000438 dated Aug. 24, 2010.
International Preliminary Report on Patentability for PCT-GB2012-052786 dated Jan. 29, 2014.
Balint et al., 2001, "Activation and activities of the p53 tumour suppressor protein," Br. J. Cancer, vol. 85, pp. 1813-1823.
Bartek et al., 2003, "Chk1 and Chk2 kinases in checkpoint control and cancer," Cancer Cell, vol. 3, pp. 421-429.
Brooks et al., 2012, "A potent chk1 inhibitor is selectively toxic in melanomas with high levels of replicative stress," Oncogene, vol. 32, pp. 788-796.
Carson et al., 1995, "Cancer progression and p53," Lancet, vol. 346, pp. 1009-1011.
Cavelier et al., 2009, "Constitutive activation of the DNA damage signaling pathway in acute myeloid leukemia with complex karyotype: Potential importance for checkpoint targeting therapy," Cancer Res., vol. 69, pp. 8652-8661.
Cole et al., 2011 "RNAi screen of the protein kinome identifies checkpoint kinase 1 (chk1) as a therapeutic target in neuroblastoma," Proc. Natl. Acad. Sci. U.S.A., vol. 108, pp. 3336-3341.
Davies et al., 2011, "Single-agent inhibition of chk1 is antiproliferative in human cancer cell lines in vitro and inhibits tumor xenograft growth in vivo," Oncol. Res., vol. 19, pp. 349-363.
Di Micco et al., 2006, "Oncogene-induced senescence is a DNA damage response triggered by DNA hyper-replication," Nature, vol. 444, pp. 638-642.
Dixon et al., 2002, "Therapeutic exploitation of checkpoint defects in cancer cells lacking p53 function," Cell Cycle, vol. 1, pp. 362-368.
Durola et al., 2007, "A New Family of Biisoquinoline Chelates", Eur. J. Org. Chem., Issue 1, pp. 125-135.
Ferrao et al., 2011, "Efficacy of chk inhibitors as single agents in myc-driven lymphoma cells," Oncogene, vol. 31, pp. 1661-1672.
Gabriel et al., 1908, "Ubergang von der Chinoxalin zur Pyrazinreihe", Berichte der Deutschen Chemischen Gesellschaft, vol. 40, pp. 4850-4860 (with Engilsh Abstract).
Greenblatt et al., 1994, "Mutations in the p53 tumor suppressor gene: clues to cancer etiology and molecular pathogenesis," Cancer Res., vol. 54, pp. 4855-4878.
Guzi et al., 2011, "Targeting the replication checkpoint using SCH 900776, a potent and functionally selective CHK1 inhibitor identified via high content screening," Mol. Cancer Ther., vol. 10, pp. 591-602.

Höglund et al., 2011, "Therapeutic Implications for the Induced Levels of Chk1 in Myc-Expressing Cancer Cells," Clin. Cancer Res., vol. 17, pp. 7067-7079.
Ioannidis et al., "Discovery of pyrazol-3-ylamino pyrazines as novel JAK2 inhibitors", Bioorg. & Med. Chem. Lett., 2009, vol. 19, pp. 6524-6528.
Itoh et al., 2002, "Efficient synthesis of substituted 2-aminopyrazines: FeCl3-promoted condensation of hydroxyiminoketones with aminoacetonitriles", Tetrahedron Lett., vol. 43, pp. 9287-9290.
Lainchbury et al., Oct. 19, 2012, "Discovery of 3-Alkoxyamino-5-(pyridin-2-ylamino)pyrazine-2-carbonitriles as Selective, Orally Bioavailable CHK1 Inhibitors", J. Med. Chem., vol. 55, No. 22, pp. 10229-10240.
Lainchbury et al., 2011, "Checkpoint kinase inhibitors: a patent review (2009-2010)", Exp. Opin. Ther. Pat., vol. 21, No. 8, pp. 1911-1210.
Li et al., 2007, "Synthesis and in-vitro biological activity of macrocyclic urea CHK1 inhibitors", Bioorg. & Med. Chem. Lett., vol. 17, pp. 6499-6504.
Liu et al., 2000, "Chk1 is an essential kinase that is regulated by Atr and required for the G(2)/M DNA damage checkpoint," Genes Dev., vol. 14, pp. 1448-1459.
Murga et al., 2011, "Exploiting oncogene-induced replicative stress for the selective killing of Myc-driven tumors," Nat. Struct. Mol. Biol., vol. 18, pp. 1331-1335.
Sanchez et al., 1997, "Conservation of the Chk1 checkpoint pathway in mammals: linkage of DNA damage to CDK regulation through Cdc25," Science, vol. 277, pp. 1497-1501.
Sorensen et al., 2005, "Cell-cycle checkpoint kinase Chk1 is required for mammalian homologous recombination repair," Nat. Cell Biol., vol. 7, pp. 195-201.
Tao et al., 2006, "Chk1 inhibitors for novel cancer treatment," Anti-Cancer Agents in Medicinal Chemistry, vol. 6, pp. 377-388.
Tao et al., 2007, "Macrocyclic ureas as potent and selective CHK1 inhibitors: an improved synthesis, kinome profiling, structure-activity relationships, and preliminary pharmacokinetics," Bioorg. Med. Chem. Lett., vol. 17, pp. 6593-6601.
Tao et al., 2007, "Structure-based design, synthesis, and biological evaluation of potent and selective macrocyclic checkpoint kinase 1 inhibitors," J. Med. Chem., vol. 50, pp. 1514-1527.
Ugarkar et al., 2000, "Adenosine Kinase Inhibitors. 1. Synthesis, Enzyme Inhibition, and Antiseizure Activity of 5-Iodotubercidin Analogues," Journal of Medicinal Chemistry, vol. 43, pp. 2883-2893.
Walton et al., 2010, "The Preclinical Pharmacology and Therapeutic Activity of the Novel CHK1 Inhibitor SAR-020106", Molecular Cancer Therapeutics, vol. 9(1), pp. 89-100.
Walton et al., 2012, "CCT244747 is a Novel Potent and Selective CHK1 Inhibitor with Oral Efficacy Alone and in Combination with Genotoxic Anticancer Drugs", Clin. Cancer Res., vol. 18, pp. 5650-5661.
Wang et al., 1996, "UCN-01: a potent abrogator of G2 checkpoint function in cancer cells with disrupted p53," J. Natl. Cancer Inst., vol. 8, pp. 956-965.
Weinert et al., 1989, "Control of G2 delay by the rad9 gene of *Saccharomyces cerevisiae*," J. Cell Sci. Suppl., vol. 12, pp. 145-148.
White et al., 1967, "Gattermann reaction of 3,5-dimethoxyphenylacetonitrile. Synthesis of 6,8-dioxyisoquinolines", J. Org. Chem., vol. 32, pp. 2689-2692.
Xiao et al., 2006, "Differential roles of checkpoint kinase 1, checkpoint kinase 2, and mitogen-activated protein kinase-activated protein kinase 2 in mediating DNA damage-induced cell cycle arrest: implications for cancer therapy," Mol. Cancer Ther., vol. 5, pp. 1935-1943.
Zachos et al., 2003, "Chk1-deficient tumour cells are viable but exhibit multiple checkpoint and survival defects," EMBO J., vol. 22, pp. 713-723.
Zhao et al., 2002, "Disruption of the checkpoint kinase 1/cell division cycle 25A pathway abrogates ionizing radiation-induced S and G2 checkpoints," Proc. Natl. Acad. Sci. USA, vol. 99, pp. 14795-14800.

* cited by examiner

5-(PYRIDIN-2-YL-AMINO)-PYRAZINE-2-CARBONITRILE COMPOUNDS AND THEIR THERAPEUTIC USE

RELATED APPLICATION

This application is a continuation of U.S. application Ser. No. 14/356,626, filed May 7, 2014, which application is a 35 U.S.C. §371 national phase application of PCT application serial number PCT/GB2012/052786 (WO 2013/068755), filed Nov. 9, 2012. PCT application serial number PCT/GB2012/052786 claims priority to U.S. application No. 61/557,457 filed Nov. 9, 2011. The contents of each of these applications are incorporated herein by reference in their entirety.

TECHNICAL FIELD

The present invention pertains generally to the field of therapeutic compounds. More specifically the present invention pertains to certain pyridyl-amino-pyrazine carbonitrile compounds that, inter alia, inhibit Checkpoint Kinase 1 (CHK1) kinase function. The present invention also pertains to pharmaceutical compositions comprising such compounds, and the use of such compounds and compositions, both in vitro and in vivo, to inhibit CHK1 kinase function, and in the treatment of diseases and conditions that are mediated by CHK1, that are ameliorated by the inhibition of CHK1 kinase function, etc., including proliferative conditions such as cancer, etc., optionally in combination with another agent, for example, (a) a DNA topoisomerase I or II inhibitor; (b) a DNA damaging agent; (c) an antimetabolite or thymidylate synthase (TS) inhibitor; (d) a microtubule targeted agent; and (e) ionising radiation.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Checkpoint Kinase 1 (CHK1)

Progression through the cell division cycle is a tightly regulated process and is monitored at several positions known as cell cycle checkpoints (see, e.g., Weinert and Hartwell, 1989; Bartek and Lukas, 2003). These checkpoints are found in all four stages of the cell cycle; G1, S (DNA replication), G2 and M (Mitosis) and they ensure that key events which control the fidelity of DNA replication and cell division are completed correctly. Cell cycle checkpoints are activated by a number of stimuli, including DNA damage and DNA errors caused by defective replication. When this occurs, the cell cycle will arrest, allowing time for either DNA repair to occur or, if the damage is too severe, for activation of cellular processes leading to controlled cell death.

All cancers, by definition, have some form of aberrant cell division cycle. Frequently, the cancer cells possess one or more defective cell cycle checkpoints, or harbour defects in a particular DNA repair pathway. These cells are therefore often more dependent on the remaining cell cycle checkpoints and repair pathways, compared to non-cancerous cells (where all checkpoints and DNA repair pathways are intact). The response of cancer cells to DNA damage is frequently a critical determinant of whether they continue to proliferate or activate cell death processes and die. For example, tumour cells that contain a mutant form(s) of the tumour suppressor p53 are defective in the G1 DNA damage checkpoint. Thus inhibitors of the G2 or S-phase checkpoints are expected to further impair the ability of the tumour cell to repair damaged DNA.

Many known cancer treatments cause DNA damage by either physically modifying the cell's DNA or disrupting vital cellular processes that can affect the fidelity of DNA replication and cell division, such as DNA metabolism, DNA synthesis, DNA transcription and microtubule spindle formation. Such treatments include for example, radiotherapy, which causes DNA strand breaks, and a variety of chemotherapeutic agents including topoisomerase inhibitors, antimetabolites, DNA-alkylating agents, and platinum-containing cytotoxic drugs. A significant limitation to these genotoxic treatments is drug resistance. One of the most important mechanisms leading to this resistance is attributed to activation of cell cycle checkpoints, giving the tumour cell time to repair damaged DNA. By abrogating a particular cell cycle checkpoint, or inhibiting a particular form of DNA repair, it may therefore be possible to circumvent tumour cell resistance to the genotoxic agents and augment tumour cell death induced by DNA damage, thus increasing the therapeutic index of these cancer treatments.

CHK1 is a serine/threonine kinase involved in regulating cell cycle checkpoint signals that are activated in response to DNA damage and errors in DNA caused by defective replication (see, e.g., Bartek and Lukas, 2003). CHK1 transduces these signals through phosphorylation of substrates involved in a number of cellular activities including cell cycle arrest and DNA repair. Two key substrates of CHK1 are the Cdc25A and Cdc25C phosphatases that dephosphorylate CDK1 leading to its activation, which is a requirement for exit from G2 into mitosis (M phase) (see, e.g., Sanchez et al., 1997). Phosphorylation of Cdc25C and the related Cdc25A by CHK1 blocks their ability to activate CDK1, thus preventing the cell from exiting G2 into M phase. The role of CHK1 in the DNA damage-induced G2 cell cycle checkpoint has been demonstrated in a number of studies where CHK1 function has been knocked out (see, e.g., Liu et al., 2000; Zhao et al., 2002; Zachos et al., 2003).

The reliance of the DNA damage-induced G2 checkpoint upon CHK1 provides one example of a therapeutic strategy for cancer treatment, involving targeted inhibition of CHK1. Upon DNA damage, the p53 tumour suppressor protein is stabilised and activated to give a p53-dependent G1 arrest, leading to apoptosis or DNA repair (Balaint and Vousden, 2001). Over half of all cancers are functionally defective for p53, which can make them resistant to genotoxic cancer treatments such as ionising radiation (IR) and certain forms of chemotherapy (see, e.g., Greenblatt et al., 1994; Carson and Lois, 1995). These p53 deficient cells fail to arrest at the G1 checkpoint or undergo apoptosis or DNA repair, and consequently may be more reliant on the G2 checkpoint for viability and replication fidelity. Therefore abrogation of the G2 checkpoint through inhibition of the CHK1 kinase function may selectively sensitise p53 deficient cancer cells to genotoxic cancer therapies, and this has been demonstrated (see, e.g., Wang et al., 1996; Dixon and Norbury, 2002).

In addition, CHK1 has also been shown to be involved in S phase cell cycle checkpoints and DNA repair by homologous recombination. Thus, inhibition of CHK1 kinase in those cancers that are reliant on these processes after DNA damage, may provide additional therapeutic strategies for the treatment of cancers using CHK1 inhibitors (see, e.g., Sorensen et al., 2005). Furthermore, certain cancers may exhibit replicative stress due to high levels of endogenous DNA damage (see, e.g., Cavalier et al., 2009; Brooks et al., 2012) or through elevated replication driven by oncogenes, for example amplified or overexpressed MYC genes (see, e.g., Di Micco et al. 2006; Cole et al., 2011; Murga et al. 2011). Such cancers may exhibit elevated signalling through CHK1 kinase (see, e.g., Hoglund et al., 2011). Inhibition of CHK1 kinase in those cancers that are reliant on these processes, may provide additional therapeutic strategies for the treatment of cancers using CHK1 inhibitors (see, e.g., Cole et al., 2011; Davies et aL, 2011; Ferrao et al., 2011).

Recent data using CHK1 selective siRNA supports the selective inhibition of CHK1 as a relevant therapeutic approach, and suggests that combined inhibition with certain other checkpoint kinases provides no additional benefit and may be non-productive (see, e.g., Xiao et al., 2006; Guzi et al., 2011). Small-molecule selective inhibitors of CHK1 kinase function from various chemical classes have been described (see, e.g., Tao et al., 2006).

Known Compounds

Collins et al., 2009a, describes certain compounds of the following formula which inhibit Checkpoint Kinase 1 (CHK1) kinase function, and which are useful in the treatment of, e.g., cancer:

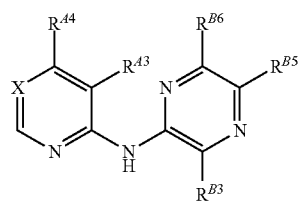

Among the examples in Collins et al., 2009a are the following compounds:

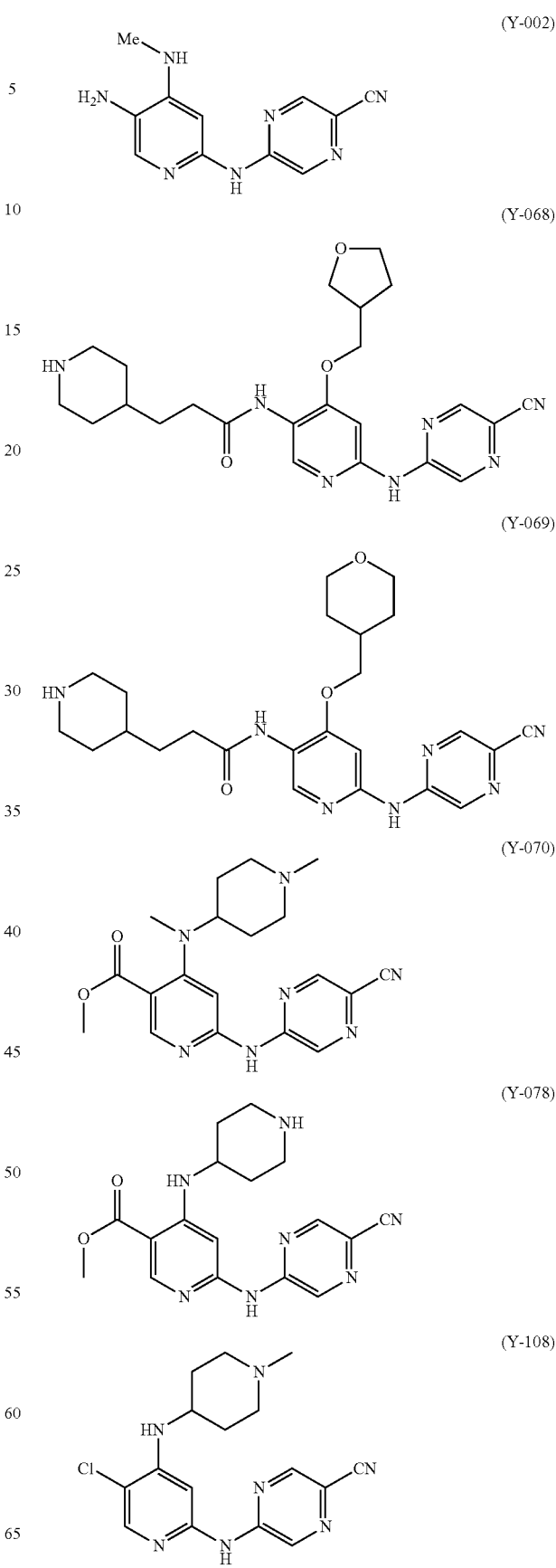

(Y-109)

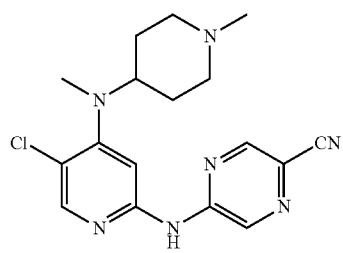

(Z-046)

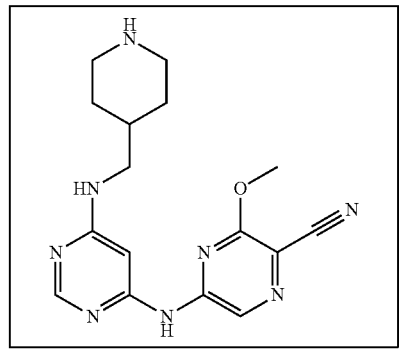

(Y-152)

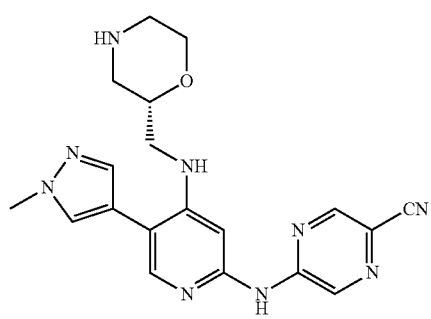

One embodiment in Collins et al., 2009a has —$R^{B6}$ defined as "independently -Me, -Et, -nPr, -iPr, —$CF_3$, —OH, —OMe, —OEt, —O(nPr), —O(iPr), —$OCF_3$, —CN, —$NH_2$, —NHMe, —$NMe_2$, —O—$CH_2CH_2$—OH, —O—$CH_2CH_2$—OMe, —O—$CH_2CH_2$—$NH_2$, —O—$CH_2CH_2$—NHMe, —O—$CH_2CH_2$—$NMe_2$, —O—$CH_2CH_2CH_2$—$NH_2$, —O—$CH_2CH_2CH_2$—NHMe, or —O—$CH_2CH_2CH_2$—$NMe_2$" (see page 48, lines 37-40 and claim 296 therein).

Collins et al., 2009b, describes certain compounds of the following formula which inhibit Checkpoint Kinase 1 (CHK1) kinase function, and which are useful in the treatment of, e.g., cancer:

(Y-153)

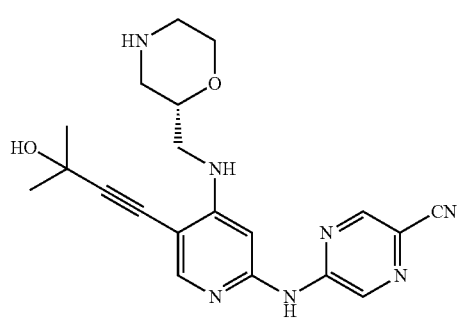

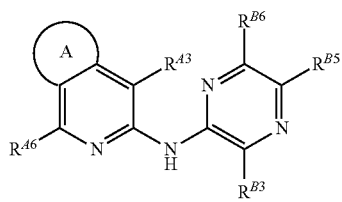

Among the examples in Collins et al., 2009b are the following isoquinoline compounds:

(AA-001)

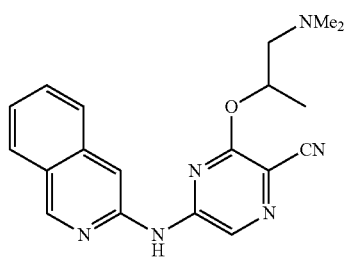

(Y-158)

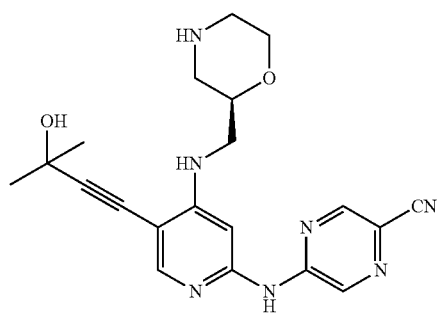

(AA-010)

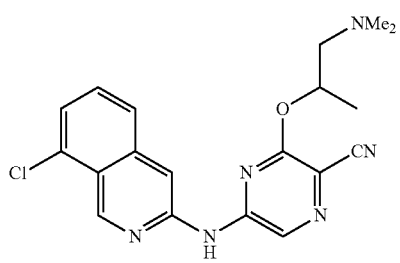

Only one of the examples in Collins et al., 2009a has —$R^{B6}$ as other than —H, specifically, as —OMe, while also having —X= as —N=:

-continued
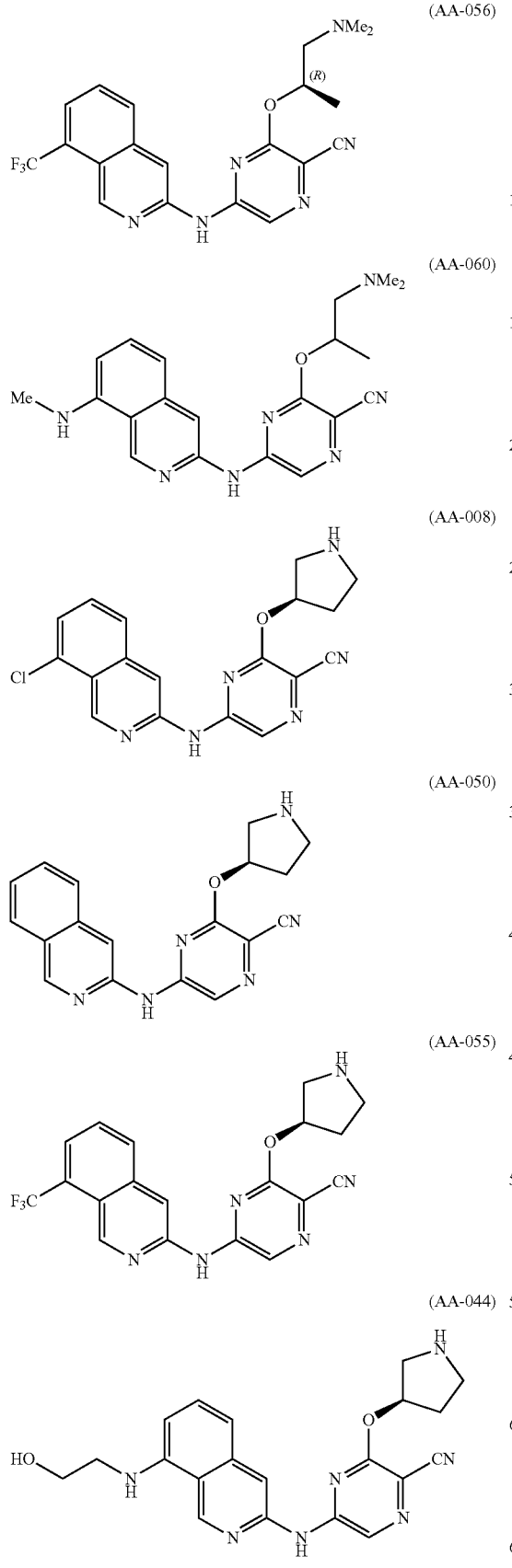
(AA-056)
(AA-060)
(AA-008)
(AA-050)
(AA-055)
(AA-044)
Walton et al., 2010, describes preclinical studies of the CHK1 inhibitor referred as SAR-020106, which has the following structure.
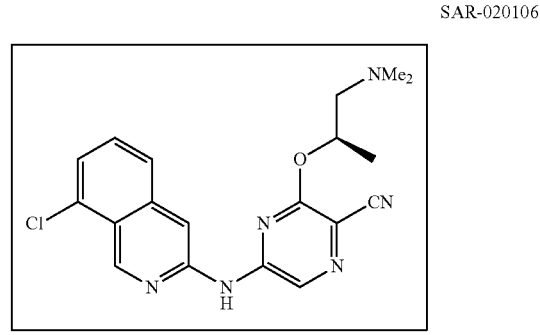 [SMILES: C[C@H](CN(C)C)Oc1nc(Nc2cc3cccc(Cl)c3cn2)cnc1C#N]
SAR-020106
Among the examples in Collins et al., 2009b are the following 1H-imidazo[4,5-b]pyridine compounds:
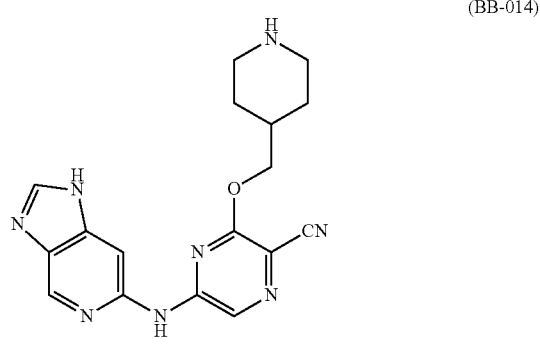
(BB-014)
(BB-024)
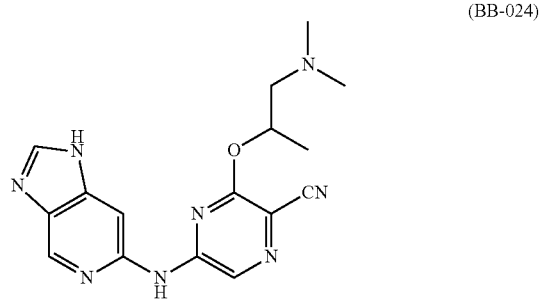
(BB-025)
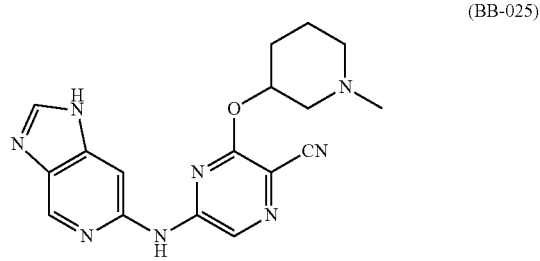

-continued (BB-026)
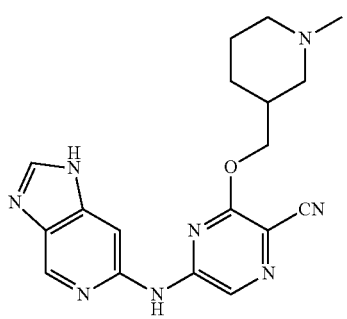

(BB-027)
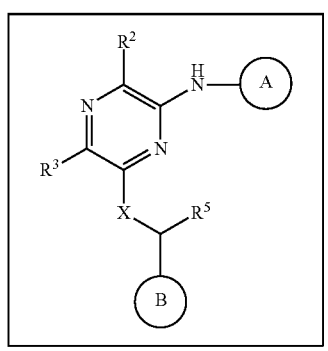

(BB-028)

Almeida et al., 2008, describes certain pyrazolyl-amino-substituted pyrazines of the following formula, which allegedly are useful in the treatment of cancer.

Among the examples in Almeida et al., 2008 are the following compounds:

Example 5
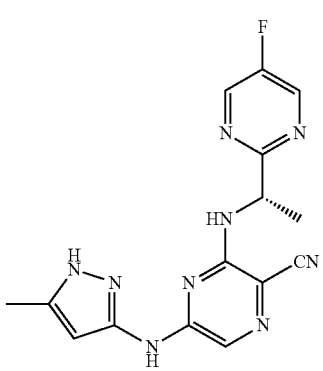

Example 6
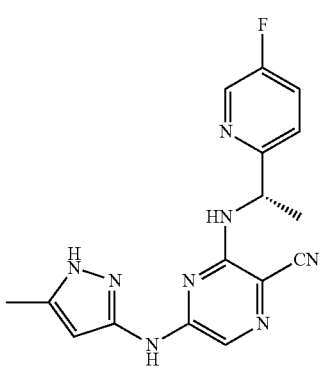

Example 7
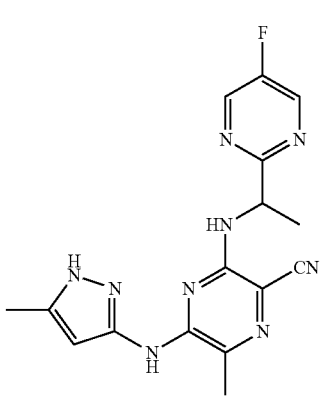

Example 8
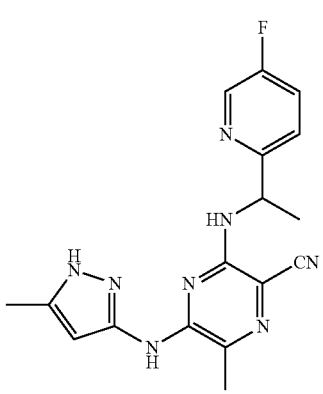

Ioannidis et al., 2009, describes certain compounds which inhibit Janus-associated kinase (JAK). The following compounds are shown in Scheme 5 on page 6526 therein.

Compound 7i

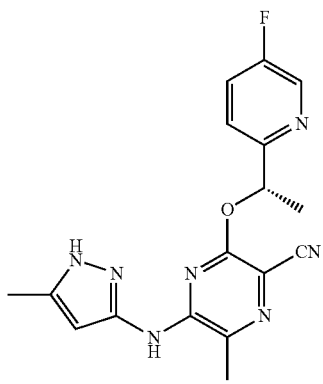

Compound 7j

CCT244747

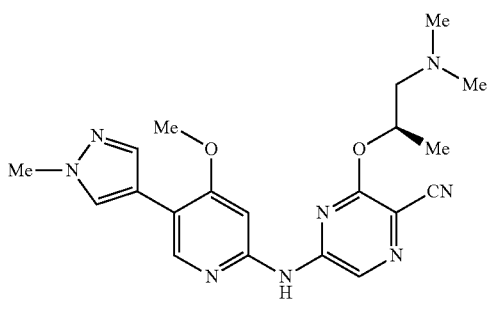

(PAPC-A-01)

Lin et al., 2005, describes certain macrocyclic urea compounds which allegedly are useful as protein kinase inhibitors. See, e.g., paragraph [0004] on page 1 therein.

Tao et al., 2005, describes certain macrocyclic urea compounds which allegedly are useful as protein kinase inhibitors. See, e.g., page 2 therein.

Li et al., 2007, describes the preparation and testing of certain macrocyclic urea CHK1 inhibitors. See, e.g., Table 1 on page 6502 therein.

Tao et al., 2007a, describes the preparation and testing of certain macrocyclic urea CHK1 inhibitors. See, e.g., Table 2 on page 6596 therein.

Tao et al., 2007b, describes the preparation and testing of certain macrocyclic urea CHK1 inhibitors. See, e.g., Table 3 on page 1517 therein.

One or more of the inventors have contributed to recent publications in which a number of CHK1 inhibitors are described, including the following compound, referred to as CCT244747. See, Lainchbury et al., 2012 (apparently published online on 19 Oct. 2012) and Walton et al., 2012 (apparently published 15 Oct. 2012).

SUMMARY OF THE INVENTION

One aspect of the invention pertains to certain pyridyl-amino-pyrazine carbonitrile compounds (referred to herein as PAPC compounds), as described herein.

Another aspect of the invention pertains to a composition (e.g., a pharmaceutical composition) comprising a PAPC compound, as described herein, and a pharmaceutically acceptable carrier or diluent.

In one embodiment, the composition (e.g., a pharmaceutical composition) is suitable for oral administration to a subject.

Another aspect of the invention pertains to a method of preparing a composition (e.g., a pharmaceutical composition) comprising the step of admixing a PAPC compound, as described herein, and a pharmaceutically acceptable carrier or diluent.

Another aspect of the present invention pertains to a method of inhibiting CHK1 kinase function in a cell, in vitro or in vivo, comprising contacting the cell with an effective amount of a PAPC compound, as described herein.

In one embodiment, the method further comprises contacting the cell with one or more other agents selected from: (a) a DNA topoisomerase I or II inhibitor; (b) a DNA damaging agent; (c) an antimetabolite or thymidylate synthase (TS) inhibitor; (d) a microtubule targeted agent; and (e) ionising radiation.

Another aspect of the present invention pertains to a method of regulating (e.g., inhibiting) cell proliferation (e.g., proliferation of a cell), inhibiting cell cycle progression, promoting cell apoptosis, or a combination of one or more these, in vitro or in vivo, comprising contacting a cell with an effective amount of a PAPC compound, as described herein.

In one embodiment, the method further comprises contacting the cell with one or more other agents selected from: (a) a DNA topoisomerase I or II inhibitor; (b) a DNA damaging agent; (c) an antimetabolite or thymidylate synthase (TS) inhibitor; (d) a microtubule targeted agent; and (e) ionising radiation.

Another aspect of the present invention pertains to a method of treatment comprising administering to a subject in need of treatment a therapeutically-effective amount of a PAPC compound, as described herein, preferably in the form of a pharmaceutical composition.

In one embodiment, said administering is orally administering.

In one embodiment, the method further comprises administering to the subject one or more other agents selected from: (a) a DNA topoisomerase I or II inhibitor; (b) a DNA damaging agent; (c) an antimetabolite or thymidylate synthase (TS) inhibitor; (d) a microtubule targeted agent; and (e) ionising radiation.

Another aspect of the present invention pertains to a PAPC compound as described herein for use in a method of treatment of the human or animal body by therapy.

In one embodiment, the compound is for use in a method of treatment of the human or animal body by therapy by oral administration.

In one embodiment, the method of treatment comprises treatment with both (i) a PAPC compound and (ii) one or more other agents selected from: (a) a DNA topoisomerase I or II inhibitor; (b) a DNA damaging agent; (c) an antimetabolite or thymidylate synthase (TS) inhibitor; (d) a microtubule targeted agent; and (e) ionising radiation.

Another aspect of the present invention pertains to use of a PAPC compound, as described herein, in the manufacture of a medicament for use in treatment.

In one embodiment, the medicament is a medicament for oral administration.

In one embodiment, the treatment comprises treatment with both (i) a medicament comprising a PAPC compound and (ii) one or more other agents selected from: (a) a DNA topoisomerase I or II inhibitor; (b) a DNA damaging agent; (c) an antimetabolite or thymidylate synthase (TS) inhibitor; (d) a microtubule targeted agent; and (e) ionising radiation.

In one embodiment, the treatment is treatment of a disease or condition that is mediated by CHK1.

In one embodiment, the treatment is treatment of a disease or condition that is ameliorated by the inhibition of CHK1 kinase function.

In one embodiment, the treatment is treatment of a proliferative condition.

In one embodiment, the treatment is treatment of cancer.

In one embodiment, the treatment is treatment of p53 deficient cancer.

In one embodiment, the treatment is treatment of head cancer; neck cancer; nervous system cancer; brain cancer; neuroblastoma; lung/mediastinum cancer; breast cancer; oesophagus cancer; stomach cancer; liver cancer; biliary tract cancer; pancreatic cancer; small bowel cancer; large bowel cancer; colorectal cancer; gynaecological cancer; genito-urinary cancer; ovarian cancer; thyroid gland cancer; adrenal gland cancer; skin cancer; melanoma; bone sarcoma; soft tissue sarcoma; paediatric malignancy; Hodkin's disease; non-Hodgkin's lymphoma; myeloma; leukaemia; or metastasis from an unknown primary site.

In one embodiment, the treatment is treatment of: lung cancer, breast cancer, ovarian cancer, colorectal cancer, melanoma, glioma, or neuroblastoma.

Another aspect of the present invention pertains to a kit comprising (a) a PAPC compound, as described herein, preferably provided as a pharmaceutical composition and in a suitable container and/or with suitable packaging; and (b) instructions for use, for example, written instructions on how to administer the compound.

In one embodiment, the kit further comprises one or more other agents selected from: (a) a DNA topoisomerase I or II inhibitor; (b) a DNA damaging agent; (c) an antimetabolite or thymidylate synthase (TS) inhibitor; and (d) a microtubule targeted agent.

Another aspect of the present invention pertains to a PAPC compound obtainable by a method of synthesis as described herein, or a method comprising a method of synthesis as described herein.

Another aspect of the present invention pertains to a PAPC compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

Figure 1:
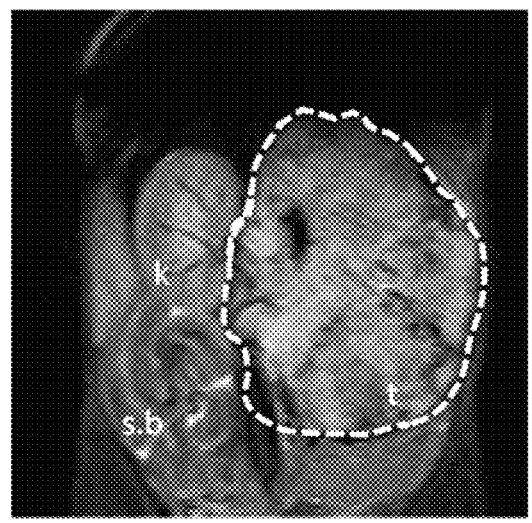
FIG. 1 is an MRI scan recorded as part of the in vivo study ("PAPC-A-01 in Transgenic MYCN-driven Neuroblastoma Model") described below. The image shows the abdomen of a mouse (k=kidney; t=tumour; s.b.=small bowel) and was recorded pre-treatment. The tumour volume was 1960 mm$^3$.

One aspect of the present invention relates to certain compounds that are related to 5-(pyridin-2-yl-amino)-pyrazine-2-carbonitrile:

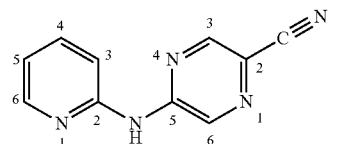

5-(Pyridin-2-yl-amino)-pyrazine-2-carbonitrile

All of the compounds are additionally characterised by a substituent adjacent to the carbonitrile group (at the 3-position of the pyrazine) that is independently:

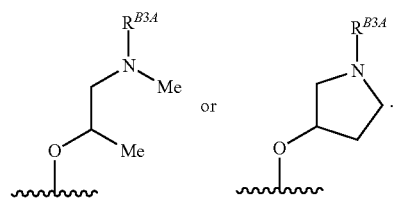

wherein $R^{B3A}$ is as defined herein. These two formulae define groups which may conveniently be described as "open chain" (on the left) and "closed ring" (on the right) analogues of each other, and share the atoms/bonds marked in bold below:

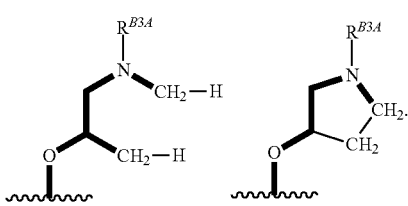

For example, when $R^{B3A}$ is methyl, the compounds are related to the following compounds:

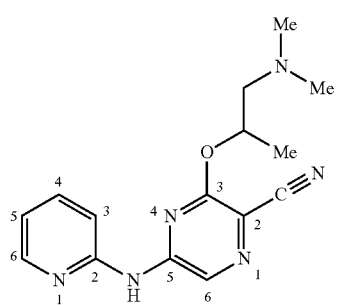

3-(2-Dimethylamino-1-methyl-ethoxy)-
5-(pyridin-2-yl-amino)-pyrazine-2-
carbonitrile

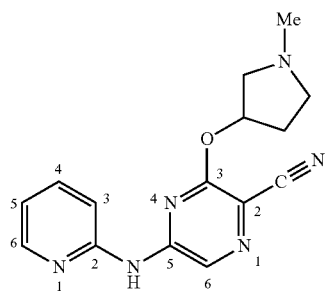

3-(1-Methyl-pyrrolidin-3-yl-oxy)-
5-(pyridin-2-yl-amino)-pyrazine-2-
carbonitrile The compounds of the present invention are potent inhibitors of CHK1 activity (e.g., having a CHK1 $IC_{50}$ of less than 100 nM). The compounds of the present invention may additionally be characterised by (a) notable selectivity as compared to CHK2 (e.g., a CHK1 vs. CHK2 selectivity of at least 100-fold) and/or (b) notable oral bioavailability (e.g., oral bioavailability of at least 100 nM (plasma concentration, 1 hour following 10 mg/kg p.o.)).

Thus, one aspect of the present invention pertains to compounds of the following formula, and pharmaceutically acceptable salts, hydrates, and solvates thereof, wherein —$R^{A4}$—$R^{A5}$, and —$R^{B3}$ are as defined herein (for convenience, collectively referred to herein as "pyridyl-amino-pyrazine carbonitrile compounds" or "PAPC compounds"):

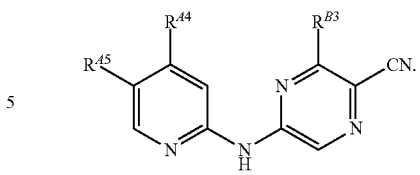

Some embodiments of the invention include the following:
(1) A compound of the following formula, or a pharmaceutically acceptable salt, hydrate, or solvate thereof:

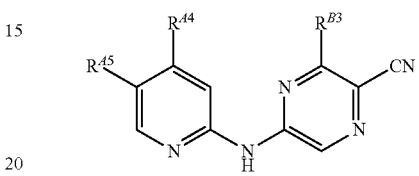

wherein:
—$R^{B3}$ is independently:

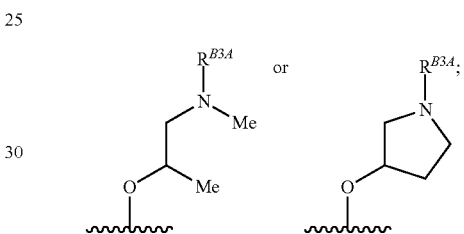

each —$R^{B3A}$ is independently —H or saturated aliphatic $C_{1-3}$alkyl;
—$R^{A4}$ is independently —$NHR^{A4A}$, —$NR^{A4A}{}_2$, or —$OR^{A4A}$;
each —$R^{A4A}$ is independently saturated aliphatic $C_{1-3}$alkyl;
—$R^{A5}$ is independently —$R^{A5A}$, —$R^{A5B}$, —$R^{A5C}$, —$R^{A5D}$, —$R^{A5E}$, or —$R^{A5F}$;
—$R^{A5A}$ is independently:

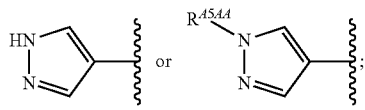

—$R^{A5AA}$ is saturated aliphatic $C_{1-3}$alkyl;
—$R^{A5B}$ is —$CF_3$;
—$R^{A5C}$ is independently —F, —Cl, —Br, or —I;
—$R^{A5D}$ is independently —C≡CH, —C≡C—$R^{A5DA}$, or —C≡C—$R^{A5DB}$—OH;
—$R^{A5DA}$ is saturated aliphatic $C_{1-4}$alkyl;
—$R^{A5DB}$ is saturated aliphatic $C_{1-4}$alkylene;
—$R^{A5E}$ is independently saturated $C_{3-6}$cycloalkyl;
—$R^{A5F}$ is —C(=O)O—$R^{A5FA}$; and
—$R^{A5FA}$ is saturated aliphatic $C_{1-3}$alkyl.

For the avoidance of doubt, it is not intended that any two or more of —$R^{A4}$, —$R^{A5}$, and —$R^{B3}$ together form a ring fused to the ring(s) to which they are attached. For example, it is not intended that —$R^{A4}$ and —$R^{A5}$ together form a ring fused to the ring to which they are attached. Similarly, it is not intended that —$R^{A4}$ and —$R^{B3}$ together form a ring fused to the rings to which they are attached. Similarly, it is not intended that —R$^{A5}$ and —R$^{B3}$ together form a ring fused to the rings to which they are attached.

The group —R$^{B3}$ has one chiral centre, marked by an asterisk in the following formulae, which may independently be in the (R) or (S) configuration. Unless otherwise indicated, it is intended that both configurations are encompassed.

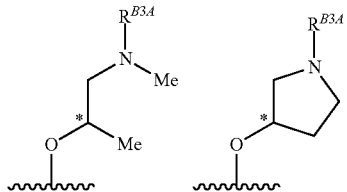

The Group —R$^{B3}$ (2) A compound according to (1), wherein —R$^{B3}$ is:

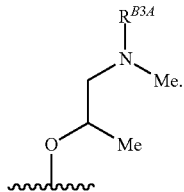

(3) A compound according to (1), wherein —R$^{B3}$ is:

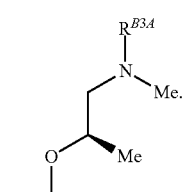

(4) A compound according to (1), wherein —R$^{B3}$ is:

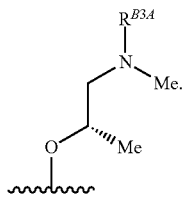

(5) A compound according to (1), wherein —R$^{B3}$ is:

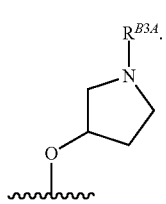

(6) A compound according to (1), wherein —R$^{B3}$ is:

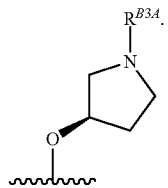

(7) A compound according to (1), wherein —R$^{B3}$ is:

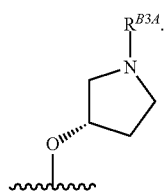

The Group —R$^{B3A}$ (8) A compound according to any one of (1) to (7), wherein —R$^{B3A}$ is saturated aliphatic C$_{1-3}$alkyl.

(9) A compound according to any one of (1) to (7), wherein —R$^{B3A}$ is -Me.

(10) A compound according to any one of (1) to (7), wherein —R$^{B3A}$ is —H.

The Group —R$^{A4}$

(11) A compound according to any one of (1) to (10), wherein —R$^{A4}$ is independently —NHR$^{A4A}$ or —NR$^{A4A}{}_2$.

(12) A compound according to any one of (1) to (10), wherein —R$^{A4}$ is —NHR$^{A4A}$.

(13) A compound according to any one of (1) to (10), wherein —R$^{A4}$ is —NR$^{A4A}{}_2$.

(14) A compound according to any one of (1) to (10), wherein —R$^{A4}$ is —OR$^{A4A}$.

The Group —R$^{A4A}$

(15) A compound according to any one of (1) to (14), wherein each —R$^{A4A}$ is independently -Me or -Et.

(16) A compound according to any one of (1) to (14), wherein each —R$^{A4A}$ is -Me.

The Group —R$^{A5}$

(17) A compound according to any one of (1) to (16), wherein —R$^{A5}$ is —R$^{A5A}$.

(18) A compound according to any one of (1) to (16), wherein —R$^{A5}$ is —R$^{A5B}$.

(19) A compound according to any one of (1) to (16), wherein —R$^{A5}$ is —R$^{A5C}$.

(20) A compound according to any one of (1) to (16), wherein —R$^{A5}$ is —R$^{A5D}$.

(21) A compound according to any one of (1) to (16), wherein —R$^{A5}$ is —R$^{A5E}$.

(22) A compound according to any one of (1) to (16), wherein —R$^{A5}$ is —R$^{A5F}$.

The Group —R$^{A5A}$

(23) A compound according to any one of (1) to (22), wherein —R$^{A5A}$, if present, is:

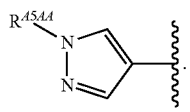

(24) A compound according to any one of (1) to (22), wherein —R$^{A5A}$, if present, is:

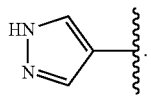

The Group —R^{A5AA}

(25) A compound according to any one of (1) to (24), wherein each —R^{A5AA}, if present, is -Me or -Et.
(26) A compound according to any one of (1) to (24), wherein each —R^{A5AA}, if present, is -Me.
(27) A compound according to any one of (1) to (24), wherein each —R^{A5AA}, if present, is -Et.

The Group —R^{A5C}

(28) A compound according to any one of (1) to (27), wherein —R^{5C}, if present, is independently —F, —Cl, or —Br.
(29) A compound according to any one of (1) to (27), wherein —R^{5C}, if present, is independently —F.
(30) A compound according to any one of (1) to (27), wherein —R^{A5D}, if present, is independently —Cl.
(31) A compound according to any one of (1) to (27), wherein —R^{A5D}, if present, is independently —Br.
(32) A compound according to any one of (1) to (27), wherein —R^{A5D}, if present, is independently —I.

The Group —R^{A5D}

(33) A compound according to any one of (1) to (32), wherein —R^{A5D}, if present, is independently —C≡CH or —C≡C—R^{A5DA}.
(34) A compound according to any one of (1) to (32), wherein —R^{A5D}, if present, is —C≡CH.
(35) A compound according to any one of (1) to (32), wherein —R^{A5D}, if present, is —C≡C—R^{A5DA}.
(36) A compound according to any one of (1) to (32), wherein —R^{A5D}, if present, is —C≡C—R^{A5DB}—OH.

The Group —R^{A5DA}

(37) A compound according to any one of (1) to (36), wherein —R^{A5DA}, if present, is independently -Me, -Et, —CH(Me)_2, or —C(Me)_3.
(38) A compound according to any one of (1) to (36), wherein —R^{A5DA}, if present, is —CH(Me)_2.
(39) A compound according to any one of (1) to (36), wherein —R^{A5DA}, if present, is —C(Me)_3.

The Group —R^{A5DB}—

(40) A compound according to any one of (1) to (39), wherein —R^{A5DB}—, if present, is saturated aliphatic C_{1-3}alkylene.
(41) A compound according to any one of (1) to (39), wherein —R^{A5DB}—, if present, is independently —CH_2—, —CH(Me)-, or —C(Me)_2-.
(42) A compound according to any one of (1) to (39), wherein —R^{A5DB}—, if present, is —C(Me)_2-.
(43) A compound according to any one of (1) to (39), wherein —R^{A5DB}—, if present, is —CH(Me)-.
(44) A compound according to any one of (1) to (39), wherein —R^{A5DB}—, if present, is The Group —R^{A5E}

(45) A compound according to any one of (1) to (44), wherein —R^{A5E}, if present, is independently cyclopropyl, cyclobutyl, or cyclopentyl.
(46) A compound according to any one of (1) to (44), wherein —R^{A5E}, if present, is independently cyclopropyl or cyclobutyl.

(47) A compound according to any one of (1) to (44), wherein —R^{A5E}, if present, is cyclopropyl.

The Group —R^{A5FA}

(48) A compound according to any one of (1) to (47), wherein —R^{A5FA}, if present, is -Me or -Et.
(49) A compound according to any one of (1) to (47), wherein —R^{A5FA}, if present, is -Me.
(50) A compound according to any one of (1) to (47), wherein —R^{A5FA}, if present, is -Et.

Some Preferred Combinations

(51) A compound according to (1), which is a compound of the following formula, or a pharmaceutically acceptable salt, hydrate, or solvate thereof:

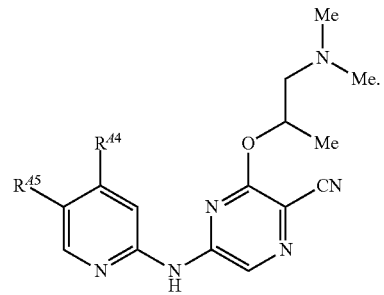

(52) A compound according to (1), which is a compound of the following formula, or a pharmaceutically acceptable salt, hydrate, or solvate thereof:

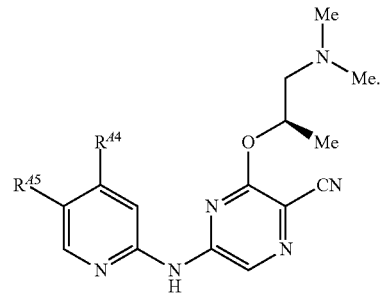

(53) A compound according to (1), which is a compound of the following formula, or a pharmaceutically acceptable salt, hydrate, or solvate thereof:

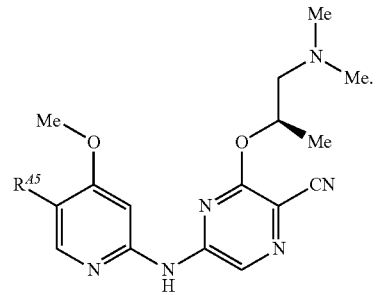

(54) A compound according to (1), which is a compound of one of the following formulae, or a pharmaceutically acceptable salt, hydrate, or solvate thereof:

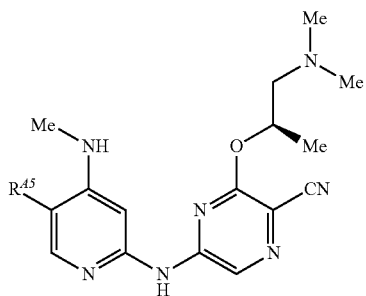

and

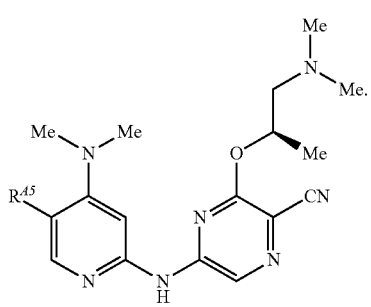

(55) A compound according to (1), which is a compound of the following formula, or a pharmaceutically acceptable salt, hydrate, or solvate thereof:

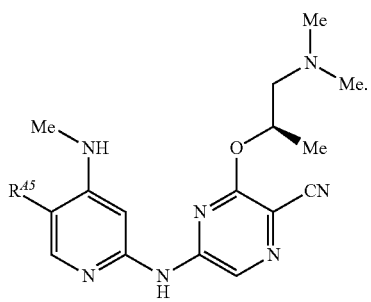

(56) A compound according to (1), which is a compound of the following formula, or a pharmaceutically acceptable salt, hydrate, or solvate thereof:

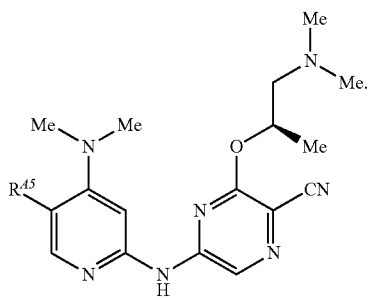

(57) A compound according to (1), which is a compound of the following formula, or a pharmaceutically acceptable salt, hydrate, or solvate thereof:

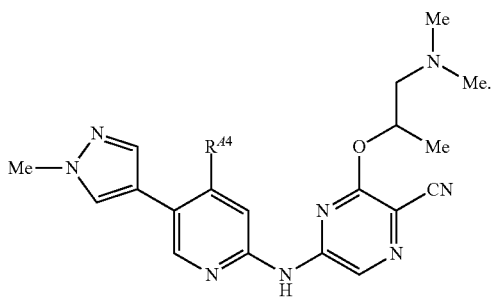

(58) A compound according to (1), which is a compound of the following formula, or a pharmaceutically acceptable salt, hydrate, or solvate thereof:

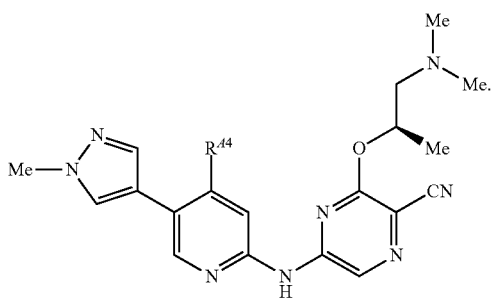

(59) A compound according to (1), which is a compound of one of the following formulae, or a pharmaceutically acceptable salt, hydrate, or solvate thereof:

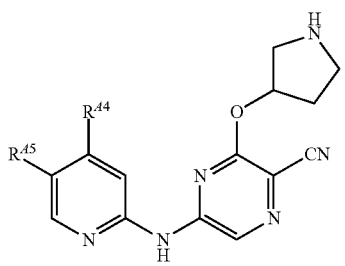

and

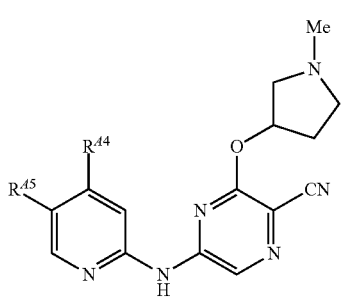

(60) A compound according to (1), which is a compound of one of the following formulae, or a pharmaceutically acceptable salt, hydrate, or solvate thereof:

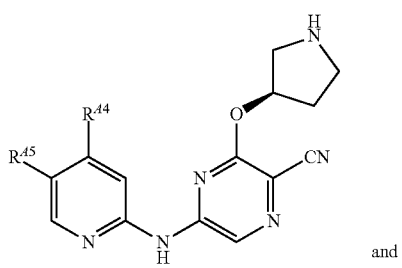

and

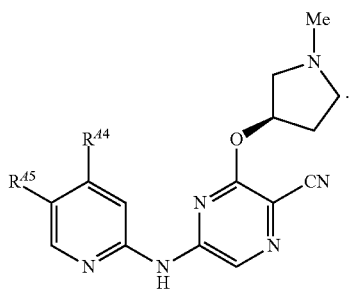

(61) A compound according to (1), which is a compound of one of the following formulae, or a pharmaceutically acceptable salt, hydrate, or solvate thereof:

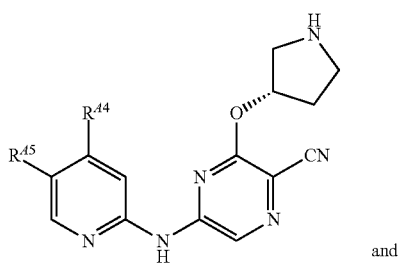

and

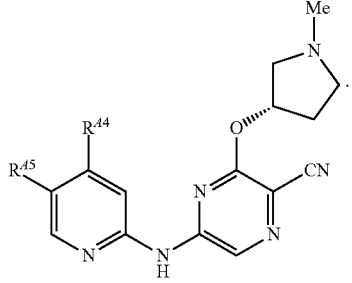

(62) A compound according to (1), which is a compound of one of the following formulae, or a pharmaceutically acceptable salt, hydrate, or solvate thereof:

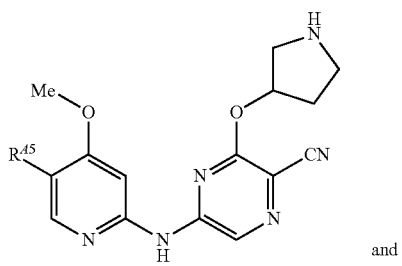

and

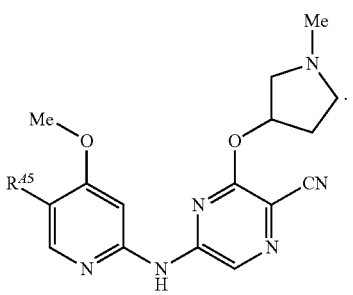

(63) A compound according to (1), which is a compound of one of the following formulae, or a pharmaceutically acceptable salt, hydrate, or solvate thereof:

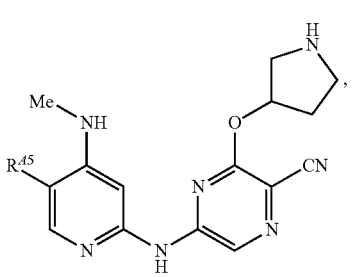

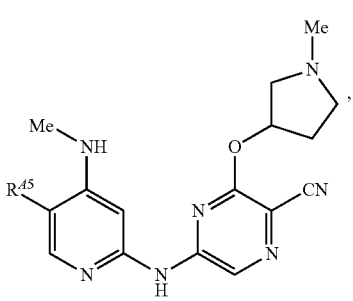

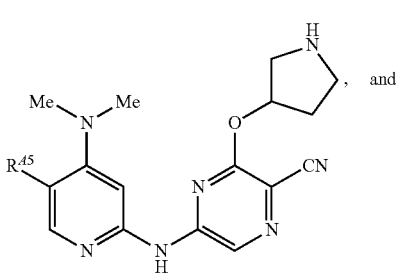

and

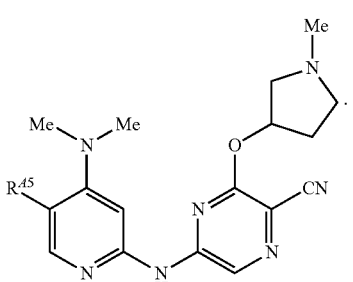

(64) A compound according to (1), which is a compound of one of the following formulae, or a pharmaceutically acceptable salt, hydrate, or solvate thereof:

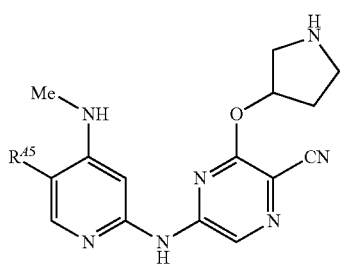

and

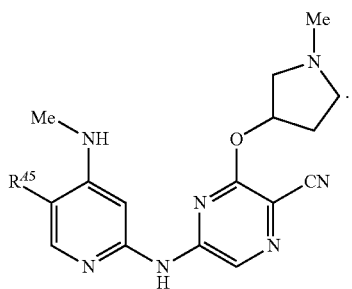

(65) A compound according to (1), which is a compound of one of the following formulae, or a pharmaceutically acceptable salt, hydrate, or solvate thereof:

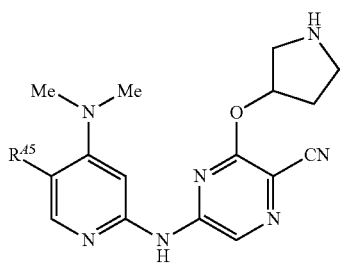

and

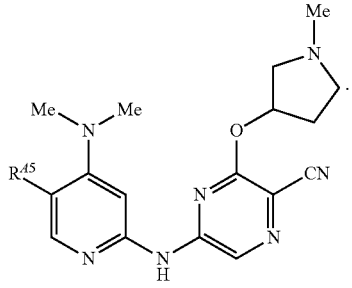

(66) A compound according to (1), which is a compound of one of the following formulae, or a pharmaceutically acceptable salt, hydrate, or solvate thereof:

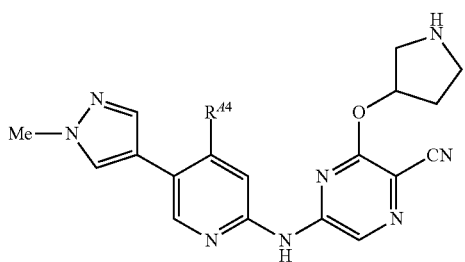

and

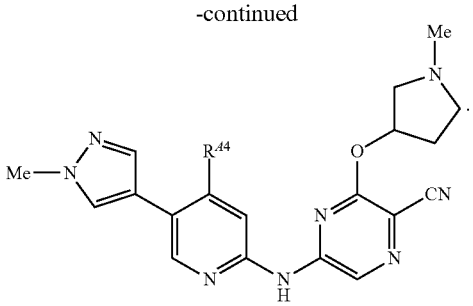

(67) A compound according to (1), which is a compound of one of the following formulae, or a pharmaceutically acceptable salt, hydrate, or solvate thereof:

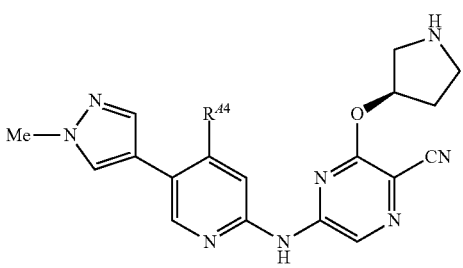

and

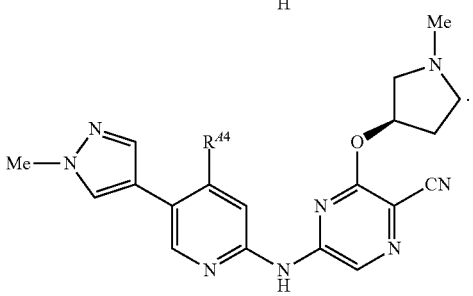

(68) A compound according to (1), which is a compound of one of the following formulae, or a pharmaceutically acceptable salt, hydrate, or solvate thereof:

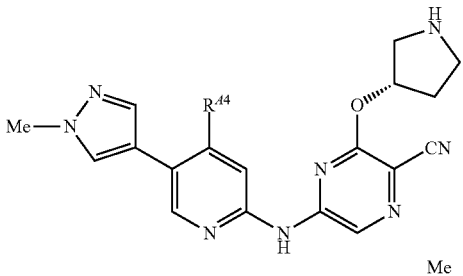

and

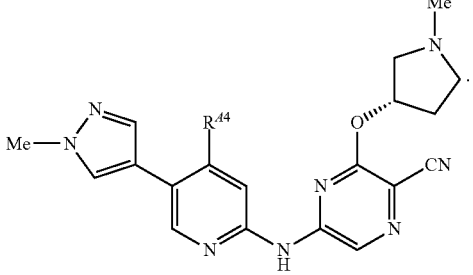

Specific Compounds

(69) A compound according to (1), which is a compound one of the following formulae, or a pharmaceutically acceptable salt, hydrate, or solvate thereof:

| Code No. | Structure |
|---|---|
| PAPC-A-01 | 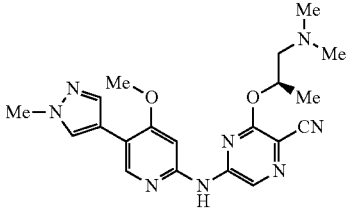 [SMILES: COc1cc(Nc2cnc(C#N)c(O[C@H](C)CN(C)C)n2)ncc1-c1cnn(C)c1] |
| PAPC-A-02 | 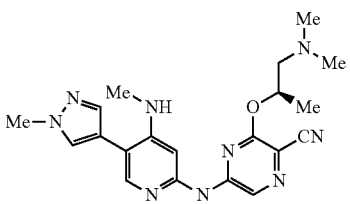 |
| PAPC-A-03 | 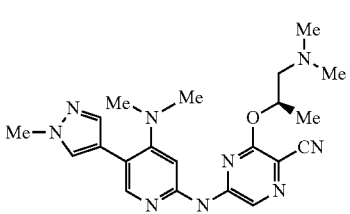 |
| PAPC-A-04 | 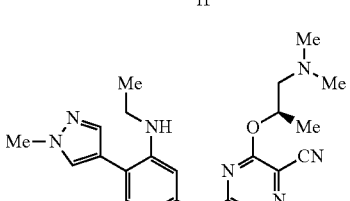 |
| PAPC-A-05 | 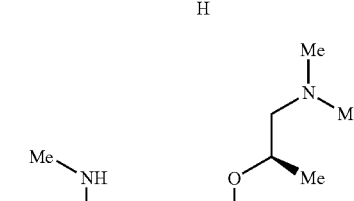 |
| PAPC-A-06 | 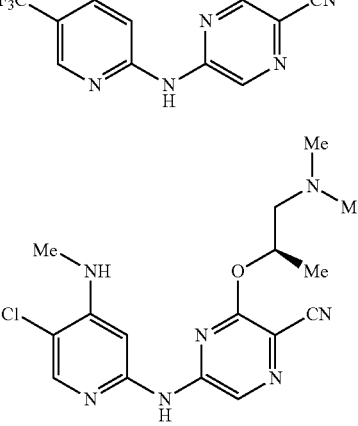 |
| PAPC-A-07 | 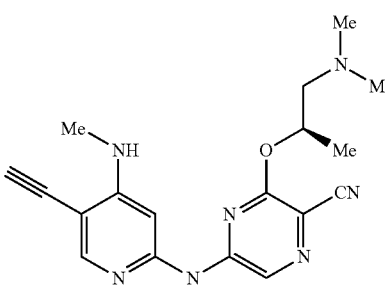 |
| PAPC-A-08 | 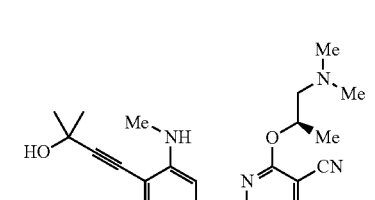 |
| PAPC-A-09 | 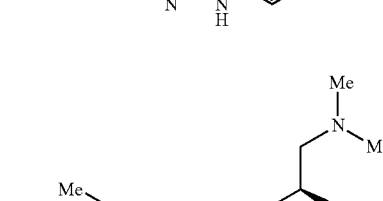 |
| PAPC-A-10 | 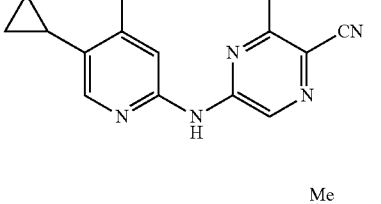 |

(70) A compound according to (1), which is a compound one of the following formulae, or a pharmaceutically acceptable salt, hydrate, or solvate thereof:

| Code No. | Structure |
|---|---|
| PAPC-B-01 | 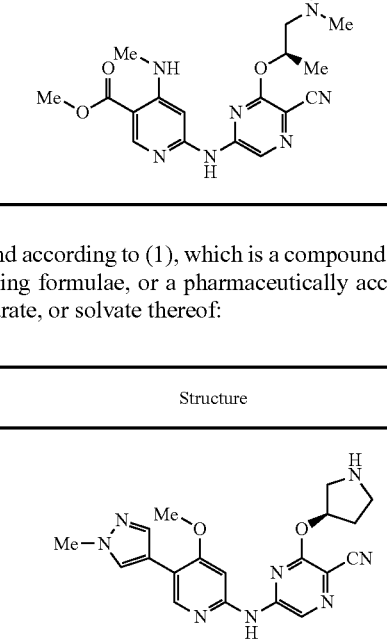 |

-continued

| Code No. | Structure |
|---|---|
| PAPC-B-02 | 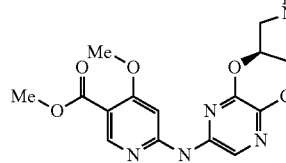 |
| PAPC-B-03 | 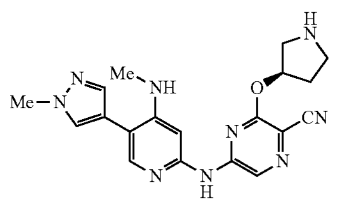 [SMILES: CNc1cc(Nc2cnc(C#N)c(O[C@@H]3CCNC3)n2)ncc1-c1cnn(C)c1] |
| PAPC-B-04 | 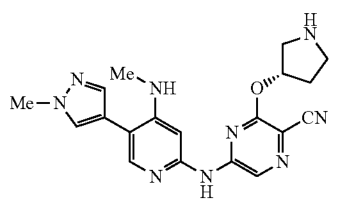 [SMILES: CNc1cc(Nc2cnc(C#N)c(O[C@H]3CCNC3)n2)ncc1-c1cnn(C)c1] |
| PAPC-B-05 | 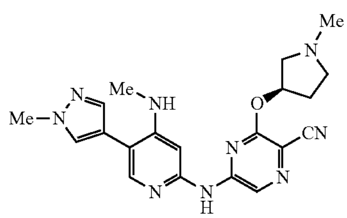 [SMILES: CNc1cc(Nc2cnc(C#N)c(O[C@@H]3CCN(C)C3)n2)ncc1-c1cnn(C)c1] |
| PAPC-B-06 | 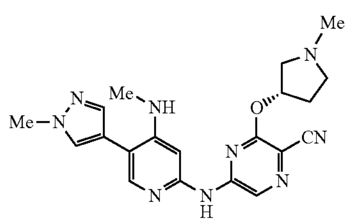 [SMILES: CNc1cc(Nc2cnc(C#N)c(O[C@H]3CCN(C)C3)n2)ncc1-c1cnn(C)c1] |
| PAPC-B-07 | 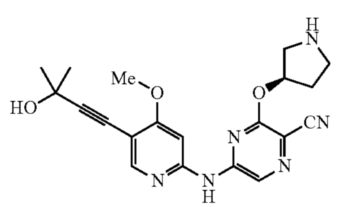 [SMILES: COc1cc(Nc2cnc(C#N)c(O[C@@H]3CCNC3)n2)ncc1C#CC(C)(C)O] |
| PAPC-B-08 | 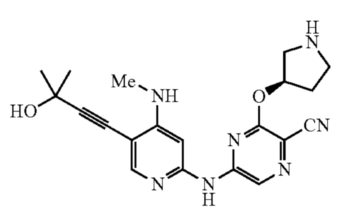 [SMILES: CNc1cc(Nc2cnc(C#N)c(O[C@@H]3CCNC3)n2)ncc1C#CC(C)(C)O] |

-continued

| Code No. | Structure |
|---|---|
| PAPC-B-09 | 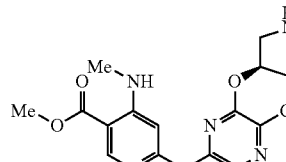 |
| PAPC-B-10 | 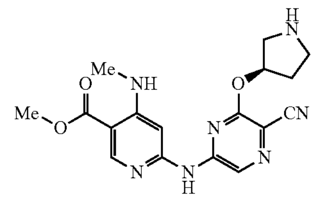 [SMILES: CNc1cc(Nc2cnc(C#N)c(O[C@@H]3CCNC3)n2)ncc1C(=O)OC] |
| PAPC-B-11 | 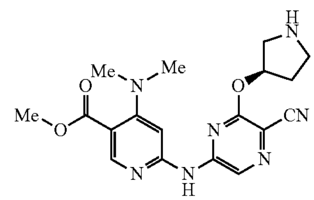 [SMILES: COC(=O)c1cnc(Nc2cnc(C#N)c(O[C@@H]3CCNC3)n2)cc1N(C)C] |

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., $-R^{B3}$, $-R^{B3A}$, $-R^{A4}$, $-R^{A4A}$, $-R^{A5}$, $-R^{A5A}$, $-R^{A5AA}$, $-R^{A5B}$, $-R^{A5C}$, $-R^{A5D}$, $-R^{A5DA}$, $-R^{A5DB}$, $-R^{A5E}$, $-R^{A5F}$, $-R^{A5FA}$ etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to PAPC compounds, in purified form.

In one embodiment, the compound is in substantially purified form and/or in a form substantially free from contaminants.

In one embodiment, the compound is in a substantially purified form with a purity of least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the compound is in a substantially purified form with an optical purity of at least 60% (i.e., 60% of the compound, on a molar basis, is the desired stereoisomer or enantiomer, and 40% is undesired stereoisomer(s) or enantiomer), e.g., at least 70%, e.g., at least 80%, e.g., at least 90%, e.g., at least 95%, e.g., at least 97%, e.g., at least 98%, e.g., at least 99%.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-3}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

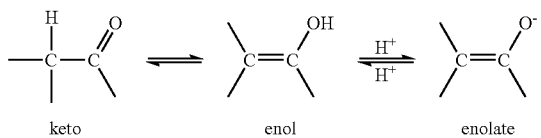

keto      enol      enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetoxybenzoic, acetic, ascorbic, aspartic, benzoic, camphorsulfonic, cinnamic, citric, edetic, ethanedisulfonic, ethanesulfonic, formic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Hydrates and Solvates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a hemi-hydrate, a mono-hydrate, a sesqui-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Greene and P. Wuts; 4th Edition; John Wiley and Sons, 2006).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl(diphenylmethyl), or trityl(triphenylmethyl) ether; a trimethylsilyl or t-butyldimethylsilyl ether; or an acetyl ester (—OC(=O)CH$_3$, —OAc).

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH—Teoc), as a 2,2,2-trichloroethyloxy amide (—NH-Troc), as an allyloxy amide (—NH—Alloc), as a 2(-phenylsulfonyl)ethyloxy amide (—NH—Psec); or, in suitable cases (e.g., cyclic amines), as a nitroxide radical (>N—O●).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

General Chemical Synthesis

Several methods for the chemical synthesis of PAPC compounds are described herein. These and/or other well known methods may be modified and/or adapted in known ways in order to facilitate the synthesis of additional compounds described herein.

Chemical Synthesis

Several methods for the chemical synthesis of pyridyl-amino-pyrazine carbonitrile (PAPC) compounds of the present invention are described herein. These and/or other well known methods may be modified and/or adapted in known ways in order to facilitate the synthesis of additional compounds within the scope of the present invention.

In one approach (General Method A), compounds of type (v) are prepared by a method as illustrated in the following scheme. Commercially available compound (i) is reacted with a source of ammonia, typically in aqueous solution with heating, to give aminopyrazine (ii). Subsequent reaction with a brominating agent, such as N-bromosuccinimide at 0° C., gives the bromopyrazine (iii). Subsequent reaction of the bromopyrazine with a cyanide source, typically potassium cyanide, under palladium mediated coupling conditions, gives the pyrazine carbonitrile (iv). Subsequent reaction with an alcohol, typically in an aprotic solvent such as dioxane in the presence of a base such as sodium hydride, typically with heating, gives the required 6-alkoxy-substituted-2-aminopyrazine-5-carbonitriles (v).

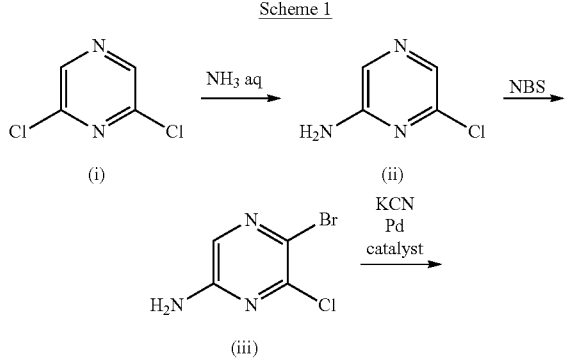

-continued

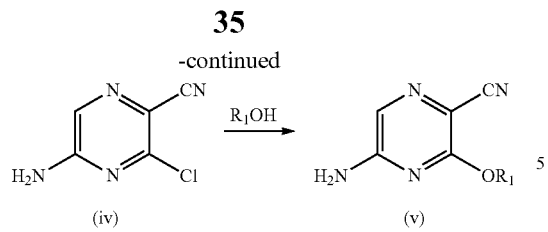

(iv) → (v)

In another approach (General Method B), compounds of type (viii) are prepared by a method as illustrated in the following scheme. Commercially available compound (vi) is reacted with an aldehyde (vii), for example paraformaldehyde, under reductive amination conditions using a reducing agent, for example sodium triacetoxyborohydride, typically with heating and in the presence of an acid, to give the required compounds (viii).

Scheme 2

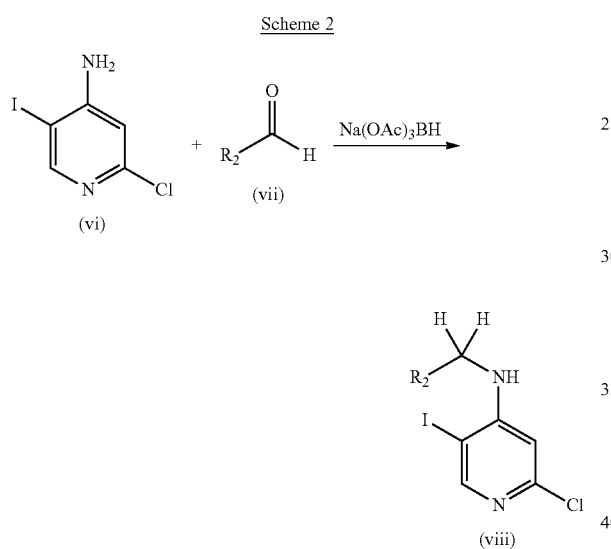

In another approach (General Method C), compounds of type (x) are prepared by a method as illustrated in the following scheme. Compounds (ix) are reacted with an iodinating agent, typically N-iodosuccinimide in sulphuric acid, to afford the required compounds (x).

Scheme 3

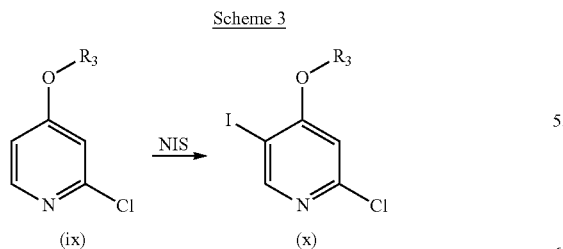

In another approach (General Method D), compounds of type (xii) are prepared by a method as illustrated in the following scheme. Compounds (xi) are reacted with a chlorinating agent, typically N-chlorosuccinimide in acetic acid, to afford the required compounds (xii).

Scheme 4

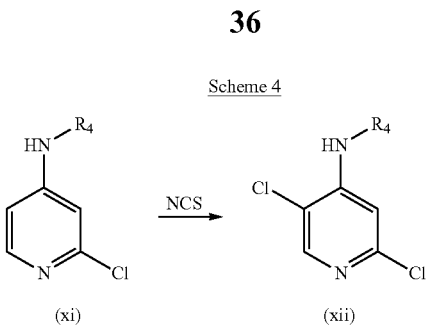

In another approach (General Method E), compounds of type (xv) are prepared by a method as illustrated in the following scheme. Commercially available compound (xiii) is reacted with an amine (xiv), for example methylamine, typically with heating in a microwave reactor, to afford the required compounds (xv).

Scheme 5

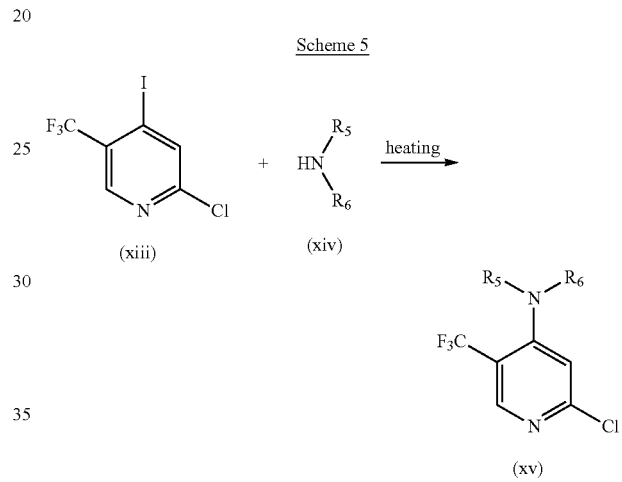

In another approach (General Method F), compounds of type (xvii) are prepared by a method as illustrated in the following scheme. Compounds (xvi) are reacted with an amine (xiv), for example dimethylamine, typically in acetonitrile at room temperature or below, to afford the required compounds (xvii).

Scheme 6

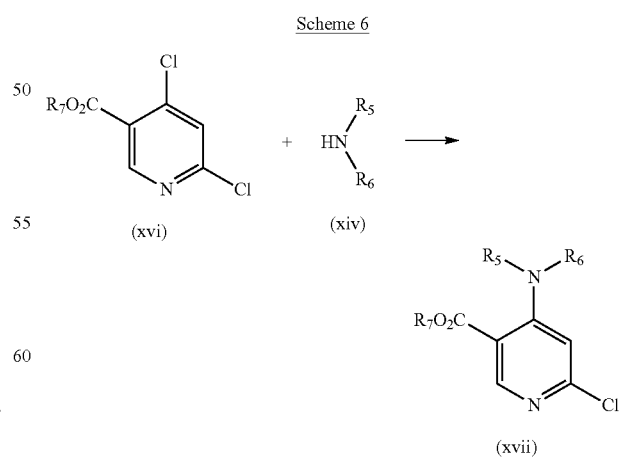

In another approach (General Method G), compounds of type (xix) are prepared by a method as illustrated in the following scheme. Compounds (xvi) are reacted with an alkoxide salt (xviii), for example sodium methoxide, in an aprotic solvent such as tetrahydrofuran at room temperature, to afford the required compounds (xix).

ladium mediated amination conditions, typically with microwave or oil bath heating and in the presence of a base, such as a metal carbonate, gives, after removal of any protecting groups, the required PAPC compounds (xxv).

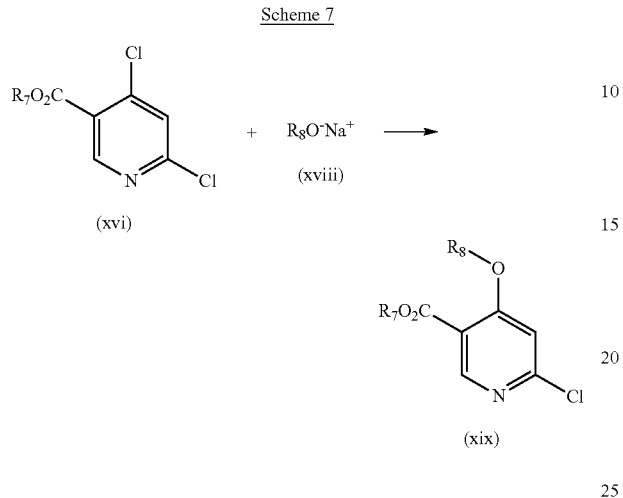

Scheme 7

In another approach (General Method H), compounds of type (xxii) are prepared by a method as illustrated in the following scheme. Compounds (xx) are reacted with haloalkanes (xxi), for example iodomethane, typically in an aprotic solvent such as DMF and in the presence of a base, such as sodium hydride, to afford the required compounds (xxii).

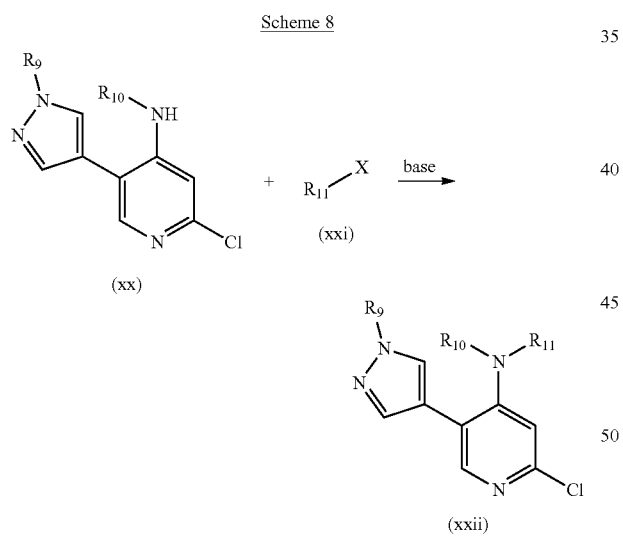

Scheme 8

In another approach (General Method I), compounds of type (xxv) are prepared by a method as illustrated in the following scheme. 5-Iodo-2-chloropyridines (viii) or (x) are coupled with boronic acids or esters (xxiii), for example 1-methyl 4-(4,4,5,5-tetramethyl-1,3,2-dioxaborolan-2-yl)-1H-pyrazole or 2-cyclopropyl-4,4,5,5-tetramethyl-1,3,2-dioxaborolane, under palladium mediated coupling conditions in a solvent such as acetonitrile, typically with oil bath or microwave heating, and typically in the presence of a metal carbonate base, to provide pyridines (xxiv). Treatment of intermediates (xxiv) with pyrazine compounds (v) under pal-

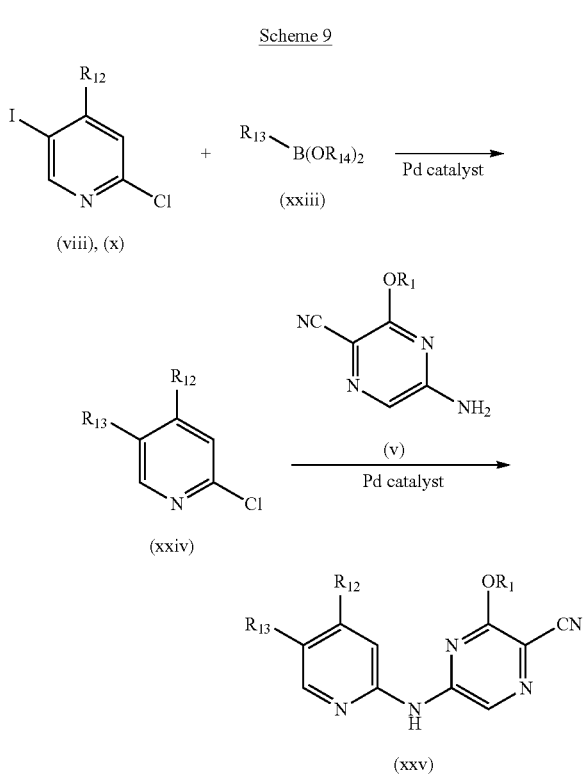

Scheme 9

In another approach (General Method J), compounds of type (xxvi) are prepared by a method as illustrated in the following scheme. 2-Chloropyridine-5-carboxylate esters (xvii) or (xix), are coupled with pyrazine compounds (v) under palladium mediated amination conditions, typically with microwave or oil bath heating and in the presence of a base, such as a metal carbonate, to give, after removal of any protecting groups, the required PAPC compounds (xxvi).

Scheme 10

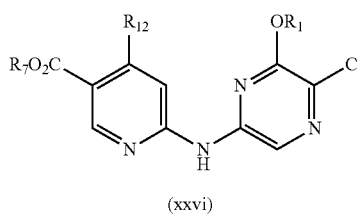

(xxvi)

In another approach (General Method K), compounds of type (xxvii) are prepared by a method as illustrated in the following scheme. 2,5-Dichloropyridines (xii) are coupled with pyrazine compounds (v) under palladium mediated amination conditions, typically with microwave or oil bath heating and in the presence of a base, such as a metal carbonate, to give, after removal of any protecting groups, the required PAPC compounds (xxvii).

Scheme 11

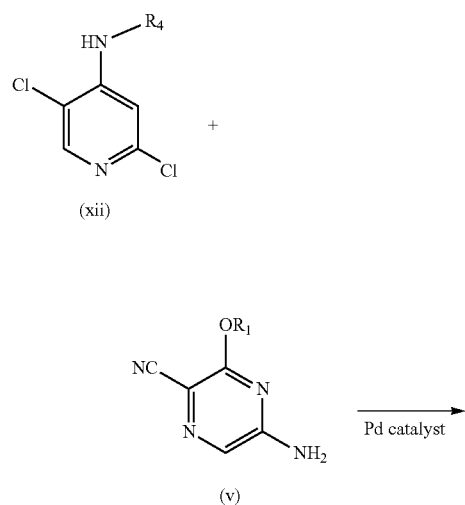

In another approach (General Method L), compounds of type (xxviii) are prepared by a method as illustrated in the following scheme. 5-Trifluoromethyl-2-chloropyridines (xv) are coupled with pyrazine compounds (v) under palladium mediated amination conditions, typically with microwave or oil bath heating and in the presence of a base, such as a metal carbonate, to give, after removal of any protecting groups, the required PAPC compounds (xxviii).

Scheme 12

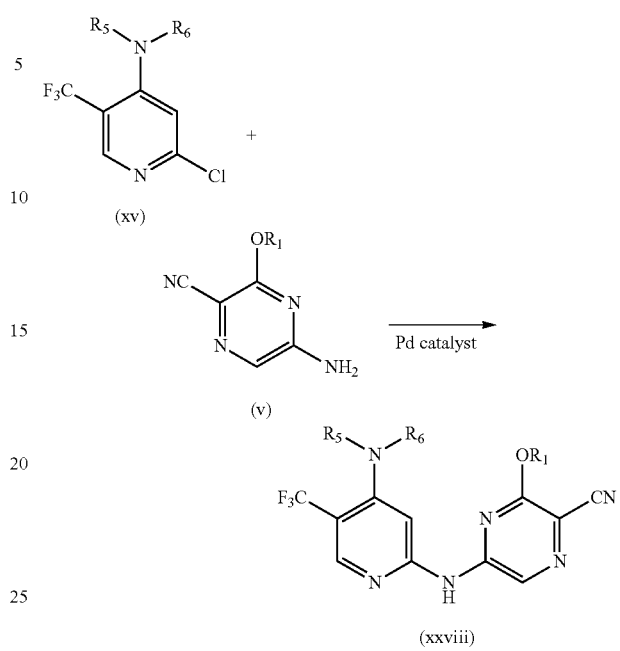

In another approach (General Method M), compounds of type (xxxi) are prepared by a method as illustrated in the following scheme. 5-Iodo-2-chloropyridines (viii) or (x) are coupled with alkynes (xxix), for example ethynyltrimethylsilane or trimethyl(2-methylbut-3-yn-2-yloxy)silane under palladium mediated coupling conditions in the presence of a copper (I) salt, for example copper (I) iodide, in a solvent such as DMF typically with oil bath or microwave heating, and typically in the presence of a base, to provide pyridines (xxx). Treatment of intermediates (xxx) with pyrazine compounds (v) under palladium mediated amination conditions, typically with microwave or oil bath heating and in the presence of a base, such as a metal carbonate, gives, after removal of any protecting groups, the required PAPC compounds (xxxi).

Scheme 13

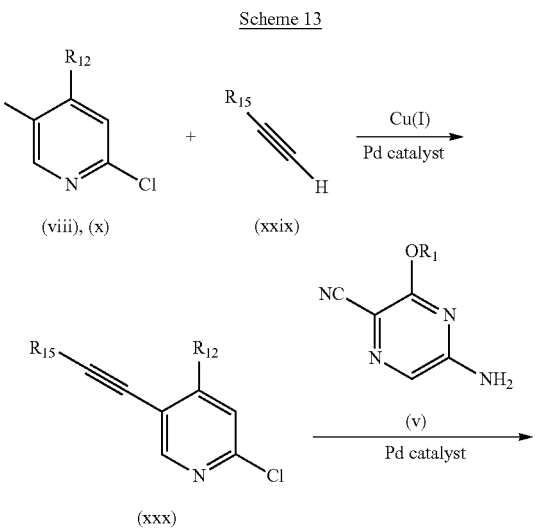

-continued

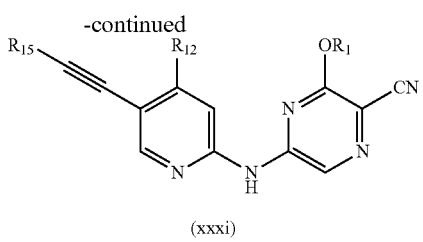

(xxxi)

In another approach (General Method N), compounds of type (xxxii) are prepared by a method as illustrated in the following scheme. 5-(Pyrazol-4-yl)-2-chloropyridines (xxii), are coupled with pyrazine compounds (v) under palladium mediated amination conditions, typically with microwave or oil bath heating and in the presence of a base, such as a metal carbonate, to give, after removal of any protecting groups, the required PAPC compounds (xxxii).

Scheme 14

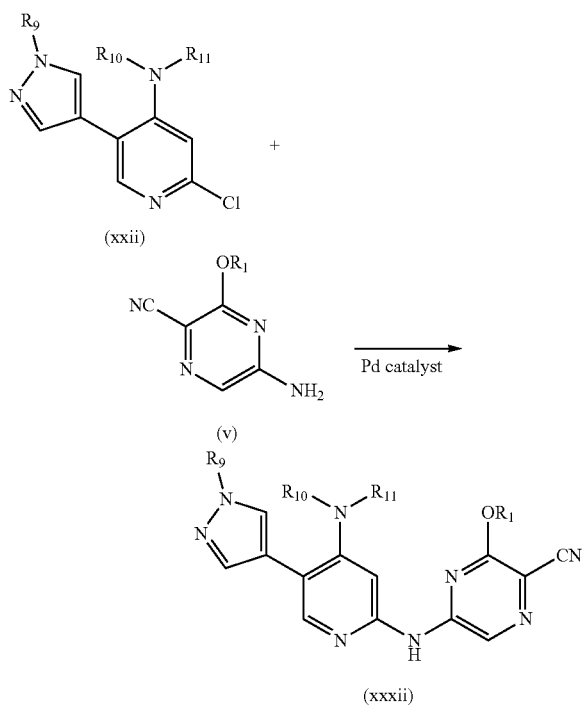

Compositions

One aspect of the present invention pertains to a composition (e.g., a pharmaceutical composition) comprising a PAPC compound, as described herein, and a pharmaceutically acceptable carrier, diluent, or excipient.

Another aspect of the present invention pertains to a method of preparing a composition (e.g., a pharmaceutical composition) comprising admixing a PAPC compound, as described herein, and a pharmaceutically acceptable carrier, diluent, or excipient.

In one preferred embodiment, the composition (e.g., a pharmaceutical composition) is suitable for oral adminstration to a subject.

Uses

The PAPC compounds, as described herein, are useful, for example, in the treatment of disorders (e.g., diseases) that are ameliorated by the inhibition of CHK1 kinase function, as described herein.

Use in Methods of Inhibiting CHK1

One aspect of the present invention pertains to a method of inhibiting CHK1 kinase function, in vitro or in vivo, comprising contacting a CHK1 kinase with an effective amount of a PAPC compound, as described herein.

One aspect of the present invention pertains to a method of inhibiting CHK1 kinase function in a cell, in vitro or in vivo, comprising contacting the cell with an effective amount of a PAPC compound, as described herein.

In one embodiment, the method further comprises contacting the cell with one or more other agents selected from: (a) a DNA topoisomerase I or II inhibitor; (b) a DNA damaging agent; (c) an antimetabolite or thymidylate synthase (TS) inhibitor; (d) a microtubule targeted agent; and (e) ionising radiation.

Suitable assays for determining CHK1 kinase function inhibition are described herein and/or are known in the art.

In one embodiment, the method is performed in vitro.

In one embodiment, the method is performed in vivo.

In one embodiment, the PAPC compound is provided in the form of a pharmaceutically acceptable composition.

Any type of cell may be treated, including but not limited to, adipose, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound inhibits CHK1 kinase function. For example, suitable assays are described herein.

Use in Methods of Inhibiting Cell Proliferation, Etc.

The PAPC compounds described herein, e.g., (a) regulate (e.g., inhibit) cell proliferation; (b) inhibit cell cycle progression; (c) promote cell apoptosis; or (d) a combination of one or more of these.

One aspect of the present invention pertains to a method of regulating (e.g., inhibiting) cell proliferation (e.g., proliferation of a cell), inhibiting cell cycle progression, promoting cell apoptosis, or a combination of one or more these, in vitro or in vivo, comprising contacting a cell with an effective amount of a PAPC compound, as described herein.

In one embodiment, the method is a method of regulating (e.g., inhibiting) cell proliferation (e.g., proliferation of a cell), in vitro or in vivo, comprising contacting a cell with an effective amount of a PAPC compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

In one embodiment, the method is performed in vitro.

In one embodiment, the method is performed in vivo.

In one embodiment, the PAPC compound is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a PAPC compound, as described herein, for use in a method of treatment of the human or animal body by therapy.

Another aspect of the present invention pertains to a PAPC compound, as described herein, for use in a method of treatment of the human or animal body by therapy by oral administration.

In one embodiment, the method of treatment comprises treatment with both (i) a PAPC compound, as described herein, and (ii) one or more other agents selected from: (a) a DNA topoisomerase I or II inhibitor; (b) a DNA damaging agent; (c) an antimetabolite or thymidylate synthase (TS) inhibitor; (d) a microtubule targeted agent; and (e) ionising radiation.

Another aspect of the present invention pertains to (a) a DNA topoisomerase I or II inhibitor, (b) a DNA damaging agent, (c) an antimetabolite or thymidylate synthase (TS) inhibitor, or (d) a microtubule targeted agent, as described herein, for use in a method of treatment of the human or animal body by therapy, wherein the method of treatment comprises treatment with both (i) a PAPC compound, as described herein, and (a) the DNA topoisomerase I or II inhibitor, (b) the DNA damaging agent, (c) the antimetabolite or thymidylate synthase (TS) inhibitor, or (d) the microtubule targeted agent.

Use in the Manufacture of Medicaments

Another aspect of the present invention pertains to use of a PAPC compound, as described herein, in the manufacture of a medicament for use in treatment.

Another aspect of the present invention pertains to use of a PAPC compound, as described herein, in the manufacture of a medicament for use in treatment by oral administration.

In one embodiment, the medicament comprises the PAPC compound.

In one embodiment, the treatment comprises treatment with both (i) a medicament comprising a PAPC compound, as described herein, and (ii) one or more other agents selected from: (a) a DNA topoisomerase I or II inhibitor; (b) a DNA damaging agent; (c) an antimetabolite or thymidylate synthase (TS) inhibitor; (d) a microtubule targeted agent; and (e) ionising radiation.

Another aspect of the present invention pertains to use of (a) a DNA topoisomerase I or II inhibitor, (b) a DNA damaging agent, (c) an antimetabolite or TS inhibitor, or (d) a microtubule targeted agent, as described herein, in the manufacture of a medicament for use in a treatment, wherein the treatment comprises treatment with both (i) a PAPC compound, as described herein, and (a) the DNA topoisomerase I or II inhibitor, (b) the DNA damaging agent, (c) the antimetabolite or thymidylate synthase (TS) inhibitor, or (d) the microtubule targeted agent.

Methods of Treatment

Another aspect of the present invention pertains to a method of treatment comprising administering to a patient in need of treatment a therapeutically effective amount of a PAPC compound, as described herein, preferably in the form of a pharmaceutical composition.

Another aspect of the present invention pertains to a method of treatment comprising orally administering to a patient in need of treatment a therapeutically effective amount of a PAPC compound, as described herein, preferably in the form of a pharmaceutical composition.

In one embodiment, the method further comprises administering to the subject one or more other agents selected from: (a) a DNA topoisomerase I or II inhibitor; (b) a DNA damaging agent; (c) an antimetabolite or thymidylate synthase (TS) inhibitor; (d) a microtubule targeted agent; and (e) ionising radiation.

Conditions Treated—Conditions Mediated by CHK1

In one embodiment (e.g., of use in methods of therapy, of use in the manufacture of medicaments, of methods of treatment), the treatment is treatment of a disease or condition that is mediated by CHK1.

Conditions Treated—Conditions Ameliorated by the Inhibition of CHK1 Kinase Function In one embodiment (e.g., of use in methods of therapy, of use in the manufacture of medicaments, of methods of treatment), the treatment is treatment of: a disease or condition that is ameliorated by the inhibition of CHK1 kinase function.

Disorders Treated—Proliferative Conditions

In one embodiment (e.g., of use in methods of therapy, of use in the manufacture of medicaments, of methods of treatment), the treatment is treatment of: a proliferative condition.

The term "proliferative condition," as used herein, pertains to an unwanted or uncontrolled cellular proliferation of excessive or abnormal cells which is undesired, such as neoplastic or hyperplastic growth.

In one embodiment, the treatment is treatment of: a proliferative condition characterised by benign, pre-malignant, or malignant cellular proliferation, including for example: neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

Disorders Treated—Cancer

In one embodiment (e.g., of use in methods of therapy, of use in the manufacture of medicaments, of methods of treatment), the treatment is treatment of cancer.

In one embodiment, the treatment is treatment of lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, neuroblastoma, glioma, sarcoma, osteosarcoma, bone cancer, nasopharyngeal cancer (e.g., head cancer, neck cancer), skin cancer, squamous cancer, Kaposi's sarcoma, melanoma, malignant melanoma, lymphoma, or leukemia.

In one embodiment, the treatment is treatment of:
a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);
a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;
a hematopoietic tumor of myeloid lineage, for example acute and chronic myelogenous leukemias, myelodysplastic syndrome, or promyelocytic leukemia;

a tumour of mesenchymal origin, for example fibrosarcoma or habdomyosarcoma;

a tumor of the central or peripheral nervous system, for example astrocytoma, neuroblastoma, glioma or schwannoma;

melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of solid tumour cancer.

In one embodiment, the treatment is treatment of head cancer; neck cancer; nervous system cancer; brain cancer; neuroblastoma; lung/mediastinum cancer; breast cancer; oesophagus cancer; stomach cancer; liver cancer; biliary tract cancer; pancreatic cancer; small bowel cancer; large bowel cancer; colorectal cancer; gynaecological cancer; genito-urinary cancer; ovarian cancer; thyroid gland cancer; adrenal gland cancer; skin cancer; melanoma; bone sarcoma; soft tissue sarcoma; paediatric malignancy; Hodgkin's disease; non-Hodgkin's lymphoma; myeloma; leukaemia; or metastasis from an unknown primary site.

In one embodiment, the cancer is characterised by, or further characterised by, being p53 deficient cancer. In one embodiment, the cancer is p53 deficient cancer.

In one embodiment, the treatment is treatment of cancer metastasis.

In one embodiment, the cancer is characterised by, or further characterised by, cancer stem cells.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of cell migration (the spread of cancer cells to other parts of the body), the inhibition of invasion (the spread of tumour cells into neighbouring normal structures), or the promotion of cell apoptosis (programmed cell death). The compounds of the present invention may be used in the treatment of the cancers described herein, independent of the mechanisms discussed herein.

Treatment

The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

One aspect of the present invention pertains to a compound as described herein, in combination with one or more (e.g., 1, 2, 3, 4, etc.) additional therapeutic agents, for example, agents or therapies that regulate cell growth or survival or differentiation via a different mechanism, thus treating several characteristic features of cancer development.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Combination Therapies Employing DNA Damaging Agents

As discussed herein, in some embodiments, the PAPC compound is employed in combination with (e.g., in conjunction with) with one or more other agents selected from: (a) a DNA topoisomerase I or II inhibitor; (b) a DNA damaging agent; (c) an antimetabolite or thymidylate synthase (TS) inhibitor; (d) a microtubule targeted agent; and (e) ionising radiation.

When both a PAPC compound and one or more other agents are employed, they may be used (e.g., contacted, administered, etc.) in any order. Furthermore, they may be used (e.g., contacted, administered, etc.) together, as part of a single formulation, or separately, as separate formulations.

For example, in regard to methods of treatment employing both a PAPC compound and one or more other agents, treatment with (e.g., administration of) the PAPC compound may be prior to, concurrent with, or may follow, treatment with (e.g., administration of) the one or more other agents, or a combination thereof.

In one embodiment, treatment with (e.g., administration of) a PAPC compound is concurrent with, or follows, treatment with (e.g., administration of) the one or more other agents.

In one embodiment, the one or more other agents is a DNA topoisomerase I or II inhibitor; for example, Etoposide, Topotecan, Camptothecin, Irinotecan, SN-38, Doxorubicin, or Daunorubicin.

In one embodiment, the one or more other agents is a DNA damaging agent; for example, alkylating agents, platinating agents, or compounds that generate free radicals; for example, Temozolomide, Cisplatin, Carboplatin, Oxaliplatin, Mitomycin C, Cyclophosphamide, BCNU, CCNU, or Bleomycin.

In one embodiment, the one or more other agents is an antimetabolite or thymidylate synthase (TS) inhibitor; for example, 5-fluorouracil, hydroxyurea, Gemcitabine, Arabinosylcytosine, Fludarabine, Tomudex, or ZD9331.

In one embodiment, the one or more other agents is a microtubule targeted agent; for example, Paclitaxel, Docetaxel, Vincristine, or Vinblastine.

In one embodiment, the one or more other agents is ionising radiation (e.g., as part of radiotherapy).

Other Uses

The PAPC compounds described herein may also be used as cell culture additives to inhibit CHK1 kinase function, e.g., to inhibit cell proliferation, etc.

The PAPC compounds described herein may also be used as part of an in vitro assay, for example, in order to determine whether a candidate host is likely to benefit from treatment with the compound in question.

The PAPC compounds described herein may also be used as a standard, for example, in an assay, in order to identify other compounds, other CHK1 kinase function inhibitors, other anti-proliferative agents, other anti-cancer agents, etc.

Kits

One aspect of the invention pertains to a kit comprising (a) a PAPC compound as described herein, or a composition comprising a PAPC compound as described herein, e.g., preferably provided in a suitable container and/or with suitable packaging; and (b) instructions for use, e.g., written instructions on how to administer the compound or composition.

In one embodiment, the kit further comprises one or more other agents selected from: (a) a DNA topoisomerase I or II inhibitor; (b) a DNA damaging agent; (c) an antimetabolite or thymidylate synthase (TS) inhibitor; and (d) a microtubule targeted agent.

The written instructions may also include a list of indications for which the active ingredient is a suitable treatment.

Routes of Administration

The PAPC compound or pharmaceutical composition comprising the PAPC compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Preferably, the route of administration is oral, and the PAPC compound or pharmaceutical composition comprising the PAPC compound is administered to a subject orally.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for a PAPC compound to be administered alone, it is preferable to present it as a pharmaceutical formulation (e.g., composition, preparation, medicament) comprising at least one PAPC compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one PAPC compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 µg/mL, for example from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the PAPC compounds, and compositions comprising the PAPC compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular PAPC compound, the route of administration, the time of administration, the rate of excretion of the PAPC compound, the duration of the treatment, other drugs, compounds, and/or materials used in combination, the severity of the disorder, and the species, sex, age, weight, condition, general health, and prior medical history of the patient. The amount of PAPC compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the PAPC compound is in the range of about 10 µg to about 250 mg (more typically about 100 µg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

Chemical Synthesis

The following examples are provided solely to illustrate the present invention and are not intended to limit the scope of the invention, as described herein.

General Synthetic Procedures

Reactions were carried out under $N_2$. Microwave reactions were carried out using Biotage Initiator 60 or CEM microwave reactors. Flash silica chromatography was performed using Merck silica gel 60 (0.025-0.04 mm). Ion exchange chromatography was performed using Isolute Flash SCX-II (acidic) or Flash $NH_2$ (basic) resin cartridges. Gradient chromatography was carried out on a Biotage SP1 automated flash chromatography purification system. $^1$H NMR spectra were recorded on a Bruker AMX500 instrument at 500 MHz or a Bruker Avance instrument at 400 MHz using internal deuterium locks. Chemical shifts (δ) are reported relative to TMS (δ=0) and/or referenced to the solvent in which they were measured. Coupling constants (J) are reported in Hz. Combined HPLC-MS analyses were recorded using either:

1. (LCT) a Waters Alliance 2795 separations module and Waters/Micromass LCT mass detector with electrospray ionization (+ve or −ve ion mode as indicated) with HPLC performed using Supelco DISCOVERY C18, 50 mm×4.6 mm or 30 mm×4.6 mm i.d. columns, or Agilent 6210 TOF HPLC-MS with a Phenomenex Gemini 3 µm C18 (3 cm×4.6 mm i.d.) column. Both were run at a temperature of 22° C. with gradient elution of 10-90% MeOH/0.1% aqueous formic acid at a flow rate of 1 mL/min and a run time of 3.5 or 4 minutes as indicated. UV detection was at 254 nm and ionisation was by positive or negative ion electrospray. Molecular weight scan range was 50-1000 amu.

2. (ZQ) a Micromass ZQ mass spectrometer/Waters Alliance 2795 HT HPLC with a Phenomenex Gemini 5 µm, C18, 30 mm×4.6 mm i.d. column or Waters X-Bridge C18, 2.5 µm, 3.0×30 mm. Both were run at a temperature of 35° C. with a gradient elution of 5-95% (0.1% Ammonia in acetonitrile)/(0.1% Ammonia, 5% acetonitrile and 0.063% ammonium formate in water) at a flow rate of 2 mL/min and a run time of 4 or 6 minutes as indicated. UV detection was at 220-400 nm using a Waters 996 photodiode array UV detector and ionisation was by positive or negative ion electrospray. Molecular weight scan range was 80-1000 amu.

General Procedure i

Coupling of 5-iodo-2-chloropyridine Intermediates to 1-methyl-4-(4,4,5,5-tetramethyl-1,3,2-dioxaborolan-2-yl)-1H-pyrazole Scheme 1

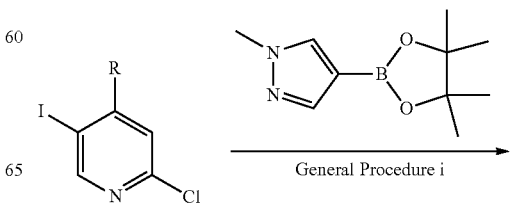

General Procedure i

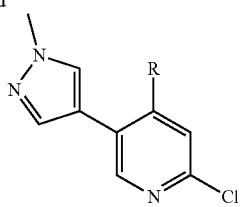

The appropriate 5-iodo-2-chloropyridine Intermediate I-8, or I-9 (1 eq) was dissolved in acetonitrile (7 mL solvent per 1 mmol of compound). 1-Methyl-4-(4,4,5,5-tetramethyl-1,3,2-dioxaborolan-2-yl)-1H-pyrazole (1 eq), tetrakis-(triphenylphosphine)palladium(0) (5 mol %) and sodium carbonate (1.5 eq) were added and the mixture was heated in a microwave reactor at 100° C. for 30 minutes (Intermediate I-8) or 15 minutes (Intermediate 1-9). The reaction mixture was concentrated in vacuo onto silica gel. Gradient chromatography (1-5% MeOH:CH$_2$Clover 15 column volume and 5-10% over 8 column volume) gave the required 5-substituted product.

General Procedure ii

Coupling of 5-iodo-2-chloropyridine Intermediates to ethynyltrimethylsilane or trimethyl((2-methylbut-3-yn-2-yl)oxy)silane

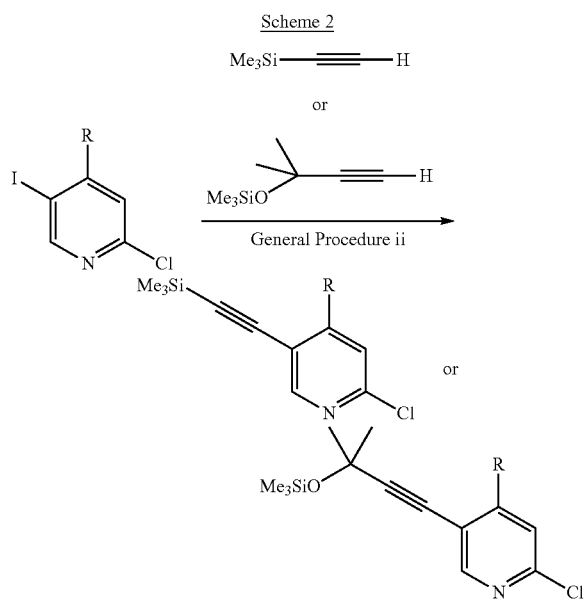

The appropriate 5-iodo-2-chloropyridine selected from Intermediates 1-8, or 1-9 (1 eq) 0.365 mmol) was dissolved in DMF (0.9 mL per 1 mmol of compound). Trimethyl(2-methylbut-3-yn-2-yloxy)silane or ethynyltrimethylsilane (1.3 eq) was added as appropriate. Dichlorobis(triphenylphosphine)palladium(II) (6 mol %), copper(I) iodide (6 mol %) and triethylamine (18 eq) were added. The mixture was heated in a microwave reactor at 120° C. for 10 minutes. The mixture was cooled and evaporated to dryness. Flash column chromatography on silica gel, eluting with ethyl acetate-hexane mixtures, gave the required 5-substituted product.

General Procedure iii

Coupling of 2-aminopyrazine Intermediates I-3, I-4 or I-5 to 2-chloropyridine Intermediates

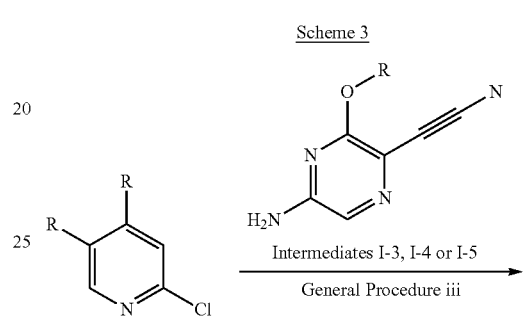

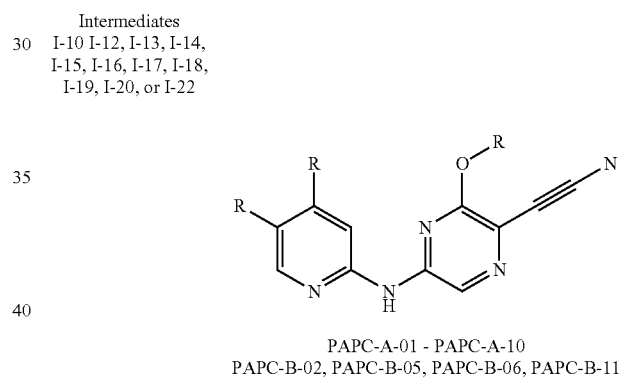

The appropriate 2-chloropyridine selected from Intermediates I-10, I-12, I-13, I-14, I-15, I-16, I-17, I-18, I-19, I-20, or I-22 (1 eq) was dissolved in toluene or dioxane (10 mL of solvent per 1 mmol of compound). The appropriate 2-aminopyrazine selected from Intermediates I-3, I-4, or I-5 (1 eq) was added. Xantphos (20 mol %), cesium carbonate (2 eq) and tris(dibenzylideneacetone)-dipalladium(0) (10 mol %) were added. The mixture was heated in the microwave at 130° C. for 60 minutes. The reaction mixture was diluted with MeOH (10 mL) and loaded onto a 2 g SCX-2 acidic ion exchange column. The column was flushed with MeOH (4×20 mL), followed by a solution of ammonia in MeOH (2 M; 4×20 mL). The basic elutant was concentrated in vacuo onto silica gel. Gradient chromatography (1-10% MeOH: 1% NH$_3$ in CH$_2$Cl$_2$ over 15 column volume) gave the required coupled product. If further purification was required to remove excess pyrazine starting material, then the material was subject to graduated preparative TLC (2-10% MeOH: 1% NH$_3$ in CH$_2$Cl$_2$).

General Procedure iv

Coupling of 2-aminopyrazine Intermediates 1-6 or 1-7 to 2-chloropyridine Intermediates with N-Boc deprotection Scheme 4

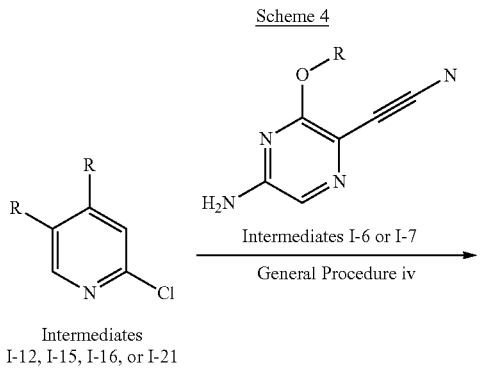

Intermediates I-12, I-15, I-16, or I-21

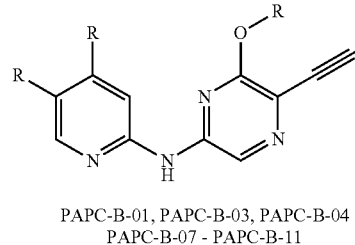

PAPC-B-01, PAPC-B-03, PAPC-B-04
PAPC-B-07 - PAPC-B-11

The appropriate 2-chloropyridine selected from Intermediates I-12, I-15, I-16, or I-21 (1 eq) was dissolved in toluene or dioxane (10 mL of solvent per 1 mmol of compound). The appropriate 2-aminopyrazine selected from Intermediates I-6 or I-7 (1 eq) was added. Xantphos (20 mol %), cesium carbonate (2 eq) and tris(dibenzylideneacetone)-dipalladium(0) (10 mol %) were added. The mixture was heated in the microwave at 130° C. for 60 minutes. The reaction mixture was diluted with MeOH (10 mL) and loaded onto a 2 g SCX-2 acidic ion exchange column. The column was flushed with MeOH (4×20 mL), followed by a solution of ammonia in MeOH (2 M; 4×20 mL). The basic elutant was concentrated in vacuo onto silica gel and subject to gradient chromatography (1-10% MeOH: 1% $NH_3$ in $CH_2Cl_2$ over 15 column volume) to give the N-Boc protected coupled product. The N-Boc protected coupled product (1 eq) was dissolved in $CH_2Cl_2$ (140 mL of solvent per 1 mmol of compound). Trifluoroacetic acid (470 eq) was added in one portion and the solution was stirred at room temperature for 30 minutes. The solution was concentrated in vacuo onto silica gel. Gradient chromatography (5% MeOH:1% $NH_3$ in $CH_2Cl$ over 5 column volume, then 5-20% over 15 column volume) gave the required N-deprotected product. If required, the product was further purified by graduated preparative thin-layer chromatography (2-10% MeOH: 1% $NH_3$ in $CH_2Cl_2$).

Intermediate I-1

(R)-1-(Dimethylamino)propan-2-ol

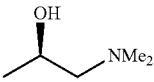

Dimethylamine 40% in water (11.39 mL, 90 mmol) was slowly added to (R)-propylene oxide (5.25 mL, 74.9 mmol) which had been cooled in an ice bath. This solution was stirred at room temperature for 2 hours before being extracted with $CH_2Cl_2$ (4×5 mL). The combined organic layers were dried over $Na_2SO_4$ and pure (R)-1-(dimethylamino)propan-2-ol (5.12 g, 49.6 mmol, 40% yield) was isolated as a clear oil by distillation under reduced pressure (50 mbar).

$^1$H NMR (CDCl$_3$, 500 MHz) δ 3.82-3.76 (m, 1H), 3.40 (brs, 1H), 2.27 (s, 6H), 2.25-2.21 (m, 1H), 2.16-2.12 (m, 1H), 1.12 (d, J=6.0, 3H).

Intermediate I-2

5-Amino-3-chloropyrazine-2-carbonitrile

2,6-Dichloropyrazine (2.89 g, 19.4 mmol) was stirred in aqueous $NH_3$ (28%, 10 mL) and heated to 100° C. in a sealed tube for 18 hours. The reaction mixture was cooled and the resultant precipitate was filtered. Trituration with water and then ether gave 6-chloropyrazin-2-amine as a white solid (2.28 g, 17.6 mmol, 91% yield).

$^1$H NMR (d$_6$-DMSO, 400 MHz) δ 6.9 (brs, 2H), 7.70 (d, J=0.4, 1H), 7.80 (d, J=0.4, 1H); LC-MS (ZQ, 6 minutes) Rt=1.05 minutes; m/z (ESI+) 130 (M+H).

6-Chloropyrazin-2-amine (2.50 g, 19.3 mmol) was stirred in $CH_2Cl_2$ (60 mL) at 0° C. N-Bromosuccinimide (2.92 g, 16.4 mmol) was added slowly and the reaction mixture was stirred at 0° C. for 60 minutes. The reaction mixture was filtered through celite and concentrated to give a brown oil. Purification by flash chromatography, eluting with 0-25% EtOAc-hexanes, gave 5-bromo-6-chloropyrazin-2-amine as a yellow solid (1.69 g, 8.16 mmol, 42% yield).

$^1$H NMR (d$_6$-DMSO, 400 MHz) δ 7.1 (brs, 2H), 7.65 (s, 1H); LC-MS (ZQ, 4 minutes) Rt=1.46 minutes; m/z (ESI−) 205 (M−H).

A mixture of 5-bromo-6-chloropyrazin-2-amine (1.00 g, 4.8 mmol), copper (I) iodide (914 mg, 4.8 mmol), 18-crown-6 (95 mg, 0.36 mmol) and tetrakis(triphenylphosphine)palladium (0) (83 mg, 0.072 mmol) was suspended in dry DMF (20 mL) and a stream of nitrogen was passed through for 5 minutes. Potassium cyanide (312 mg, 4.8 mmol) was added and the mixture was stirred at room temperature for 30 minutes, then refluxed at 200° C. for 3 hours. The mixture was cooled, diluted with EtOAc and absorbed onto silica gel (10 g). DMF was removed by evaporation. The product was purified by flash chromatography, eluting with 1:1 EtOAc-hexanes, to yield 5-amino-3-chloropyrazine-2-carbonitrile as a yellow solid (607 mg, 3.93 mmol, 82% yield).

$^1$H NMR (d$_6$ DMSO, 400 MHz) δ 7.87 (s, 1H), 8.1 (brs, 2H); LC-MS (ZQ, 4 minutes) Rt=1.20 minutes; m/z (ESI−) 153 (M−H).

Intermediate I-3

(R)-5-Amino-3-((1-(dimethylamino)propan-2-yl)oxy)pyrazine-2-carbonitrile

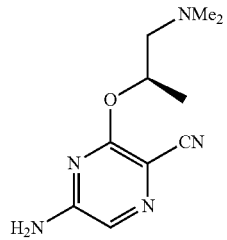 [SMILES: C[C@H](CN(C)C)Oc1nc(N)cnc1C#N]

(R)-1-(Dimethylamino)propan-2-ol (0.667 g, 6.47 mmol) was added dropwise to a suspension of NaH (60% in oil; 0.388 g, 9.71 mmol) in dioxane (16.2 mL) and stirred for 30 minutes. 5-Amino-3-chloropyrazine-2-carbonitrile (Intermediate I-2) (1.00 g, 6.47 mmol) was added in one portion and the mixture was heated at 90° C. for 14 hours. After cooling, water (200 mL) was added and the solution was extracted with Et$_2$O (4×100 mL), dried over MgSO$_4$, and the volatiles removed under vacuum. Gradient column chromatography eluting with MeOH: 1% NH$_3$ in CH$_2$Cl$_2$, gave (R)-5-amino-3-((1-(dimethylamino)propan-2-yl)oxy)pyrazine-2-carbonitrile (0.558 g, 2.52 mmol, 39% yield) as a yellow solid.

$^1$H NMR (500 MHz, CDCl$_3$) δ 7.54 (s, 1H), 5.42-5.35 (m, 1H), 5.31 (brs, 2H), 2.76 (dd, J=7.5, 13.5, 1H), 2.52 (dd, J=4.0, 13.5, 1H), 2.37 (s, 6H), 1.35 (d, J=6.5, 3H); LC-MS (LCT, 3.5 minutes) Rt=0.80 minutes; m/z (ESI) 222 (M+H).

Intermediate I-4

(R)-5-Amino-3-((1-methylpyrrolidin-3-yl)oxy)pyrazine-2-carbonitrile

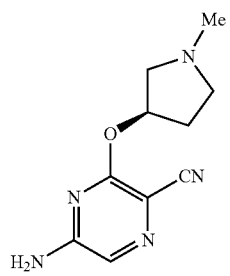 [SMILES: CN1CC[C@@H](Oc2nc(N)cnc2C#N)C1]

Prepared as described for Intermediate I-3 replacing (R)-1-(dimethylamino)propan-2-ol with (R)-1-methylpyrrolidin-3-ol.

$^1$H NMR (500 MHz, d$_6$-DMSO) δ 7.60 (brs, 2H), 7.51 (s, 1H), 5.36-5.28 (m, 1H), 2.76 (dd, J=10.8, 6.1, 1H), 2.69 (ddd, J=8.2, 8.2, 5.3, 1H), 2.62 (dd, J=10.8, 2.8, 1H), 2.37-2.21 (m, 2H), 2.26 (s, 3H), 1.85-1.77 (m, 1H); LC-MS (LCT, 3.5 minutes) Rt=0.62 minutes; m/z (ESI) 220 (M+H).

Intermediate I-5

(S)-5-Amino-3-((1-methylpyrrolidin-3-yl)oxy)pyrazine-2-carbonitrile

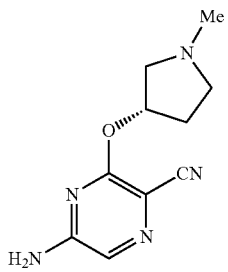 [SMILES: CN1CC[C@H](Oc2nc(N)cnc2C#N)C1]

Prepared as described for Intermediate I-3 replacing (R)-1-(dimethylamino)propan-2-ol with (S)-1-methylpyrrolidin-3-ol.

$^1$H NMR (500 MHz, d$_6$-DMSO) δ 7.60 (brs, 2H), 7.51 (s, 1H), 5.36-5.28 (m, 1H), 2.76 (dd, J=10.8, 6.1, 1H), 2.69 (ddd, J=8.2, 8.2, 5.3, 1H), 2.62 (dd, J=10.8, 2.8, 1H), 2.37-2.21 (m, 2H), 2.26 (s, 3H), 1.85-1.77 (m, 1H); LC-MS (LCT, 3.5 minutes) Rt=0.62 minutes; m/z (ESI) 220 (M+H).

Intermediate I-6

(R)-tert-Butyl 3-((6-amino-3-cyanopyrazin-2-yl)oxy)pyrrolidine-1-carboxylate

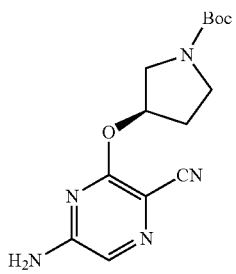 [SMILES: CC(C)(C)OC(=O)N1CC[C@@H](Oc2nc(N)cnc2C#N)C1]

Prepared as described for Intermediate I-3 replacing (R)-1-(dimethylamino)propan-2-ol with (R)-tert-butyl 3-hydroxypyrrolidine-1-carboxylate.

Isolated as a mixture of rotamers. $^1$H NMR (500 MHz, CDCl$_3$) 67.61-7.58 (m, 1H), 5.49-5.44 (m, 1H), 5.35-5.30 (m, 2H), 3.69-3.65 (m, 1H), 3.63-3.50 (m, 3H), 2.28-2.11 (m, 2H), 1.46 (s, 9H); LC-MS (LCT, 3.5 minutes) Rt=2.67 minutes; m/z (ESI) 328 (M+Na).

Intermediate I-7

(S)-tert-Butyl 3-((6-amino-3-cyanopyrazin-2-yl)oxy)pyrrolidine-1-carboxylate

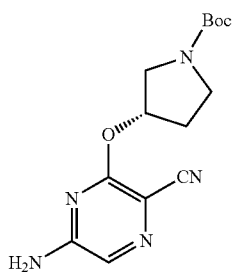 [SMILES: CC(C)(C)OC(=O)N1CC[C@H](Oc2nc(N)cnc2C#N)C1]

Prepared as described for Intermediate I-3 replacing (R)-1-(dimethylamino)propan-2-ol with (S)-tert-butyl 3-hydroxypyrrolidine-1-carboxylate.

Isolated as a mixture of rotamers. $^1$H NMR (500 MHz, CDCl$_3$) δ 7.61-7.58 (m, 1H), 5.49-5.44 (m, 1H), 5.35-5.30 (m, 2H), 3.69-3.65 (m, 1H), 3.63-3.50 (m, 3H), 2.28-2.11 (m, 2H), 1.46 (s, 9H); LC-MS (LCT, 3.5 minutes) Rt=2.67 minutes; m/z (ESI) 328 (M+Na).

Intermediate I-8

2-Chloro-5-iodo-N-methylpyridin-4-amine

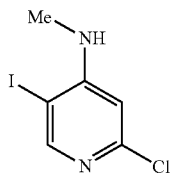

2-Chloro-5-iodopyridin-4-amine (2.0 g, 7.86 mmol) and paraformaldehyde (0.472 g, 15.7 mmol) were dissolved in AcOH (56.1 mL) and stirred for 2.5 hours at 40° C. Sodium triacetoxyborohydride (3.66 g, 17.3 mmol) was added and the mixture was stirred at 40° C. for 1.5 hours. Further sodium triacetoxyborohydride (3.66 g, 17.3 mmol) was added and the mixture was stirred for a further 19 hours. The reaction mixture was reduced in volume by half by evaporation in vacuo. Water was added to the mixture, followed by basification with NaHCO$_3$. The mixture was extracted with EtOAc (3×70 mL) and the combined organic layers were dried over MgSO$_4$. Silica was added and the solution was concentrated. Gradient chromatography, eluting with 5-10% EtOAc in c-Hex for 4 column volume and then 10% EtOAc in c-Hex for a further 11 column volume, gave 2-chloro-5-iodo-N-methylpyridin-4-amine (1.65 g, 6.14 mmol, 78% yield) as a white crystalline powder.

$^1$H NMR (500 MHz, CDCl$_3$) δ 8.27 (s, 1H), 6.41 (s, 1H), 4.85 (brs, 1H), 2.93 (d, J=5.0, 3H); LC-MS (LCT, 3.5 minutes) Rt=1.90 minutes; m/z (ESI) 268 (M+H).

Intermediate I-9

2-Chloro-5-iodo-4-methoxypyridine

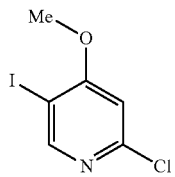

To a solution of 2-chloro-4-methoxypyridine (0.5 g, 3.48 mmol) in sulfuric acid (2.5 mL) was added N-iodosuccinimide (0.825 g, 3.48 mmol) portionwise at room temperature. The mixture was stirred at 55° C. for 2 hours. The reaction mixture was poured into ice water (10 mL) and 8 M NaOH (20 mL) was added slowly, after which the dark brown solution turned pale yellow. The aqueous layer was extracted with CH$_2$Cl$_2$ (2×20 mL). The organic layers were washed with brine (10 mL) and concentrated in vacuo onto silica gel. Dry flash chromatography, eluting with 25% EtOAc:c-Hex, gave 2-chloro-5-iodo-4-methoxypyridine as a white crystalline solid (0.169 g, 0.760 mmol, 22% yield).

$^1$H NMR (500 MHz, d$_6$-DMSO) δ 8.52 (s, 1H), 7.19 (s, 1H), 3.96 (s, 3H); LC-MS (LCT, 4 minutes) Rt=2.56 minutes; m/z (ESI) 270 (M+H).

Intermediate I-10

Methyl 6-chloro-4-(methylamino)nicotinate

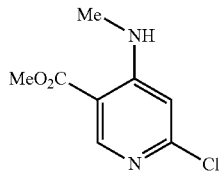 [SMILES: CNc1cc(Cl)ncc1C(=O)OC]

40% Methylamine in water (0.847 mL, 9.78 mmol) was added slowly over 5 minutes at 0° C. to a solution of methyl 4,6-dichloronicotinate (0.40 g, 1.94 mmol) in MeCN (6 mL). The solution was stirred at 0° C. for 30 minutes then at room temperature for 2 hours. The reaction mixture was concentrated in vacuo onto silica gel. Gradient chromatography, eluting with 5% EtOAc:c-Hex over 5 column volume and 5-50% over 15 column volume, gave methyl 6-chloro-4-(methylamino)nicotinate (278 mg, 1.386 mmol, 71.4% yield) as a white solid.

$^1$H NMR (500 MHz, CDCl$_3$) δ 8.65 (s, 1H), 8.10 (brs, 1H), 6.54 (s, 1H), 3.88 (s, 3H), 2.92 (d, J=5.1, 3H); LC-MS (LCT, 3.5 minutes) Rt=2.35 minutes; m/z (ESI) 201 (M+H).

Intermediate I-11

Methyl 6-chloro-4-methoxynicotinate

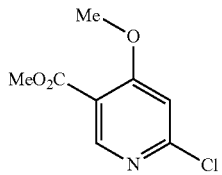 [SMILES: COC(=O)c1cnc(Cl)cc1OC]

Sodium methoxide powder (0.136 g, 2.52 mmol) was added slowly to a stirred solution of methyl 4,6-dichloronicotinate (0.40 g, 1.94 mmol) in THF (4 mL) at room temperature. The reaction mixture was stirred at room temperature for 18 hours, then concentrated in vacuo onto silica gel. Gradient chromatography, eluting with 5% EtOAc:c-Hex over 5 column volume and 5-50% over 15 column volume, gave methyl 6-chloro-4-methoxynicotinate (218 mg, 1.08 mmol, 56% yield) as a white crystalline solid.

$^1$H NMR (500 MHz, CDCl$_3$) δ 8.71 (s, 1H), 6.92 (s, 1H), 3.97 (s, 3H), 3.90 (s, 3H); LC-MS (LCT, 3.5 minutes) Rt=2.13 minutes; m/z (ESI) 202 (M+H).

Intermediate I-12

Methyl 6-chloro-4-(dimethylamino)nicotinate

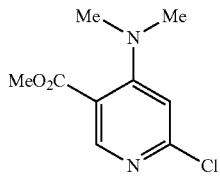 [SMILES: COC(=O)c1cnc(Cl)cc1N(C)C]

Dimethylamine (1.23 mL, 9.71 mmol) was slowly added to a stirred solution of methyl 4,6-dichloronicotinate (0.40 g, 1.94 mmol) in MeCN (6 mL) at room temperature. The solution was stirred at room temperature for 18 hours then concentrated in vacuo onto silica gel. Gradient chromatography, eluting with 5% EtOAc:c-Hex over 5 column volume and 5-50% over 15 column volume, gave methyl 6-chloro-4-(dimethylamino)nicotinate (335 mg, 1.56 mmol, 80% yield) as a white solid.

$^1$H NMR (500 MHz, d$_6$-DMSO) δ 8.21 (s, 1H), 6.85 (s, 1H), 3.83 (s, 3H), 2.90 (s, 6H); LC-MS (LCT, 3.5 minutes) Rt=2.23 minutes; m/z (ESI) 215 (M+H).

Intermediate I-13

2-Chloro-N-methyl-5-(trifluoromethyl)pyridin-4-amine

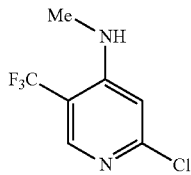 [SMILES: CNc1cc(Cl)ncc1C(F)(F)F]

2 M Methylamine in MeOH (11.6 mL, 23.2 mmol) was added to 2-chloro-4-iodo-5-(trifluoromethyl)pyridine (357 mg, 1.16 mmol) and the mixture was heated in a microwave reactor at 130° C. for 1 hour. The mixture was concentrated in vacuo. Preparative thin-layer chromatography, eluting with 20% EtOAc:hexane, gave 2-chloro-N-methyl-5-(trifluoromethyl)pyridin-4-amine (77 mg, 0.363 mmol, 31% yield).

$^1$H NMR (500 MHz, d$_6$-DMSO) δ 8.17 (s, 1H), 6.90 (brs, 1H), 6.74 (s, 1H), 2.81 (d, J=5, 3H); LC-MS (LCT, 3.5 minutes) Rt=1.98 minutes; m/z (ESI) 211 (M+H).

Intermediate I-14

2,5-Dichloro-N-methylpyridin-4-amine

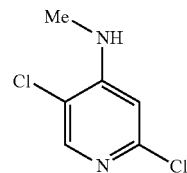

N-Chlorosuccinimide (0.623 g, 4.67 mmol) was added to 2-chloro-N-methyl-pyridin-4-amine (0.50 g, 3.89 mmol) and potassium acetate (0.763 g, 7.78 mmol) in AcOH (25 mL) and the mixture was stirred at 80° C. for 1.25 hours. The mixture was cooled and concentrated in vacuo. The concentrated mixture was diluted with water, neutralised with aqueous NaOH and extracted with EtOAc (×3). The organic extracts were evaporated onto silica gel. Gradient chromatography, eluting with 10-50% EtOAc:c-Hex, gave 2,5-dichloro-N-methylpyridin-4-amine (0.114 g, 0.699 mmol, 18% yield).

$^1$H NMR (500 MHz, CDCl$_3$) δ 8.02 (s, 1H), 6.52 (s, 1H), 4.95 (brs, 1H), 2.96 (d, J=5, 3H); LC-MS (LCT, 4 minutes) Rt=2.17 minutes; m/z (ESI) 177 (M+H).

Intermediate I-15

2-Chloro-N-methyl-5-(1-methyl-1H-pyrazol-4-yl)pyridin-4-amine

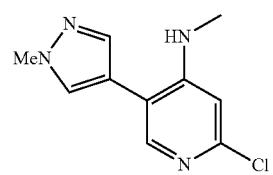

Prepared from Intermediate I-8 and 1-methyl-4-(4,4,5,5-tetramethyl-1,3,2-dioxaborolan-2-yl)-1H-pyrazole following General Procedure i.

$^1$H NMR (500 MHz, CDCl$_3$) δ 7.83 (s, 1H), 7.56 (s, 1H), 7.45 (s, 1H), 6.48 (s, 1H), 4.68 (brs, 1H), 3.96 (s, 3H), 2.84 (d, J=5.1, 3H); LC-MS (LCT, 3.5 minutes) Rt=1.09 minutes; m/z (ESI) 223 (M+H).

Intermediate I-16

2-Chloro-4-methoxy-5-(1-methyl-1H-pyrazol-4-yl)pyridine

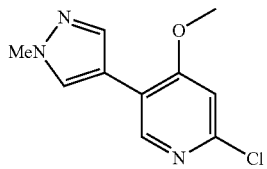

Prepared from Intermediate I-9 and 1-methyl-4-(4,4,5,5-tetramethyl-1,3,2-dioxaborolan-2-yl)-1H-pyrazole following General Procedure i.

$^1$H NMR (500 MHz, CDCl$_3$) δ 7.83 (s, 1H), 7.56 (s, 1H), 7.45 (s, 1H), 6.48 (s, 1H), 4.68 (brs, 1H), 3.96 (s, 3H), 2.84 (d, J=5.1, 3H); LC-MS (LCT, 3.5 minutes) Rt=1.09 minutes; m/z (ESI) 224 (M+H).

Intermediate I-17

2-Chloro-N,N-dimethyl-5-(1-methyl-1H-pyrazol-4-yl)pyridin-4-amine

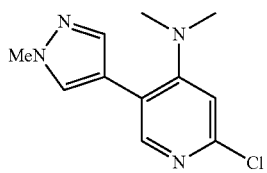 [SMILES: CN(C)c1cc(Cl)ncc1-c1cnn(C)c1]

DMF (2.99 mL) was slowly added to stirred sodium hydride (60% in oil; 51 mg, 1.28 mmol) and 2-chloro-N-methyl-5-(1-methyl-1H-pyrazol-4-yl)pyridin-4-amine (Intermediate I-15) (104 mg, 0.467 mmol) at room temperature. The mixture was warmed to 80° C. for 10 minutes, followed by addition of iodomethane (0.035 mL, 0.560 mmol). The mixture was stirred at 80° C. for 30 minutes, then cooled and diluted with saturated aqueous NaHCO$_3$ (45 mL) and ethyl acetate (70 mL). After stirring for 10 minutes, the organic layer was separated and the aqueous layer was extracted with ethyl acetate (2×70 mL). The combined organic layers were evaporated onto silica gel. Gradient chromatography, eluting with 1-10% MeOH: 1% NH$_3$ in CH$_2$Cl$_2$ over 10 column volume, gave 2-chloro-N,N-dimethyl-5-(1-methyl-1H-pyrazol-4-yl)pyridin-4-amine (102 mg, 0.431 mmol, 92% yield).

$^1$H NMR (500 MHz, CDCl$_3$) δ 8.03 (s, 1H), 7.67 (s, 1H), 7.57 (s, 1H), 6.77 (s, 1H), 3.96 (s, 3H), 2.72 (s, 6H).

Intermediate I-18

2-Chloro-N-ethyl-5-(1-methyl-1H-pyrazol-4-yl)pyridin-4-amine

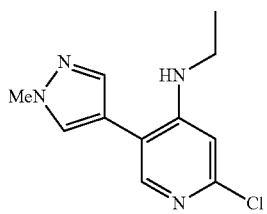 [SMILES: CCNc1cc(Cl)ncc1-c1cnn(C)c1]

A mixture of 2-chloro-5-iodopyridin-4-amine (262 mg, 1.03 mmol), excess paraformaldehyde (618 mg, 21 mmol) and AcOH (10.3 mL) was stirred at 40° C. for 15 minutes, followed by addition of excess sodium triacetoxyborohydride (4.8 g, 23 mmol). After stirring for 2.5 hours, further paraformaldehyde (236 mg, 7.86 mmol) and sodium triacetoxyborohydride (1.83 g, 8.63 mmol) were added. After 18 hours, the mixture was diluted with water and basified with NaHCO$_3$. The mixture was extracted with EtOAc (3×30 mL). The combined organic extracts were dried and evaporated onto silica. Gradient chromatography, eluting with 5-10% EtOH: CH$_2$Cl$_2$ over 17 column volume, gave 2-chloro-N-ethyl-5-iodopyridin-4-amine (291 mg, 1.03 mmol, 100% yield). LC-MS (LCT, 3.5 minutes) Rt=2.56 minutes; m/z (ESI) 282 (M+H). The material was reacted with 1-methyl-4-(4,4,5,5-tetramethyl-1,3,2-dioxaborolan-2-yl)-1H-pyrazole following General Procedure i to give 2-chloro-N-ethyl-5-(1-methyl-1H-pyrazol-4-yl)pyridin-4-amine.

$^1$H NMR (500 MHz, CDCl$_3$) δ 7.84 (s, 1H), 7.59 (s, 1H), 7.47 (s, 1H), 6.50 (s, 1H), 4.60 (brs, 1H), 3.99 (s, 3H), 3.19 (2H, q, J=7.2), 1.25 (t, J=7.2, 3H); LC-MS (LCT, 3.5 minutes) Rt=1.35 minutes; m/z (ESI) 237 (M+H).

Intermediate I-19

2-Chloro-N-methyl-5-((trimethylsilyl)ethynyl)pyridin-4-amine

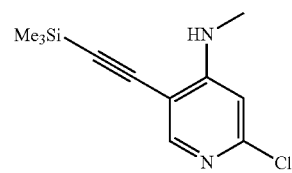

Prepared from Intermediate I-8 and ethynyltrimethylsilane following General Procedure ii.

$^1$H NMR (500 MHz, CDCl$_3$) δ 8.11 (s, 1H), 6.47 (s, 1H), 5.15 (brs, 1H), 2.97 (d, J=5, 3H), 0.3 (9H, s); LC-MS (LCT, 4 minutes) Rt=3.13 minutes; m/z (ESI) 239 (M+H).

Intermediate I-20

2-Chloro-N-methyl-5-(3-methyl-3-((trimethylsilyl)oxy)but-1-yn-1-yl)pyridin-4-amine

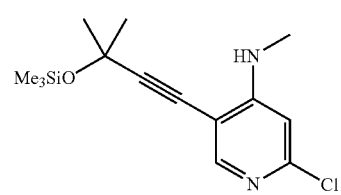

Prepared from Intermediate I-8 and trimethyl(2-methylbut-3-yn-2-yloxy)silane following General Procedure ii.

$^1$H NMR (500 MHz, CDCl$_3$) δ 8.04 (s, 1H), 6.46 (s, 1H), 5.00 (brs, 1H), 2.94 (d, J=5, 3H), 1.62 (6H, s), 0.22 (s, 9H); LC-MS (LCT, 3.5 minutes) Rt=2.81 minutes; m/z (ESI) 297 (M+H).

Intermediate I-21

2-Chloro-4-methoxy-5-(3-methyl-3-((trimethylsilyl)oxy)but-1-yn-1-yl)pyridine

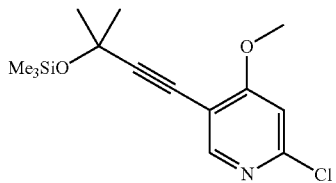

Prepared from Intermediate I-9 and trimethyl(2-methylbut-3-yn-2-yloxy)silane following General Procedure ii.

¹H NMR (500 MHz, CDCl₃) δ 8.25 (s, 1H), 6.82 (s, 1H), 3.92 (s, 3H), 1.60 (6H, s), 0.23 (s, 9H); LC-MS (LCT, 4 minutes) Rt=3.23 minutes; m/z (ESI) 298 (M+H).

Intermediate I-22

2-Chloro-5-cyclopropyl-N-methylpyridin-4-amine

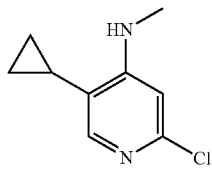

2-Chloro-5-iodo-N-methylpyridin-4-amine (Intermediate I-8) (30 mg, 0.112 mmol), tetrakis(triphenylphosphine) palladium (0) (6.5 mg, 5.59 μmol) and 0.5 M aqueous sodium carbonate solution (290 μL, 0.145 mmol) were added to 2-cyclopropyl-4,4,5,5-tetramethyl-1,3,2-dioxaborolane (61 μL, 0.335 mmol) in MeCN. The mixture was heated at 130° C. in a microwave reactor for 1 hour. The mixture was concentrated in vacuo. Preparative thin layer chromatography, eluting with 1% NH₃, 6% MeOH in CH₂Ol₂, gave 2-chloro-5-cyclopropyl-N-methylpyridin-4-amine (10 mg, 0.055 mmol, 49% yield) as a white powder.

¹H NMR (500 MHz, CDCl₃) δ 7.72 (s, 1H), 6.34 (s, 1H), 4.82 (brs, 1H), 2.85 (s, 3H), 1.37-1.34 (m, 1H), 0.85-0.82 (m, 2H), 0.49-0.46 (m, 2H); LC-MS (LCT, 4 minutes) Rt=1.23 minutes; m/z (ESI) 183 (M+H).

Compound PAPC-A-01

(R)-3-((1-(Dimethylamino)propan-2-yl)oxy)-5-((4-methoxy-5-(1-methyl-1H-pyrazol-4-yl)pyridin-2-yl)amino)pyrazine-2-carbonitrile

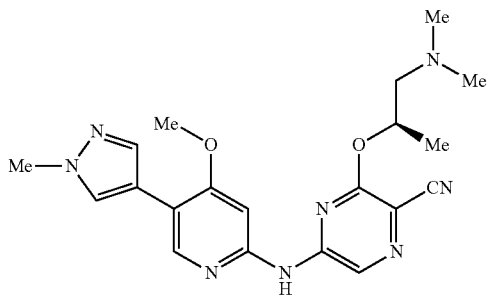 [SMILES: COc1cc(Nc2cnc(C#N)c(O[C@H](C)CN(C)C)n2)ncc1-c1cnn(C)c1]

Prepared from Intermediate I-16 and Intermediate I-3 following General Procedure iii.

¹H NMR (500 MHz, CDCl₃/CD₃OD) δ 9.14 (s, 1H), 8.35 (s, 1H), 7.83 (s, 1H), 7.76 (s, 1H), 7.06 (s, 1H), 5.87-5.75 (m, 1H), 4.00 (s, 3H), 3.94 (s, 3H), 3.35 (dd, J=13.7, 6.7, 1H), 3.21 (d, J=13.7, 1H), 2.87 (s, 6H), 1.53 (d, J=6.4, 3H); LC-MS (LCT, 3.5 minutes) Rt=2.11 minutes; m/z (ESI) 409 (M+H).

Compound PAPC-A-02

(R)-3-((1-(Dimethylamino)propan-2-yl)oxy)-5-((5-(1-methyl-1H-pyrazol-4-yl)-4-(methylamino)pyridin-2-yl)amino)pyrazine-2-carbonitrile

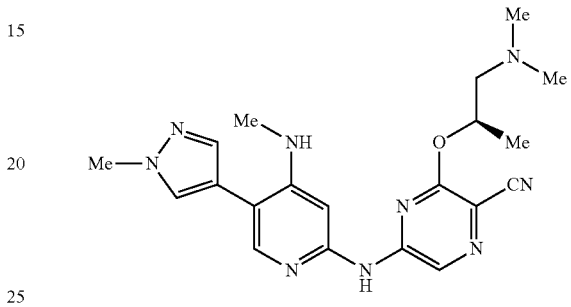

Prepared from Intermediate I-15 and Intermediate I-3 following General Procedure iii.

¹H NMR (500 MHz, CDCl₃) δ 8.23 (brs, 1H), 8.23 (s, 1H), 7.85 (s, 1H), 7.58 (s, 1H), 7.47 (s, 1H), 7.03 (s, 1H), 5.48-5.37 (m, 1H), 4.72 (q, J=5, 1H), 3.98 (s, 3H), 2.90 (d, J=5, 3H), 2.74 (dd, J=13.4, 7.2, 1H), 2.51 (dd, J=13.4, 4.4, 1H), 2.31 (s, 6H), 1.41 (d, J=6.3, 3H); LC-MS (LCT, 3.5 minutes) Rt=1.09 minutes; m/z (ESI) 408 (M+H).

Compound PAPC-A-03

(R)-5-((4-(Dimethylamino)-5-(1-methyl-1H-pyrazol-4-yl)pyridin-2-yl)amino)-3-((1-(dimethylamino)propan-2-yl)oxy)pyrazine-2-carbonitrile

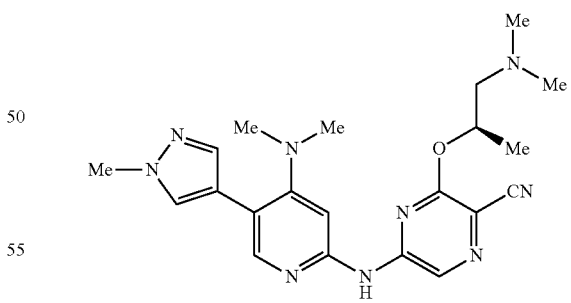

Prepared from Intermediate I-17 and Intermediate I-3 following General Procedure iii.

¹H NMR (500 MHz, CDCl₃) δ 8.61 (brs, 1H), 8.23 (s, 1H), 8.04 (s, 1H), 7.69 (s, 1H), 7.57 (s, 1H), 7.29 (s, 1H), 5.50-5.39 (m, 1H), 3.97 (s, 3H), 2.76 (s, 6H), 2.73 (dd, J=13.4, 7.3, 1H), 2.50 (dd, J=13.4, 4.4, 1H), 2.30 (s, 6H), 1.40 (d, J=6.3, 3H); LC-MS (LCT, 3.5 minutes) Rt=1.59 minutes; m/z (ESI) 418 (M+H).

Compound PAPC-A-04

(R)-3-((1-(Dimethylamino)propan-2-yl)oxy)-5-((4-(ethylamino)-5-(1-methyl-1H-pyrazol-4-yl)pyridin-2-yl)amino)pyrazine-2-carbonitrile

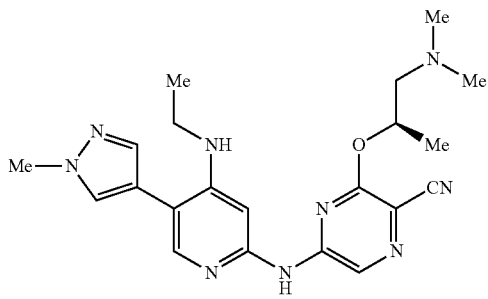 [SMILES: CCNc1cc(Nc2cnc(C#N)c(O[C@H](C)CN(C)C)n2)ncc1-c1cnn(C)c1]

Prepared from Intermediate I-18 and Intermediate I-3 following General Procedure iii.

$^1$H NMR (500 MHz, CDCl$_3$) δ 8.29 (s, 1H), 7.86 (s, 1H), 7.61 (s, 1H), 7.50 (s, 1H), 7.07 (s, 1H), 5.50-5.47 (m, 1H), 4.63-4.61 (m, 1H), 4.02 (s, 3H), 3.27-3.23 (m, 2H), 2.84-2.80 (m, 1H), 2.62-2.59 (m, 1H), 2.39 (s, 6H), 1.43 (d, J=6.3, 3H), 1.30 (t, J=7.3, 3H); LC-MS (LCT, 3.5 minutes) Rt=1.22 minutes; m/z (ESI) 422 (M+H).

Compound PAPC-A-05

(R)-3-((1-(Dimethylamino)propan-2-yl)oxy)-5-((4-(methylamino)-5-(trifluoromethyl)pyridin-2-yl)amino)pyrazine-2-carbonitrile

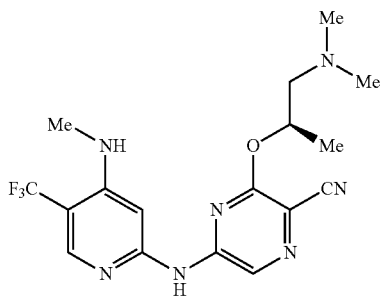 [SMILES: CNc1cc(Nc2cnc(C#N)c(O[C@H](C)CN(C)C)n2)ncc1C(F)(F)F]

Prepared from Intermediate I-13 and Intermediate I-3 following General Procedure iii.

$^1$H NMR (500 MHz, CD$_3$OD) δ 8.60 (s, 1H), 8.16 (s, 1H), 6.98 (s, 1H), 5.59-5.53 (m, 1H), 2.94 (s, 3H), 2.82 (dd, J=13.7, 8, 1H), 2.51 (dd, J=13.7, 5, 1H), 2.33 (s, 6H), 1.42 (d, J=6, 3H); LC-MS (LCT, 3.5 minutes) Rt=1.75 minutes; m/z (ESI) 396 (M+H).

Compound PAPC-A-06

(R)-5-((5-Chloro-4-(methylamino)pyridin-2-yl)amino)-3-((1-(dimethylamino)propan-2-yl)oxy)pyrazine-2-carbonitrile

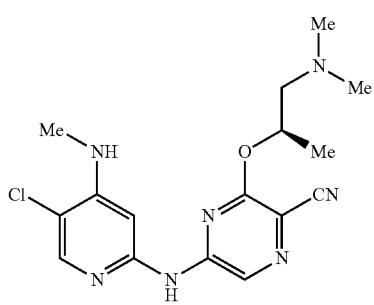 [SMILES: CNc1cc(Nc2cnc(C#N)c(O[C@H](C)CN(C)C)n2)ncc1Cl]

Prepared from Intermediate I-14 and Intermediate I-3 following General Procedure iii.

$^1$H NMR (500 MHz, CDCl$_3$) δ 8.22 (s, 1H), 8.02 (brs, 1H), 7.98 (s, 1H), 7.01 (s, 1H), 5.48-5.36 (m, 1H), 4.97 (brq, J=4.2, 1H), 2.98 (d, J=5.1, 3H), 2.74 (dd, J=13.3, 7.3, 1H), 2.51 (dd, J=13.3, 4.3, 1H), 2.31 (s, 6H), 1.41 (d, J=6.3, 3H); LC-MS (LCT, 3.5 minutes) Rt=1.77 minutes; m/z (ESI) 362 (M+H).

Compound PAPC-A-07

(R)-3-((1-(Dimethylamino)propan-2-yl)oxy)-5-((5-ethynyl-4-(methylamino)pyridin-2-yl)amino)pyrazine-2-carbonitrile

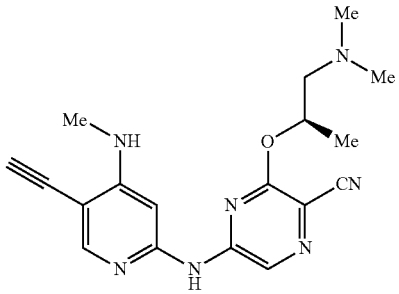 [SMILES: C#Cc1cnc(Nc2cnc(C#N)c(O[C@H](C)CN(C)C)n2)cc1NC]

Prepared from Intermediate I-19 and Intermediate I-3 following General Procedure iii.

$^1$H NMR (500 MHz, CDCl$_3$) δ 8.28 (s, 1H), 8.13 (s, 1H), 7.80 (brs, 1H), 6.94 (s, 1H), 5.45-5.40 (m, 1H), 5.21-5.19 (m, 1H), 3.49 (s, 1H), 3.00 (s, 3H), 2.76-2.73 (m, 1H), 2.54-2.52 (m, 1H), 2.34 (s, 6H), 1.43 (d, J=6, 3H); LC-MS (LCT, 4 minutes) Rt=1.53 minutes; m/z (ESI) 352 (M+H).

Compound PAPC-A-08

(R)-3-((1-(Dimethylamino)propan-2-yl)oxy)-5-((5-(3-hydroxy-3-methylbut-1-yn-1-yl)-4-(methylamino)pyridin-2-yl)amino)pyrazine-2-carbonitrile

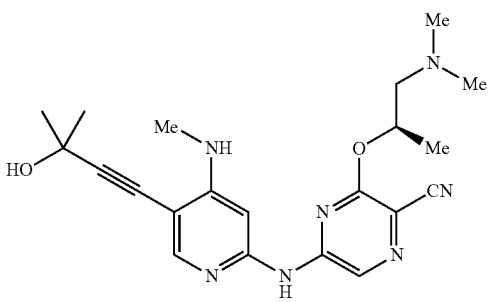 [SMILES: CNc1cc(Nc2cnc(C#N)c(O[C@H](C)CN(C)C)n2)ncc1C#CC(C)(C)O]

Prepared from Intermediate I-20 and Intermediate I-3 following General Procedure iii.

$^1$H NMR (500 MHz, CD$_3$OD) δ 8.46 (s, 1H), 7.95 (s, 1H), 6.92 (s, 1H), 5.59-5.55 (m, 1H), 2.97 (s, 3H), 2.85 (dd, J=13, 10, 1H), 2.60 (dd, J=13, 5, 1H), 2.35 (s, 6H), 1.61 (s, 6H), 1.43 (d, J=6, 3H); LC-MS (LCT, 3.5 minutes) Rt=1.43 minutes; m/z (ESI) 410 (M+H).

Compound PAPC-A-09

(R)-5-((5-Cyclopropyl-4-(methylamino)pyridin-2-yl)amino)-3-((1-(dimethylamino)propan-2-yl)oxy)pyrazine-2-carbonitrile

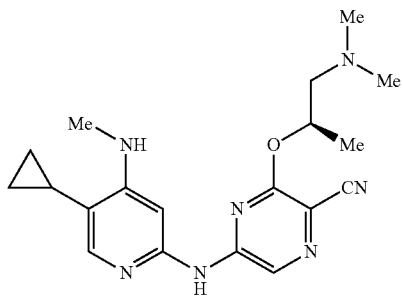 [SMILES: CNc1cc(Nc2cnc(C#N)c(O[C@H](C)CN(C)C)n2)ncc1C1CC1]

Prepared from Intermediate I-22 and Intermediate I-3 following General Procedure iii.

$^1$H NMR (500 MHz, CDCl$_3$) δ 8.11 (s, 1H), 7.71 (s, 1H), 6.91 (s, 1H), 5.39-5.37 (m, 1H), 4.92 (brs, 1H), 2.93-2.29 (m, 3H), 2.73-2.68 (m, 1H), 2.49 (dd, J=13.3, 3.9, 1H), 2.27 (s, 6H), 1.40-1.38 (m, 1H), 1.35 (d, J=6, 3H), 0.86-0.84 (m, 2H), 0.50-0.48 (m, 2H); LC-MS (LCT, 4 minutes) Rt=1.40 minutes; m/z (ESI) 368 (M+H).

Compound PAPC-A-10

(R)-Methyl 6-((5-cyano-6-((1-(dimethylamino)propan-2-yl)oxy)pyrazin-2-yl)amino)-4-(methylamino)nicotinate

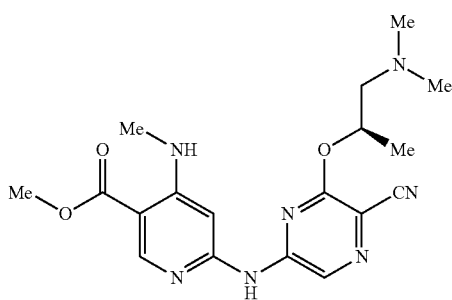 [SMILES: CNc1cc(Nc2cnc(C#N)c(O[C@H](C)CN(C)C)n2)ncc1C(=O)OC]

Prepared from Intermediate I-10 and Intermediate I-3 following General Procedure iii.

$^1$H NMR (500 MHz, CDCl$_3$) δ 8.68 (s, 1H), 8.26 (s, 1H), 8.15 (d, J=5, 1H), 7.03 (s, 1H), 5.50-5.39 (m, 1H), 3.88 (s, 3H), 2.97 (d, J=5, 3H), 2.78 (dd, J=13.4, 7.3, 1H), 2.55 (dd, J=13.4, 4.2, 1H), 2.34 (s, 6H), 1.42 (d, J=6.3, 3H); LC-MS (LCT, 3.5 minutes) Rt=1.84 minutes; m/z (ESI) 386 (M+H).

Compound PAPC-B-01

(R)-5-((4-Methoxy-5-(1-methyl-1H-pyrazol-4yl)pyridin-2-yl)amino)-3-(pyrrolidin-3-yloxy)pyrazine-2-carbonitrile

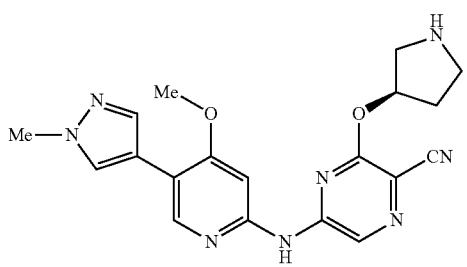 [SMILES: COc1cc(Nc2cnc(C#N)c(O[C@@H]3CCNC3)n2)ncc1-c1cnn(C)c1]

Prepared from Intermediate I-16 and Intermediate I-6 following General Procedure iv.

$^1$H NMR (500 MHz, d$_6$-DMSO) δ 8.51 (s, 1H), 8.45 (s, 1H), 8.13 (s, 1H), 7.93 (d, J=0.6, 1H), 7.60 (s, 1H), 5.61-5.56 (m, 1H), 3.98 (s, 3H), 3.88 (s, 3H), 3.23 (dd, J=12.7, 5.5, 1H), 3.06-2.97 (m, 2H), 2.94-2.87 (m, 1H), 2.16-2.09 (m, 1H), 1.99-1.92 (m, 1H); LC-MS (LCT, 3.5 minutes) Rt=2.02 minutes; m/z (ESI) 393 (M+H).

Compound PAPC-B-02

(R)-5-((4-Methoxy-5-(1-methyl-1H-pyrazol-4-yl)pyridin-2-yl)amino)-3-((1-methylpyrrolidin-3-yl)oxy)pyrazine-2-carbonitrile

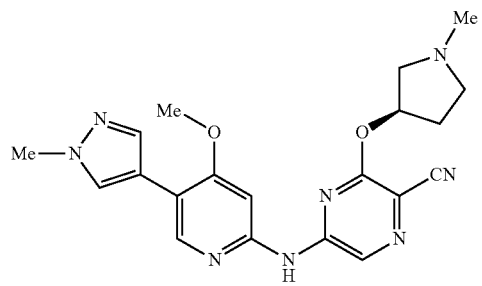 [SMILES: COc1cc(Nc2cnc(C#N)c(O[C@@H]3CCN(C)C3)n2)ncc1-c1cnn(C)c1]

Prepared from Intermediate I-16 and Intermediate I-4 following General Procedure iii.

$^1$H-NMR (500 MHz, CDCl$_3$) δ 8.39 (brs, 1H), 8.37 (s, 1H), 8.32 (s, 1H), 7.85 (s, 1H), 7.78 (s, 1H), 7.36 (s, 1H), 5.51-5.47 (m, 1H), 4.01 (s, 3H), 3.96 (s, 3H), 3.15 (dd, J=10.7, 6.3, 1H), 2.73-2.62 (m, 3H), 2.39 (s, 3H), 2.38-2.30 (m, 1H), 2.12-2.05 (m, 1H); LC-MS (LCT, 3.5 minutes) Rt=2.01 minutes; m/z (ESI) 407 (M+H).

Compound PAPC-B-03

(R)-5-((5-(1-Methyl-1H-pyrazol-4-yl)-4-(methylamino)pyridin-2-yl)amino)-3-(pyrrolidin-3-yloxy)pyrazine-2-carbonitrile

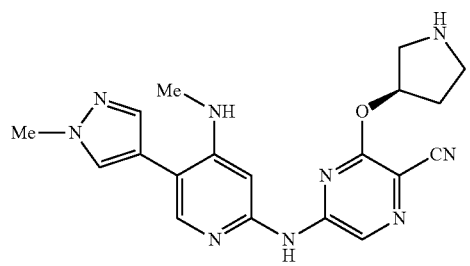 [SMILES: CNc1cc(Nc2cnc(C#N)c(O[C@@H]3CCNC3)n2)ncc1-c1cnn(C)c1]

Prepared from Intermediate I-15 and Intermediate I-6 following General Procedure iv.

$^1$H NMR (500 MHz, d$_6$-DMSO) δ 10.46 (brs, 1H), 8.50 (s, 1H), 7.89 (s, 1H), 7.84 (s, 1H), 7.60 (s, 1H), 7.04 (s, 1H), 5.84 (q, J=4.7, 1H), 5.61-5.55 (m, 1H), 3.88 (s, 3H), 3.25 (dd, J=12.7, 5.5, 1H), 3.07-3.00 (m, 2H), 2.93 (ddd, J=10.9, 8.1, 4.7, 1H), 2.78 (d, J=4.8, 3H), 2.17-2.10 (m, 1H), 2.01-1.93 (m, 1H); LC-MS (LCT, 3.5 minutes) Rt=1.24 minutes; m/z (ESI) 392 (M+H).

Compound PAPC-B-04

(S)-5-((5-(1-Methyl-1H-pyrazol-4-yl)-4-(methylamino)pyridin-2-yl)amino)-3-(pyrrolidin-3-yloxy)pyrazine-2-carbonitrile

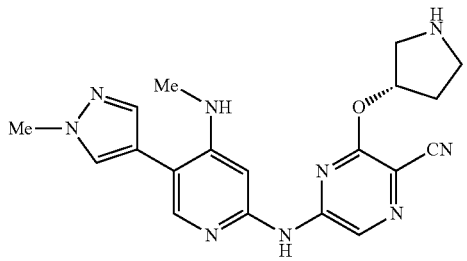 [SMILES: CNc1cc(Nc2cnc(C#N)c(O[C@H]3CCNC3)n2)ncc1-c1cnn(C)c1]

Prepared from Intermediate I-15 and Intermediate I-7 following General Procedure iv.

H NMR (500 MHz, d₆-DMSO) δ 10.46 (brs, 1H), 8.50 (s, 1H), 7.89 (s, 1H), 7.84 (s, 1H), 7.60 (s, 1H), 7.04 (s, 1H), 5.84 (q, J=4.7, 1H), 5.61-5.55 (m, 1H), 3.88 (s, 3H), 3.25 (dd, J=12.7, 5.5, 1H), 3.07-3.00 (m, 2H), 2.93 (ddd, J=10.9, 8.1, 4.7, 1H), 2.78 (d, J=4.8, 3H), 2.17-2.10 (m, 1H), 2.01-1.93 (m, 1H), LC-MS (LCT, 3.5 minutes) Rt=1.24 minutes; m/z (ESI) 392 (M+H).

Compound PAPC-B-05

(R)-5-((5-(1-Methyl-1H-pyrazol-4-yl)-4-(methylamino)pyridin-2-yl)amino)-3-((1-methylpyrrolidin-3-yl)oxy)pyrazine-2-carbonitrile

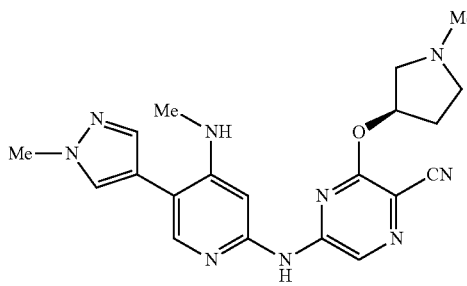

Prepared from Intermediate I-15 and Intermediate I-4 following General Procedure iii.

¹H NMR (500 MHz, CD₃OD) δ 8.49 (s, 1H), 7.82 (s, 1H), 7.78 (s, 1H), 7.61 (s, 1H), 6.85 (s, 1H), 5.62-5.60 (m, 1H), 3.97 (s, 3H), 3.05-3.02 (m, 1H), 2.88 (3H, s), 2.87-2.85 (m, 2H), 2.59-2.55 (m, 1H), 2.48-2.43 (m, 1H), 2.42 (s, 3H), 2.10-2.08 (m, 1H); LC-MS (LCT, 4 minutes) Rt=1.20 minutes; m/z (ESI) 406 (M+H).

Compound PAPC-B-06

(S)-5-((5-(1-Methyl-1H-pyrazol-4-yl)-4-(methylamino)pyridin-2-yl)amino)-3-((1-methylpyrrolidin-3-yl)oxy)pyrazine-2-carbonitrile

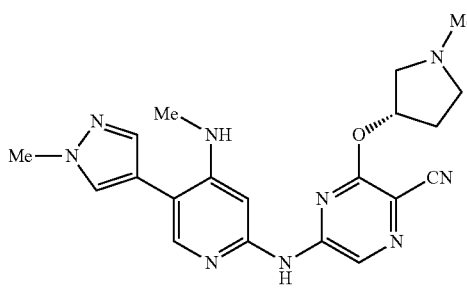

Prepared from Intermediate I-15 and Intermediate I-5 following General Procedure iii.

¹H NMR (500 MHz, CDCl₃) δ 8.33 (s, 1H), 7.86 (s, 1H), 7.59 (s, 1H), 7.50 (s, 1H), 6.98 (s, 1H), 5.56-5.54 (m, 1H), 4.78-4.77 (m, 1H), 4.00 (s, 3H), 3.29 (dd, J=11, 6.2, 1H), 2.92 (s, 3H), 2.80-2.78 (m, 1H), 2.74 (dd, J=11, 3.5, 1H), 2.47 (s, 3H), 2.41-2.37 (m, 1H), 2.16-2.14 (m, 1H); LC-MS (LCT, 4 minutes) Rt=1.20 minutes; m/z (ESI) 406 (M+H).

Compound PAPC-B-07

(R)-5-((5-(3-Hydroxy-3-methylbut-1-yn-1-yl)-4-methoxypyridin-2-yl)amino)-3-(pyrrolidin-3-yloxy)pyrazine-2-carbonitrile

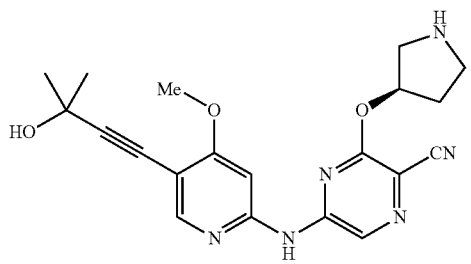 [SMILES: COc1cc(Nc2cnc(C#N)c(O[C@@H]3CCNC3)n2)ncc1C#CC(C)(C)O]

Prepared from Intermediate I-21 and Intermediate I-6 following General Procedure iv.

¹H NMR (500 MHz, d₆-DMSO) δ 8.51 (s, 1H), 8.21 (s, 1H), 7.47 (s, 1H), 5.62 (ddd, J=5.5, 5.5, 2.8, 1H), 5.41 (brs, 1H), 3.92 (s, 3H), 3.38 (dd, J=13, 5.3, 1H), 3.25 (d, J=13, 1H), 3.18-3.09 (m, 2H), 2.25-2.16 (m, 1H), 2.14-2.07 (m, 1H), 1.47 (s, 6H); LC-MS (LCT, 3.5 minutes) Rt=1.84 minutes; m/z (ESI) 395 (M+H).

Compound PAPC-B-08

(R)-5-((5-(3-Hydroxy-3-methylbut-1-yn-1-yl)-4-(methylamino)pyridin-2-yl)amino)-3-(pyrrolidin-3-yloxy)pyrazine-2-carbonitrile

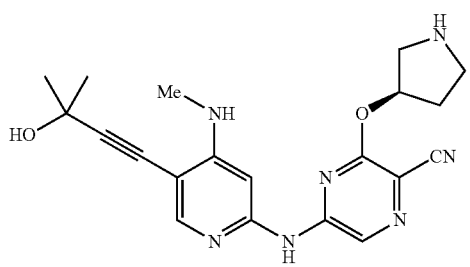 [SMILES: CNc1cc(Nc2cnc(C#N)c(O[C@@H]3CCNC3)n2)ncc1C#CC(C)(C)O]

Prepared from Intermediate I-20 and Intermediate I-6 following General Procedure iv.

¹H NMR (500 MHz, d₆-DMSO) δ 8.62 (s, 1H), 7.96 (s, 1H), 6.71 (s, 1H), 5.76 (brs, 1H), 3.49-3.48 (m, 2H), 3.45-3.35 (m, 1H), 2.95 (s, 3H), 2.35-2.32 (m, 2H), 1.60 (s, 6H) (2H obscured by water); LC-MS (LCT, 4 minutes) Rt=1.59 minutes; m/z (ESI) 394 (M+H).

Compound PAPC-B-09

(R)-Methyl 6-((5-cyano-6-(pyrrolidin-3-yloxy)pyrazin-2-yl)amino)-4-(methoxy)nicotinate

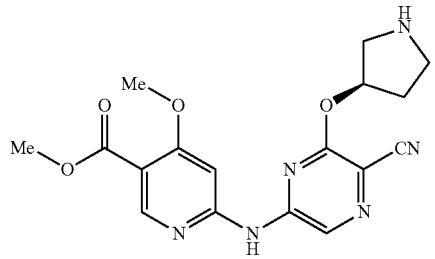 [SMILES: COC(=O)c1cnc(Nc2cnc(C#N)c(O[C@@H]3CCNC3)n2)cc1OC]

Prepared from Intermediate I-11 and Intermediate I-6 following General Procedure iv.

$^1$H NMR (500 MHz, d$_6$-DMSO) δ 8.63 (s, 1H), 8.54 (s, 1H), 7.56 (s, 1H), 5.62-5.60 (m, 1H), 3.94 (s, 3H), 3.79 (s, 3H), 3.18-2.98 (m, 4H), 2.21-2.12 (m, 1H), 2.07-1.99 (m, 1H); LC-MS (LCT, 3.5 minutes) Rt=2.04 minutes; m/z (ESI) 371 (M+H).

Compound PAPC-B-10

(R)-Methyl 6-((5-cyano-6-(pyrrolidin-3-yloxy)pyrazin-2-yl)amino)-4-(methylamino)nicotinate

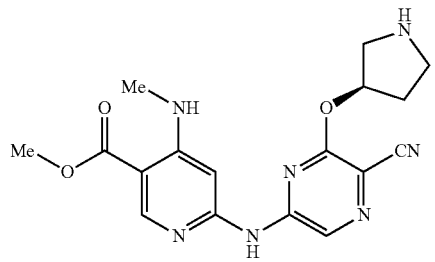 [SMILES: CNc1cc(Nc2cnc(C#N)c(O[C@@H]3CCNC3)n2)ncc1C(=O)OC]

Prepared from Intermediate I-10 and Intermediate I-6 following General Procedure iv.

$^1$H NMR (500 MHz, d$_6$-DMSO) δ 8.58 (s, 1H), 8.38 (s, 1H), 8.01 (q, J=4.7, 1H), 7.22 (s, 1H), 5.62-5.51 (m, 1H), 3.81 (s, 3H), 3.18 (dd, J=12.6, 5.5, 1H), 3.01-2.92 (m, 2H), 2.90 (d, J=4.9, 3H), 2.85 (ddd, J=10.8, 8.0, 4.8, 1H), 2.14-2.03 (m, 1H), 1.95-1.87 (m, 1H); LC-MS (LCT, 3.5 minutes) Rt=1.64 minutes; m/z (ESI) 370 (M+H).

Compound PAPC-B-11

(R)-Methyl 6-((5-cyano-6-(pyrrolidin-3-yloxy)pyrazin-2-yl)amino)-4-(dimethylamino)nicotinate

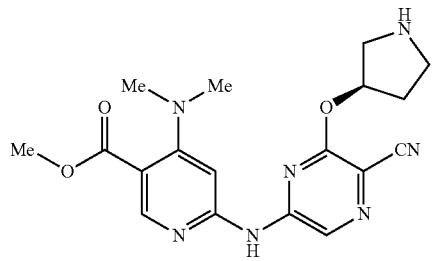 [SMILES: COC(=O)c1cnc(Nc2cnc(C#N)c(O[C@@H]3CCNC3)n2)cc1N(C)C]

Prepared from Intermediate I-12 and Intermediate I-6 following General Procedure iv.

$^1$H NMR (500 MHz, d$_6$-DMSO) δ 8.56 (s, 1H), 8.35 (s, 1H), 7.20 (s, 1H), 5.68-5.59 (m, 1H), 3.81 (s, 3H), 3.39 (dd, J=13.1, 5.2, 1H), 3.31 (bs, 1H), 3.27 (d, J=13.1, 1H), 3.19-3.12 (m, 2H), 2.91 (s, 6H), 2.23-2.18 (m, 1H), 2.15-2.08 (m, 1H); LC-MS (LCT, 3.5 minutes) Rt=1.70 minutes; m/z (ESI) 384 (M+H).

Biological Methods

Assay 1A: Determination of Inhibitor Potency vs. CHK1 in DELFIA Assay Format

CHK1 kinase function was measured in a DELFIA® assay in order to monitor phosphorylation of a CDC25C peptide using a specific phospho antibody. The enzyme reaction was carried out in polypropylene plates (Greiner) using a reaction mix (25 µL) containing enzyme and peptide mix (CHK1, 1 nM; Biotin-KKKVSRSGLYRSPSMPENLNRPR, 1 µM or 15 µL), ATP (30 µM or 5 µL) and either DMSO (2.5%) or test compound (5 µL) diluted to a give a range of concentrations (from 0 to 100 µM in 2.5% DMSO, final concentrations) in assay buffer (40 mM Tris, 40 mM NaCl, 2 mM MgCl$_2$, 1 mM DTT and 0.1% Tween 20). The reaction mixture was incubated for 30 minutes at room temperature and then stopped by the addition of buffer (125 µL) containing 40 mM EDTA, 0.05% Tween 20, 0.1% BSA in TBS (10× concentrate, Sigma). An aliquot (100 µL) of the stopped reaction mixture was transferred to a black neutravidin-coated plate (Perbio) and incubated for 1 hour on a shaker (Titertek, Flow Laboratories) at room temperature. The plates were washed four times with wash buffer (25 mM Tris (pH 8), 150 mM NaCl, and 0.1% Tween 20) (WellWash4, Thermo Life Sciences) and incubated for 1 hour as before with an antibody mixture (100 µL) consisting of anti-phospho CDC25C (1.25 nM, #9528, Cell Signalling Technology) and europium-labelled anti-rabbit IgG (0.3 µg/mL, AD0105, PerkinElmer Life Sciences) diluted in DELFIA assay buffer (PerkinElmer Life Sciences). The plates were washed a further four times with wash buffer before the addition of enhancement solution (100 µL/well, PerkinElmer Life Sciences). The plate was read on a Victor2 1420 multilabel counter (Perkin Elmer Life Sciences) using a time-resolved measurement mode reading fluorescence at 615 nm. The concentration of test compound required to inhibit enzyme activity by 50% was calculated (IC$_{50}$).

Assay 1B: Determination of Inhibitor Potency Vs. CHK1 in Caliper Assay Format

CHK1 kinase activity was measured in a microfluidic assay that monitors the separation of a phosphorylated product from its substrate. The assay was run on an EZ Reader II (Caliper Life Sciences Ltd, Runcorn, UK) using separation buffer (#760367 Caliper LS) containing CR-8 (500 nM, #760278, Caliper LS). An ECHO® 550 (Labcyte Inc™) acoustic dispenser was used to generate duplicate 8 pt dilution curves directly into 384 polypropylene assay plates (Greiner Bio-One, Gloucestershire, UK). For each test compound a 50 µM stock concentration in 100% DMSO was used. The total amount of DMSO dispensed per well was 250 nL to give a final assay concentration of 2.5% DMSO and test compound concentrations in the range 0.5-1000 nM. To this assay plate, 6 µL CHK1 (2 nM final concentration, in-house protein preparation), 2 µL peptide 10 (5-FAM-KKKVSRSGLYR-SPSMPENLNRPR-COOH, 1.5 µM final concentration, #760354 Caliper LS) and 2 µL ATP (90 µM final concentration) all diluted in kinase buffer (HEPES 50 mM, NaN$_3$ 0.02%, BSA 0.01%, sodium orthovanadate 0.1 mM, DTT 1 mM, MgCl$_2$ 2 mM, Tween 20 0.1%) were added. The plate was sealed and centrifuged (1 minutes, 1000 rpm) before incubation for one hour at room temperature. The reaction was stopped by the addition of separation buffer (90 µL). The plate was read on an EZ Reader II, using a 12-sipper chip (760137-0372R, Caliper LS) with instrument settings of −1.5 psi and 1750 ΔV. The percentage conversion of product from substrate was generated automatically and the percentage inhibition was calculated relative to blank wells (containing no enzyme and 2.5% DMSO) and total wells (containing all reagents and 2.5% DMSO). $IC_{50}$ values were calculated in GraphPad Prism5 using a non linear regression fit of the log (inhibitor) vs. response with variable slope equation.

Assay 2: Determination of Inhibitor Selectivity for Inhibition of CHK1 vs. CHK2

In vitro CHK2 kinase activity was measured in a DELFIA® assay that monitors phosphorylation of a CDC25C peptide using a specific phospho antibody. The enzyme reaction was carried out in 96-well polypropylene plates (Greiner). The reaction mix (total volume 25 μL) contained enzyme and peptide mix (15 μL) (containing CHK2, prepared in-house, 1 nM; Biotin-KKKVSRSGLYR-SPSMPENLNRPR, 1 μM), ATP (30 μM, 5 μL) and either DMSO (2.5%) or test compound (5 μL) diluted to a give a range of concentrations (0-100 μM in 2.5% DMSO, final concentrations) in assay buffer (40 mM HEPES (pH 7.4), 40 mM KCl, 2 mM $MgCl_2$, 10 mM DTT and 0.02% Tween 20). The reaction mixture was incubated for 30 minutes at room temperature and stopped by the addition of buffer (125 μL) containing 40 mM EDTA, 0.05% Tween 20, 0.1% BSA in TBS (10× concentrate, Sigma). An aliquot (100 μL) of the reaction mix was transferred to a black neutravidin-coated 96-well plate (Perbio) and incubated for 1 hour on a shaker (Titertek, Flow Laboratories) at room temperature. The plates were washed four times with wash buffer (25 mM Tris (pH 8), 150 mM NaCl and 0.1% Tween 20) (WellWash4, Thermo Life Sciences) and incubated for 1 hour as before with antibody mix (100 μL) consisting of anti-phospho CDC25C (diluted 1/4000 equivalent to 0.35 nM-1.25 nM, #9528, Cell Signalling Technology) and europium-labelled anti rabbit IgG, (0.3 μg/mL, AD0105, PerkinElmer Life Sciences) diluted in DELFIA® assay buffer (PerkinElmer Life Sciences). The plates were washed a further four times with wash buffer before the addition of enhancement solution (100 μL/well, PerkinElmer Life Sciences). The plate was read on a Victor2 1420 multi label counter (PerkinElmer Life Sciences) using a time-resolved measurement mode reading fluorescence at 615 nM. The concentration of test compound required to inhibit enzyme activity by 50% was calculated ($IC_{50}$).

For each test compound, the ratio of the $IC_{50}$ from the CHK2 kinase activity assay to the $IC_{50}$ from the CHK1 kinase activity assay (i.e., CHK2 $IC_{50}$/CHK1 $IC_{50}$) was used to define the selectivity for inhibition of CHK1 vs. CHK2.

Assay 3: Mitosis Inhibition Assay (MIA)

Checkpoint abrogation by CHK1 kinase function inhibitors in combination with genotoxic agents was assessed using a europium based ELISA assay designed to quantify the number of cells trapped in mitosis after treatment with a genotoxic agent (to induce G2 arrest) followed by a test compound in combination with nocodazole to abrogate this arrest. HT29 cells were seeded at 104 cells per well into 96-well plates in a volume of 160 μL and left to attach for 36 hours. Etoposide (10 mM stock in DMSO) was diluted in medium to 250 μM and then 40 μL was added to appropriate wells to give a final concentration of 50 μM and incubated for 1 hour. This treatment had previously been optimised to induce a G2 arrest in 80% of cells 16 hours following treatment. After genotoxic drug exposure, the medium was removed and replaced with fresh medium (160 μL). Cells were either untreated (untreated control or etoposide pretreatment alone), exposed to nocodazole following etoposide pre treatment or nocodazole alone (100 ng/mL final concentration), or exposed to increasing concentrations of test compound (from 200 μM to 0.01 nM final concentration) in combination with nocodazole (100 ng/mL final concentration). Test compounds were added in 40 μL aliquots using quadruplicate wells for each dose. After 21 hours exposure, the medium was removed and cells were fixed in 4% formaldehyde in phosphate buffered saline (PBS, pH 7.4, pre-cooled to 4° C.) for 30 minutes at 4° C., followed by 100% methanol (pre-cooled to −20° C.) for 10 minutes at ambient temperature. Wells were washed with PBS and blocked with 5% dried milk (Marvel) in Tris-buffered saline (TBS, pH 7.4) at 37° C. for 30 minutes. Each well was washed three times with water containing 0.1% Tween 20. Primary antibody (MPM-2, Upstate cat#05-368, 1 μg/mL in 5% milk in TBS) was added to each well and incubated overnight with shaking at 4° C. Primary antibody was removed and wells were washed with water containing 0.1% Tween 20. The secondary antibody (europium labelled anti-mouse, Perkin-Elmer cat# AD0124, 333 ng/mL in assay buffer Perkin-Elmer cat#1244-111) was added to each well and incubated at 37° C. for 1 hour. Each well was washed with water 0.1% containing Tween 20 and treated with enhancement solution (Perkin-Elmer cat#1244-105). Europium emissions were counted on a Wallac, Victor2 counter (Perkin-Elmer, Bucks UK). Appropriate controls were included and results were expressed as the concentration of test compound required to allow 50% of cells to enter mitosis (MIA $IC_{50}$).

Estimation of Comparative Oral Bioavailability by Limited Sampling In Vivo Pharmacokinetics Female BALB/c mice (6 weeks old) (Charles River UK Ltd, Margate, UK) were kept in a controlled environment with food and sterilized water available ad libitum. Animals weighed 20±2 g at the time of experiment. All procedures were conducted in accordance with the local and national guidelines for animal experimentation. Dosing solutions were prepared by dissolving the test compounds in 10% DMSO and 5% Tween 20 in 85% saline. Test compounds were administered orally (p.o.) by oral gavage. Blood was collected at selected time points by cardiac puncture under anaesthesia into heparinized syringes, transferred to microcentrifuge tubes, and centrifuged at 4500×g for 2 minutes to obtain plasma. Quantitative analysis was performed by high performance liquid chromatography tandem mass spectrometry on a triple quadrupole instrument (Agilent 6410) using multiple reaction monitoring of selected transitions with olomoucine used as internal standard. Quantitation was performed against a standard curve ranging from concentrations of 2 nM to 1000 nM in the matrix measured. Quality controls were included at the level of 25, 250 and 750 nM. If required, samples were diluted in the matrix of interest. The plasma concentrations of test compounds were measured at 1 hour after oral dose and expressed relative to a 10 mg/kg dose to provide a comparative estimate of the degree of oral bioavailability.

Biological Data

CHK1 Activity

The following compounds were tested using Assay 1A (Determination of inhibitor potency vs. CHK1 in DELFIA assay format) or Assay 1B (Determination of inhibitor potency vs. CHK1 in Caliper assay format):

PAPC-A-01, PAPC-A-02, PAPC-A-03, PAPC-A-04, PAPC-A-05, PAPC-A-06, PAPC-A-07, PAPC-A-08, PAPC-A-09, PAPC-A-10, PAPC-B-01, PAPC-B-02, PAPC-B-03, PAPC-B-04, PAPC-B-05, PAPC-B-06, PAPC-B-07, PAPC-B-08, PAPC-B-09, PAPC-B-10, PAPC-B-11.

All of the compounds have a CHK1 $IC_{50}$ of less than 0.1 μM (100 nM).

The following compounds have a CHK1 $IC_{50}$ of less than 0.02 μM (20 nM):

PAPC-A-01, PAPC-A-02, PAPC-A-03, PAPC-A-08, PAPC-A-10, PAPC-B-01, PAPC-B-02, PAPC-B-03, PAPC-B-04, PAPC-B-05, PAPC-B-06, PAPC-B-08, PAPC-B-10, PAPC-B-11,

Selectivity for CHK1 vs. CHK2

The following compounds were also tested using Assay 2 (Determination of inhibitor selectivity for inhibition of CHK1 vs. CHK2):

PAPC-A-01, PAPC-A-02, PAPC-A-03, PAPC-A-07, PAPC-A-08, PAPC-A-09, PAPC-B-02, PAPC-B-03, PAPC-B-04, PAPC-B-06, PAPC-B-10, PAPC-B-11.

All of the compounds have a CHK1 vs. CHK2 selectivity of at least 100-fold (i.e., CHK2 $IC_{50}$/CHK1 $IC_{50}$>100).

MIA Activity

The following compounds were tested using Assay 3 (Mitosis Inhibition Assay (MIA)):

PAPC-A-01, PAPC-A-02, PAPC-A-03, PAPC-A-04, PAPC-A-05, PAPC-A-06, PAPC-A-07, PAPC-A-08, PAPC-A-09, PAPC-A-10, PAPC-B-01, PAPC-B-02, PAPC-B-03, PAPC-B-04, PAPC-B-05, PAPC-B-06, PAPC-B-07, PAPC-B-08, PAPC-B-09, PAPC-B-10, PAPC-B-11.

The following compounds have a MIA $IC_{50}$ of less than 0.5 µM:

PAPC-A-01, PAPC-A-02, PAPC-A-03, PAPC-A-04, PAPC-A-05, PAPC-A-06, PAPC-A-07, PAPC-A-08, PAPC-A-09, PAPC-A-10, PAPC-B-01, PAPC-B-02, PAPC-B-03, PAPC-B-04, PAPC-B-05, PAPC-B-06, PAPC-B-08, PAPC-B-10, PAPC-B-11.

Oral Bioavailability

The following compounds were evaluated for oral bioavailability using the method described above:

PAPC-A-01, PAPC-A-02, PAPC-A-05, PAPC-A-07, PAPC-A-09, PAPC-B-01, PAPC-B-02, PAPC-B-03, PAPC-B-04, PAPC-B-05, PAPC-B-06, PAPC-B-08, PAPC-B-10.

All of the compounds have oral bioavailability (plasma concentration, 1 hour following 10 mg/kg p.o.) of at least 2 nM.

The following compounds have oral bioavailability (plasma concentration, 1 hour following 10 mg/kg p.o.) of at least 10 nM.

PAPC-A-01, PAPC-A-02, PAPC-A-05, PAPC-A-07, PAPC-A-09, PAPC-B-02, PAPC-B-05, PAPC-B-06, PAPC-B-08, PAPC-B-10.

The following compounds have oral bioavailability (plasma concentration, 1 hour following 10 mg/kg p.o.) of at least 100 nM.

PAPC-A-01, PAPC-A-02, PAPC-A-05, PAPC-A-07, PAPC-B-02, PAPC-B-05:

The following compounds have oral bioavailability (plasma concentration, 1 hour following 10 mg/kg p.o.) of at least 500 nM.

PAPC-A-01, PAPC-A-02, PAPC-A-05.

Data for two especially preferred compounds are summarized below:

| Compound | PAPC-A-01 | PAPC-A-02 |
|---|---|---|
| Structure | (structure) | (structure) |
| CHK1 $IC_{50}$ (µM) | 0.006 | 0.008 |
| CHK1 vs. CHK2 selectivity | 540-fold | >1250-fold |
| MIA $IC_{50}$ (µM) | 0.0273 | 0.029 |
| Oral bioavail. (plasma concentration, 1 hour following 10 mg/kg p.o.) (nM) | 555 | 1214 |

In Vivo Study 1: PAPC-A-01 in Transgenic MYCN-Driven Neuroblastoma Model

Spontaneous neuroblastomas arising in hemizygous mice transgenic for TH-MYCN (human MYCN under the control of the rat tyrosine hydroxylase promoter) were detected by abdominal palpation. Sequential animals with well-established tumours (30-70 days of age) were randomised to receive either test compound (PAPC-A-01) or vehicle until 8-9 mice per group were accrued. The test compound (PAPC-A-01) was administered as a single agent at 100 mg/kg p.o. daily for 7 consecutive days by oral gavage (100 µL/10 g body weight) and controls received an equivalent volume of vehicle (10% DMSO, 5% Tween 20, 85% saline). Neuroblastoma size was assessed by MRI and by the mass of tumours dissected from the abdominal cavity at the end of therapy.

[1]H MRI was performed on a 7T Bruker horizontal bore microimaging system (Bruker Instruments, Ettlingen, Germany) using a 3 cm birdcage coil. Anaesthesia was induced a combination of fentanyl citrate (0.315 mg/mL) plus fluanisone (10 mg/mL) (Hypnorm, Janssen Pharmaceutical, Oxford, UK) and midazolam (5 mg/mL) (Roche, Welwyn Garden City, UK) and water (1:1:2). Animal body temperature was maintained by a warm air blower through the magnet bore.

Figure 2:
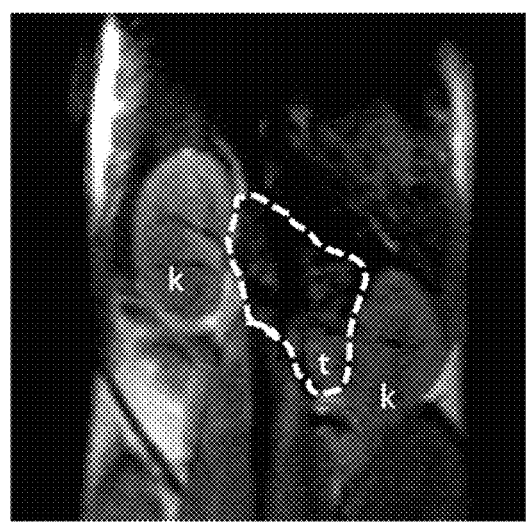
FIG. 2 is an MRI scan recorded as part of the in vivo study ("PAPC-A-01 in Transgenic MYCN-driven Neuroblastoma Model") described below. The image shows the abdomen of a mouse (k=kidney; t=tumour; s.b.=small bowel) and was recorded following 7 days treatment with PAPC-A-01. The tumour volume was 417 mm$^3$.

Anatomical $T_2$-weighted coronal and transverse images were acquired from twenty contiguous 1 mm-thick coronal slices through the mouse abdomen, using a rapid acquisition with refocused echoes (RARE) sequence with 4 averages of 128 phase encoding steps over a 3×3 cm field of view, two echoes of 36 and 132 ms, a TR of 4.5 s and a RARE factor of 8. Following MRI, the mice were left to recover on a heat mat for 24 hours. Tumour volumes were measured using segmentation from regions of interest drawn on every slice from the coronal $T_2$ weighted images containing tumour using in-house software (ImageView, working under IDL, ITT, Boulder, Colo., USA). MR imaging in individual mice, pre-treatment and on day 7, showed tumour regression over the 7 day treatment period. See FIG. 1 and FIG. 2.

The mean weight of tumours in control mice at the end of the study was 2.1±0.7 g (mean±SD) and in the treated group was 0.3±0.2 g, resulting in a T/C of 13.4%.

In Vivo Study 2: PAPC-A-01 in Combination with Gemcitabine in HT29 Human Colon Carcinoma Xenograft Female athymic CrTac:NCr-Foxn1nu mice (6-8 weeks old) (Charles River UK Ltd., Margate, UK) were kept in a controlled environment in maximiser cages with sterile bedding, food and water available ad libitum. Animals weighed 20.3±2.0 g at the start of the study. Handing and all experimental procedures were performed under sterile conditions in laminar flow hoods in accordance with UK Home Office, national and local ethical guidelines.

HT29 colon carcinoma cells from the American Type Culture Collection (ATCC, LGC Promochem, Middesex, UK) were harvested from tissue culture flasks and injected subcutaneously in the right flanks of mice (3 million cells per site). Once tumours were established (mean diameter 0.55±0.05 cm) mice were randomised to treatment groups (n=6) to receive (a) test compound (PAPC-A-01) (75 mg/kg), (b) gemcitabine (100 mg/kg), (c) a combination (PAPC-A-01) (75 mg/kg) and gemcitabine (100 mg/kg), or (d) relevant vehicles.

Clinical grade gemcitabine hydrochloride (GEMZAR, Eli Lilly, Newmarket, UK) was reconstituted in sterile 0.9% sodium chloride and aliquots frozen at −20° C. Gemcitabine was administered intravenously once weekly via a lateral tail vein on days 0 (day 5 after tumour cell implantation), 7 and 14. Test compound (PAPC-A-01) was dissolved in 10% DMSO and diluted out in 5% Tween 20, 85% saline. Test compound (PAPC-A-01) was administered by oral gavage on days 1, 2, 8, 9, 15 and 16. The control animals received both vehicles by the appropriate route on the designated days. The compounds were administered in a volume of 100 µL per 10 g body weight.

Animals were observed daily and body weights and tumours measured three times weekly. Two perpendicular tumour diameters were used to calculate volumes using the formula: $V=4/3\pi[(d1+d2)/4]^3$.

T/C values (volumes of treated tumours vs. controls) were calculated with respect to vehicle control tumours or those treated with gemcitabine alone, expressed as a percentage.

On day 24 after the start of therapy, the results were as follows:

| Group | Mean tumour volume (cm³, mean ± SEM) | T/C vs. vehicle controls | T/C vs. gemcitabine |
| --- | --- | --- | --- |
| Vehicle controls | 1.099 ± 0.304 | — | — |
| Gemcitabine | 0.888 ± 0.188 | 80.8 | — |
| PAPC-A-01 | 1.114 ± 0.257 | 101.4 | — |
| Combination | 0.406 ± 0.066 | 36.9 | 45.7 |

Gemcitabine alone, at close to the recommended maximum tolerated dose, inhibited tumour growth by approximately 20%. Test compound (PAPC-A-01) alone gave no growth inhibition. The combination therapy of gemcitabine with test compound (PAPC-A-01) inhibited tumour growth by 63% relative to controls, and by 54% relative to gemcitabine alone.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Almeida et al., 2008, "Pyrazolyl-amino-substituted pyrazines and their use for the treatment of cancer", international (PCT) patent publication number WO 2008/117050 A1 published 2 Oct. 2008.

Balaint and Vousden, 2001, "Activation and activities of the p53 tumour suppressor protein," *Br. J. Cancer,* Vol. 85, pp. 1813-1823.

Bartek and Lukas, 2003, "Chk1 and Chk2 kinases in checkpoint control and cancer," *Cancer Cell,* Vol. 3, pp. 421-429.

Brooks et al., 2012, "A potent chk1 inhibitor is selectively toxic in melanomas with high levels of replicative stress," *Oncogene, doi:*10.1038/onc.2012.72.

Carson and Lois, 1995, "Cancer progression and p53," *Lancet,* Vol. 346, pp. 1009-1011.

Cavelier et al., 2009, "Constitutive activation of the DNA damage signaling pathway in acute myeloid leukemia with complex karyotype: Potential importance for checkpoint targeting therapy," *Cancer Res.,* Vol. 69, pp. 8652-8661.

Cole et al., 2011 "RNAi screen of the protein kinome identifies checkpoint kinase 1 (chk1) as a therapeutic target in neuroblastoma," Proc. Natl. Acad. Sci. U.S.A., Vol. 108, pp. 3336-3341.

Collins et al., 2009a, "Pyrazin-2-yl-2-yl-amine and pyrazin-2-yl-pyrimidin-4-yl-amine compounds and their use", international (PCT) patent publication number WO 2009/044162 A1 published 9 Apr. 2009.

Collins et al., 2009b, "Bicyclylaryl-aryl-amine compounds and their use", international (PCT) patent publication number WO 2009/103966 A1 published 27 Aug. 2009.

Davies et al., 2011, "Single-agent inhibition of chk1 is anti-proliferative in human cancer cell lines in vitro and inhibits tumor xenograft growth in vivo," *Oncol. Res.,* Vol. 19, pp. 349-363.

Di Micco et al., 2006, "Oncogene-induced senescence is a DNA damage response triggered by DNA hyper-replication," *Nature*, Vol. 444, pp. 638-642.

Dixon and Norbury, 2002, "Therapeutic exploitation of checkpoint defects in cancer cells lacking p53 function," *Cell Cycle*, Vol. 1, pp. 362-368.

Ferrao et al., 2011, "Efficacy of chk inhibitors as single agents in myc-driven lymphoma cells," *Oncogene*, doi:10.1038/onc.2011.358.

Greenblatt et al., 1994, "Mutations in the p53 tumor suppressor gene: clues to cancer etiology and molecular pathogenesis," *Cancer Res.*, Vol. 54, pp. 4855-4878.

Guzi et al., 2011, "Targeting the replication checkpoint using SCH 900776, a potent and functionally selective CHK1 inhibitor identified via high content screening," *Mol. Cancer Ther.*, Vol. 10, pp. 591-602.

Höglund et al., 2011, "Therapeutic Implications for the Induced Levels of Chk1 in Myc-Expressing Cancer Cells," *Clin. Cancer Res.*, Vol. 17, pp. 7067-7079.

Ioannidis et al., 2009, "Discovery of pyrazol-3-ylamino pyrazines as novel JAK2 inhibitors", *Bioorg. Med. Chem. Lett.*, Vol. 19, pp. 6524-6528.

Lainchbury et al., 2012, "Discovery of 3-akloxyamino-5-(pyridin-2-ylamino)pyrazine-2-carbonitriles as selective, orally bioavailable CHK1 inhibitors", *J. Med. Chem.*, apparently published online on 19 Oct. 2012, dx.doi.org/10.1021/jm3012933.

Li et al., 2007, "Synthesis and in-vitro biological activity of macrocyclic urea CHK1 inhibitors", *Bioorg. Med. Chem. Lett.*, Vol. 17, pp. 6499-6504.

Lin et al., 2005, "Macrocyclic kinase inhibitors", US patent publication number US 2005/0215556 A1 published 29 Sep. 2005.

Liu et al., 2000, "Chk1 is an essential kinase that is regulated by Atr and required for the G(2)/M DNA damage checkpoint," *Genes Dev.*, Vol. 14, pp. 1448-1459.

Murga et al., 2011, "Exploiting oncogene-induced replicative stress for the selective killing of Myc-driven tumors," *Nat. Struct. Mol. Biol.*, Vol. 18, pp. 1331-1335.

Sanchez et al., 1997, "Conservation of the Chk1 checkpoint pathway in mammals: linkage of DNA damage to Cdk regulation through Cdc25," *Science*, Vol. 277, pp. 1497-1501.

Sorensen et al., 2005, "Cell-cycle checkpoint kinase Chk1 is required for mammalian homologous recombination repair," *Nat. Cell Biol.*, Vol 7, pp. 195-201.

Tao et al., 2005, "Macrocyclic kinase inhibitors", international (PCT) patent publication number WO 2005/047294 A1 published 26 May 2005.

Tao et al., 2006, "Chk1 inhibitors for novel cancer treatment," *Anti-Cancer Agents in Medicinal Chemistry*, Vol. 6, pp. 377-388.

Tao et al., 2007a, "Macrocyclic ureas as potent and selective CHK1 inhibitors: an improved synthesis, kinome profiling, structure-activity relationships, and preliminary pharmacokinetics," *Bioorg. Med. Chem. Lett.*, Vol. 17, pp. 6593-6601.

Tao et al., 2007b, "Structure-based design, synthesis, and biological evaluation of potent and selective macrocyclic checkpoint kinase 1 inhibitors," *J. Med. Chem.*, Vol. 50, pp. 1514-1527.

Walton et al., 2010, "The preclinical pharmacology and therapeutic activity of the novel CHK1 inhibitor SAR-020106," *Mol. Cancer Ther.*, Vol. 9, No. 1, pp. 89-100.

Walton et al., 2012, "CCT244747 is a novel potent and selective CHK1 inhibitor with oral efficacy alone and in combination with genotoxic anticancer drugs", *Clin. Cancer Research*, Vol. 18, No. 20, pp. 5650-5661.

Wang et al., 1996, "UCN-01: a potent abrogator of G2 checkpoint function in cancer cells with disrupted p53," *J. Natl. Cancer Inst.*, Vol. 8, pp. 956-965.

Weinert and Hartwell, 1989, "Control of G2 delay by the rad9 gene of *Saccharomyces cerevisiae*," *J. Cell Sci. Suppl.*, Vol. 12, pp. 145-148.

Xiao et al., 2006, "Differential roles of checkpoint kinase 1, checkpoint kinase 2, and mitogen-activated protein kinase-activated protein kinase 2 in mediating DNA damage-induced cell cycle arrest: implications for cancer therapy," *Mol. Cancer Ther.*, Vol. 5, pp. 1935-1943.

Zachos et al., 2003, "Chk1-deficient tumour cells are viable but exhibit multiple checkpoint and survival defects," *EMBO J.*, Vol. 22, pp. 713-723.

Zhao et al., 2002, "Disruption of the checkpoint kinase 1/cell division cycle 25A pathway abrogates ionizing radiation-induced S and G2 checkpoints," *Proc. Natl. Acad. Sci. USA*, Vol. 99, pp. 14795-14800.

The invention claimed is:

1. A method of treatment of lymphoma or leukemia comprising administering to a subject in need of treatment a therapeutically-effective amount of a compound of the following formula, or a pharmaceutically acceptable salt thereof:

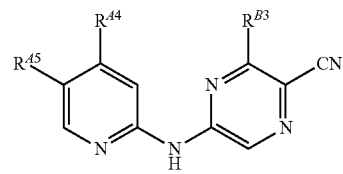

wherein:
—$R^{B3}$ is independently:

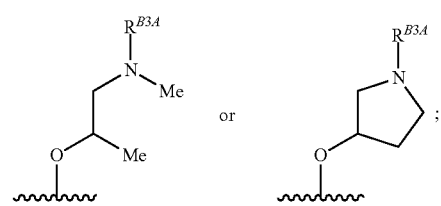

each —$R^{B3A}$ is independently —H or saturated aliphatic $C_{1-3}$alkyl;
—$R^{A4}$ is independently —NHR$^{A4A}$, —NR$^{A4A}_2$, or —OR$^{A4A}$;
each —$R^{A4A}$ is independently saturated aliphatic $C_{1-3}$alkyl;
—$R^{A5}$ is independently —$R^{A5A}$, —$R^{A5B}$, —$R^{A5C}$, —$R^{A5D}$, —$R^{A5E}$, or —$R^{A5F}$;
—$R^{A5A}$ is independently:

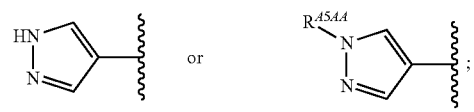

—$R^{A5AA}$ is saturated aliphatic $C_{1-3}$alkyl;
—$R^{A5B}$ is —$CF_3$;

—$R^{A5C}$ is independently —F, —Cl, —Br, or —I;
—$R^{A5D}$ is independently —C≡CH, —C≡C—$R^{A5DA}$, or —C≡C—$R^{A5DB}$—OH;
—$R^{A5DA}$ is saturated aliphatic $C_{1-4}$alkyl;
—$R^{A5DB}$ is saturated aliphatic $C_{1-4}$alkylene;
—$R^{A5E}$ is independently saturated $C_{3-6}$cycloalkyl;
—$R^{A5F}$ is —C(=O)O-13 $R^{A5FA}$; and
—$R^{A5FA}$ is saturated aliphatic $C_{1-3}$alkyl.

2. The method according to claim 1, wherein —$R^{B3}$ is:

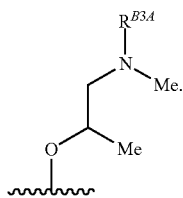

3. The method according to claim 1, wherein —$R^{B3}$ is:

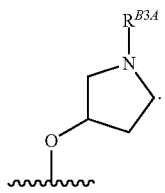

4. The method according to claim 1, wherein —$R^{B3A}$ is —H or -Me.

5. The method according to claim 2, wherein —$R^{B3A}$ is -Me.

6. The method according to claim 3, wherein —$R^{B3A}$ is —H or -Me.

7. The method according to claim 4, wherein —$R^{A4}$ is independently —$NHR^{A4A}$ or —$NR^{A4A}_2$; wherein each —$R^{A4A}$ is independently -Me or -Et.

8. The method according to claim 5, wherein —$R^{A4}$ is independently —$NHR^{A4A}$ or —$NR^{A4A}_2$; wherein each —$R^{A4A}$ is independently -Me or -Et.

9. The method according to claim 6, wherein —$R^{A4}$ is independently —$NHR^{A4A}$ or —$NR^{A4A}_2$; wherein each —$R^{A4A}$ is independently -Me or -Et.

10. The method according to claim 4, wherein —$R^{A4}$ is —$OR^{A4A}$; wherein each —$R^{A4A}$ is independently -Me or -Et.

11. The method according to claim 5, wherein —$R^{A4}$ is —$OR^{A4A}$; wherein each —$R^{A4A}$ is independently -Me or -Et.

12. The method according to claim 6, wherein —$R^{A4}$ is —$OR^{A4A}$; wherein each —$R^{A4A}$ is independently -Me or -Et.

13. The method according to claim 1, wherein —$R^{A5}$ is —$R^{A5A}$.

14. The method according to claim 2, wherein —$R^{A5}$ is —$R^{A5A}$.

15. The method according to claim 3, wherein —$R^{A5}$ is —$R^{A5A}$.

16. The method according to claim 4, wherein —$R^{A5}$ is —$R^{A5A}$.

17. The method according to claim 5, wherein —$R^{A5}$ is —$R^{A5A}$.

18. The method according to claim 6, wherein —$R^{A5}$ is —$R^{A5A}$.

19. The method according to claim 7 wherein —$R^{A5}$ is —$R^{A5A}$.

20. The method according to claim 8, wherein —$R^{A5}$ is —$R^{A5A}$.

21. The method according to claim 9, wherein —$R^{A5}$ is —$R^{A5A}$.

22. The method according to claim 10, wherein —$R^{A5}$ is —$R^{A5A}$.

23. The method according to claim 11, wherein —$R^{A5}$ is —$R^{A5A}$.

24. The method according to claim 12, wherein —$R^{A5}$ is —$R^{A5A}$.

25. The method according to claim 1, wherein the compound is a compound of the following formula, or a pharmaceutically acceptable salt thereof:

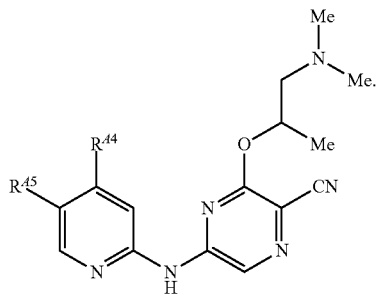

26. The method according to claim 1, wherein the compound is a compound of the following formula, or a pharmaceutically acceptable salt thereof:

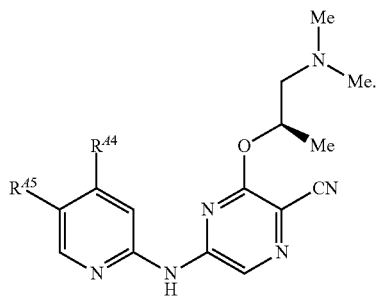

27. The method according to claim 1, wherein the compound is a compound of the following formula, or a pharmaceutically acceptable salt thereof:

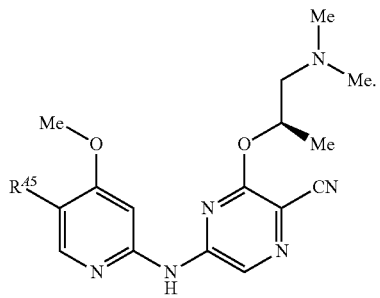

28. The method according to claim 1, wherein the compound is a compound of one of the following formulae, or a pharmaceutically acceptable salt thereof:

29. The method according to claim 1, wherein the compound is a compound of the following formula, or a pharmaceutically acceptable salt thereof:

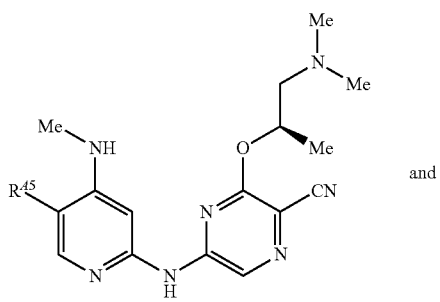

and

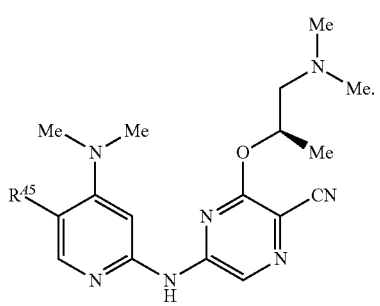

30. The method according to claim 1, wherein the compound is a compound of the following formula, or a pharmaceutically acceptable salt thereof:

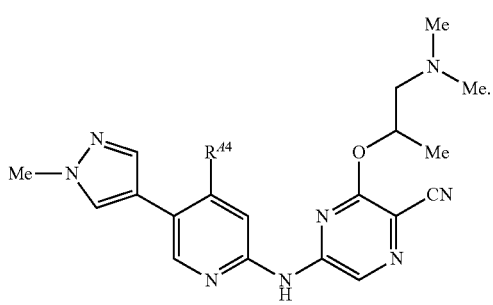

31. The method according to claim 1, wherein the compound is a compound of one of the following formulae, or a pharmaceutically acceptable salt thereof:

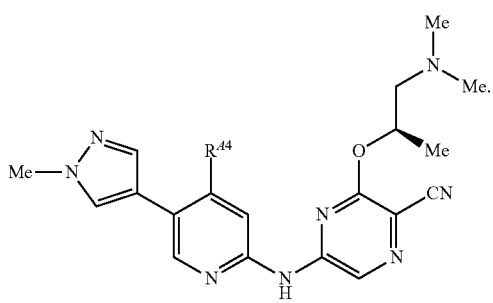

32. The method according to claim 1, wherein the compound is a compound of one of the following formulae, or a pharmaceutically acceptable salt thereof:

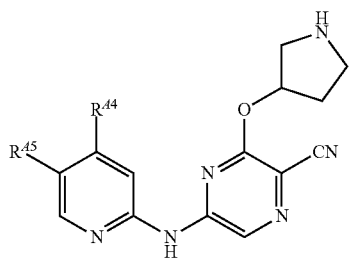

and

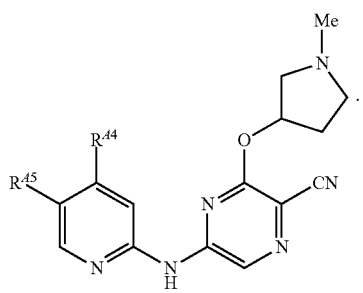

33. The method according to claim 1, wherein the compound is a compound of one of the following formulae, or a pharmaceutically acceptable salt thereof:

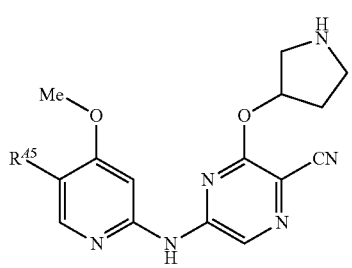

and

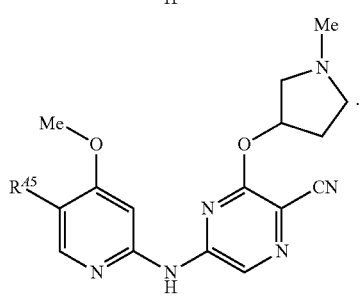

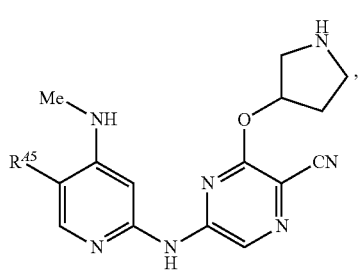

-continued
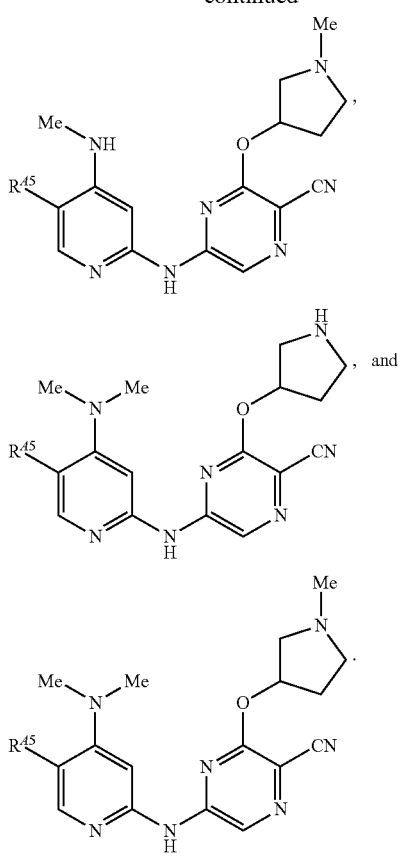
34. The method according to claim 1, wherein the compound is a compound of one of the following formulae, or a pharmaceutically acceptable salt, hydrate, or solvate thereof:
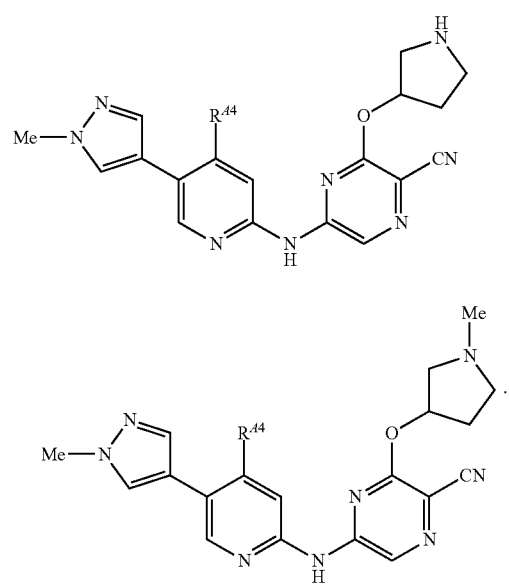
35. The method according to claim 1, wherein the compound is a compound one of the following formulae, or a pharmaceutically acceptable salt thereof:
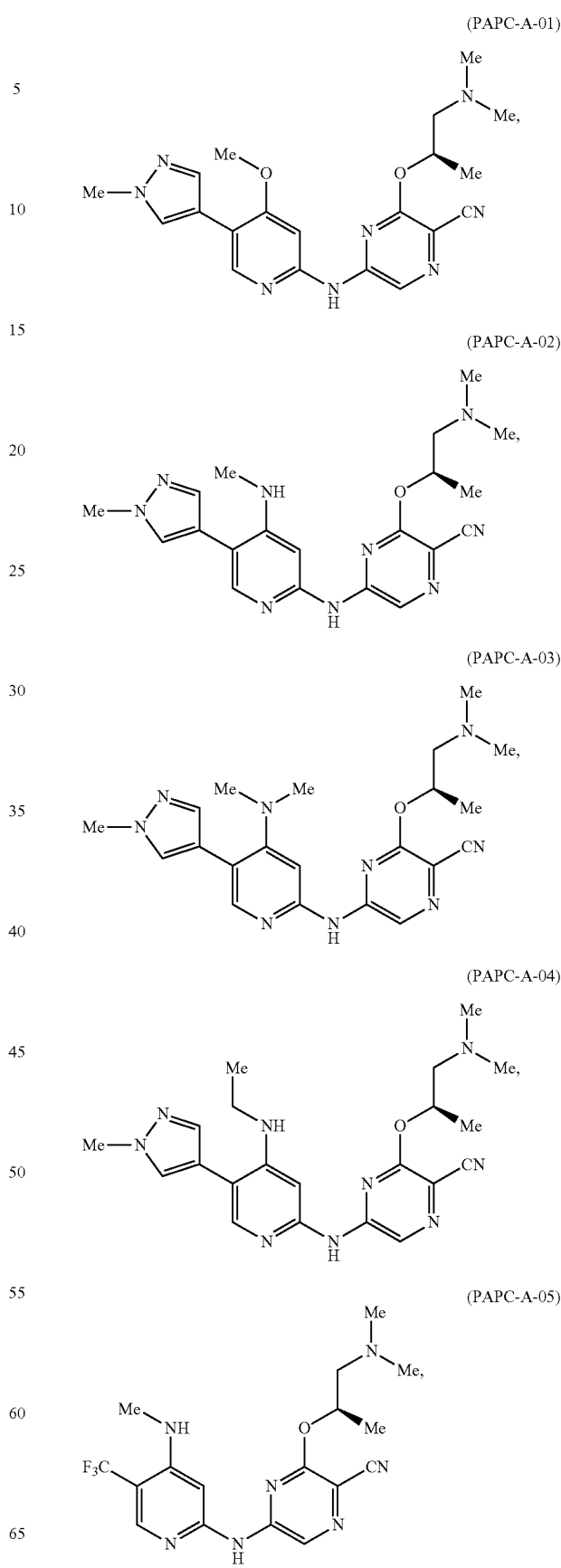

(PAPC-A-06)
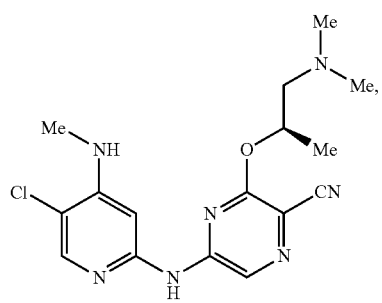
(PAPC-B-01)
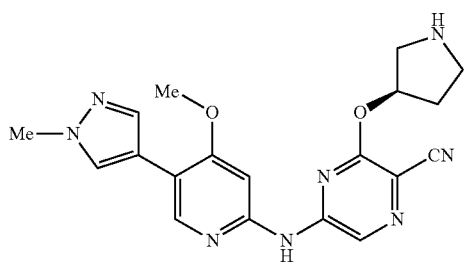
(PAPC-A-07)
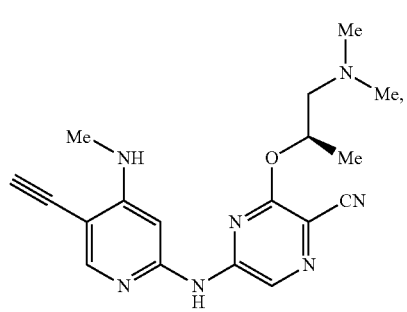
(PAPC-B-02)
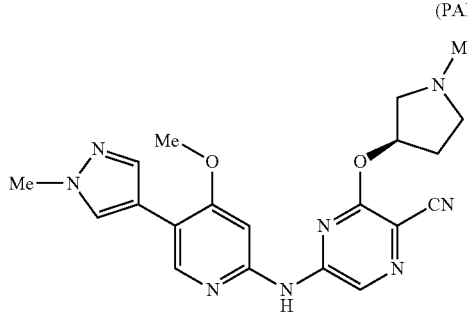
(PAPC-A-08)
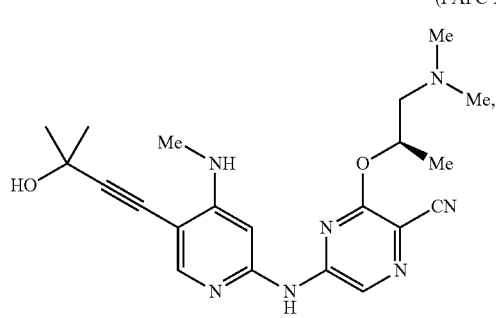
(PAPC-B-03)
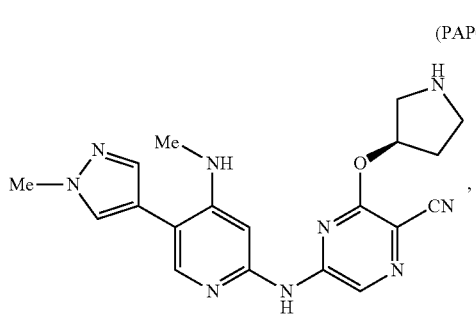
(PAPC-A-09)
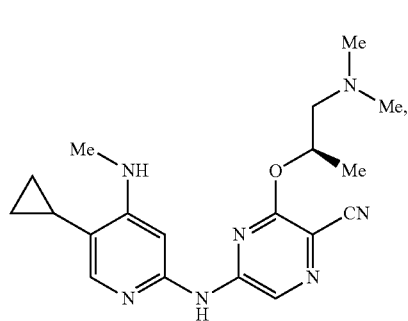
(PAPC-B-04)
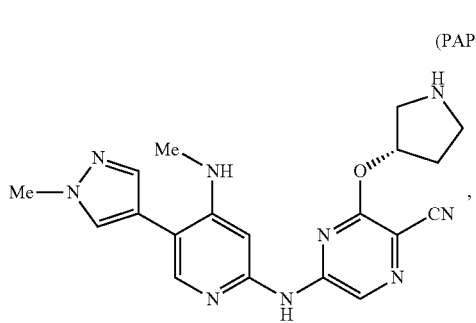
(PAPC-A-10)
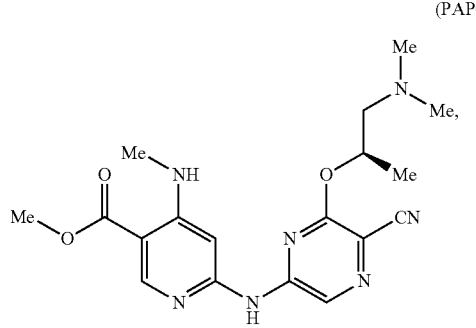
(PAPC-B-05)
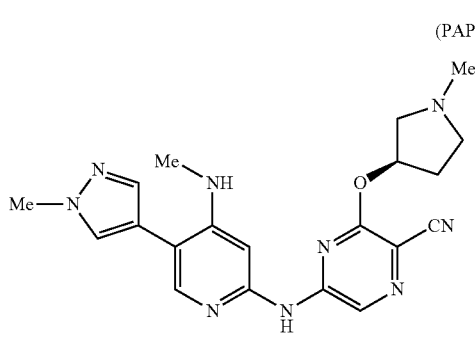

(PAPC-B-06)
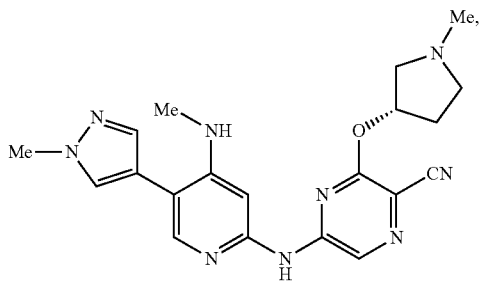

(PAPC-B-07)
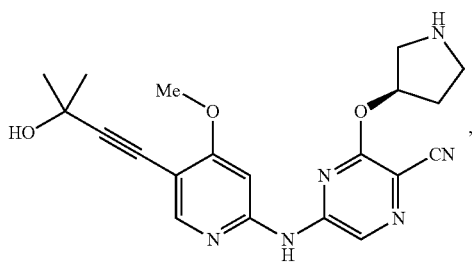

(PAPC-B-08)
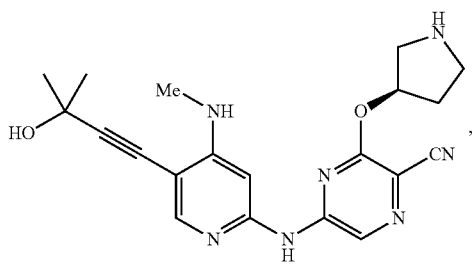

(PAPC-B-09)
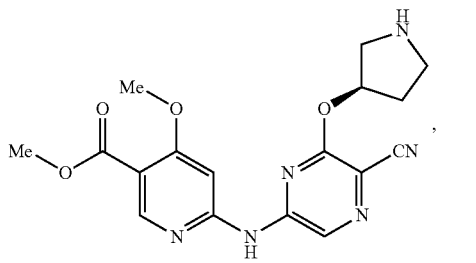

(PAPC-B-10)
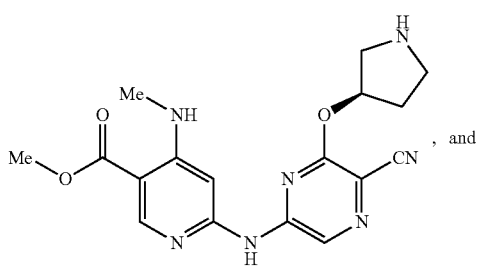

(PAPC-B-11)
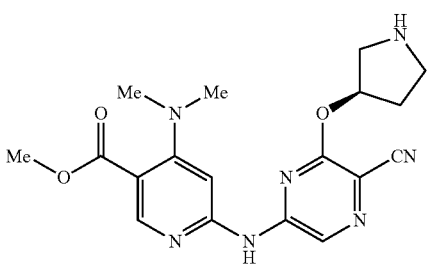

36. A method of treatment of lymphoma or leukemia comprising administering to a subject in need of treatment a therapeutically-effective amount of a compound of the following formula, or a pharmaceutically acceptable salt thereof:

(PAPC-A-01)
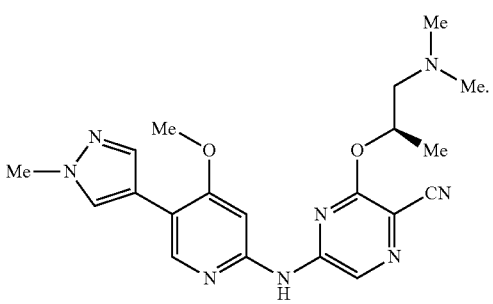

37. The method according to claim 1, wherein the treatment further comprises administering to the subject one or more other agents selected from: (a) a DNA topoisomerase I or II inhibitor; (b) a DNA damaging agent; (c) an antimetabolite or thymidylate synthase (TS) inhibitor; (d) a microtubule targeted agent; and (e) ionising radiation.

38. The method according to claim 36, wherein the treatment further comprises administering to the subject one or more other agents selected from: (a) a DNA topoisomerase I or II inhibitor; (b) a DNA damaging agent; (c) an antimetabolite or thymidylate synthase (TS) inhibitor; (d) a microtubule targeted agent; and (e) ionising radiation.

* * * * *